US006352977B1

(12) United States Patent
Astles et al.

(10) Patent No.: US 6,352,977 B1
(45) Date of Patent: Mar. 5, 2002

(54) SUBSTITUTED β-ALANINES

(75) Inventors: Peter Charles Astles; Neil Victor Harris; Andrew David Morley, all of Dagenham (GB)

(73) Assignee: Aventis Pharma Limited, West Malling (GB)

( * ) Notice: Subject to any disclaimer, the term of this patent is extended or adjusted under 35 U.S.C. 154(b) by 0 days.

(21) Appl. No.: 09/589,825

(22) Filed: Jun. 8, 2000

Related U.S. Application Data

(63) Continuation of application No. PCT/GB98/03859, filed on Dec. 23, 1998.
(60) Provisional application No. 60/092,602, filed on Jul. 13, 1998.

(51) Int. Cl.$^7$ .................... C07C 275/42; C07D 207/27; A61K 31/17; A61K 31/40
(52) U.S. Cl. ........................... 514/18; 514/19; 514/183; 514/247; 514/332; 514/343; 514/352; 514/563; 514/597; 514/245; 530/331; 546/309; 562/450; 564/51
(58) Field of Search ............................. 514/18, 19, 20, 514/183, 245, 247, 255, 256, 275, 332, 338, 343, 352, 426, 456, 466, 563, 597; 530/330, 331; 544/179, 182, 211, 212, 238, 322, 336; 546/190, 265, 279.1, 282.4, 283.7, 309; 548/558; 549/366, 439; 562/450; 564/51

(56) References Cited

FOREIGN PATENT DOCUMENTS

| | | |
|---|---|---|
| WO | WO 96/22966 | 8/1996 |
| WO | WO 97/36859 | 10/1997 |
| WO | WO 97/36862 | 10/1997 |
| WO | WO 98/04247 | 2/1998 |

*Primary Examiner*—Jeffrey E. Russel
(74) *Attorney, Agent, or Firm*—Ronald G. Ort

(57) ABSTRACT

The invention is directed to physiologically active compounds of general formula (I):

(I)

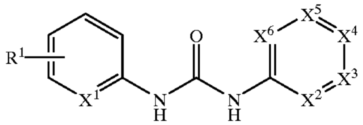

wherein $R^1$ is hydrogen, halogen, lower alkyl or lower alkoxy; $X^1$, $X^2$ and $X^6$ independently represent N or $CR^2$; and one of $X^3$, $X^4$ and $X^5$ represents $CR^3$ and the others independently represents N or $CR^2$ where $R^2$ is hydrogen, halogen, lower alkyl or lower alkoxy; and $R^3$ represents a group $—L^1—(CH_2)_n—C(=O)—N(R^4)—CH_2—CH_2—Y$; and their prodrugs, and pharmaceutically acceptable salts and solvates of such compounds and their prodrugs. Such compounds have valuable pharmaceutical properties, in particular the ability to regulate the interaction of VCAM-1 and fibronectin with the integrin VLA-4 (α4β1).

51 Claims, No Drawings

SUBSTITUTED β-ALANINES

This application is a continuation of PCT/GB98/03859, filed Dec. 23, 1998, which claims priority from GB Application No. 9727532.5, filed Dec. 23, 1997, and U.S. Application No. 60/092,602, filed Jul. 3, 1998.

This invention is directed to substituted β-alanines, their preparation, pharmaceutical compositions containing these compounds, and their pharmaceutical use in the treatment of disease states capable of being modulated by the inhibition of cell adhesion.

Cell adhesion is a process by which cells associate with each other, migrate towards a specific target or localise within the extra-cellular matrix. Many of the cell-cell and cell-extracellular matrix interactions are mediated by protein ligands (e.g. fibronectin, vitronectin and VCAM-1) and their integrin receptors [e.g. VLA-4 ($\alpha_4\beta_1$)]. Recent studies have shown these interactions to play an important part in many physiological (e.g. embryonic development and wound healing) and pathological conditions (e.g. tumour-cell invasion and metastasis, inflammation, atherosclerosis and autoimmune disease).

A wide variety of proteins serve as ligands for integrin receptors. In general, the proteins recognised by integrins fall into one of three classes: extracellular matrix proteins, plasma proteins and cell surface proteins. Extracellular matrix proteins such as collagen fibronectin, fibrinogen, laminin, thrombospondin and vitronectin bind to a number of integrins. Many of the adhesive proteins also circulate in plasma and bind to activated blood cells. Additional components in plasma that are ligands for integrins include fibrinogen and factor X. Cell bound complement C3bi and several transmembrane proteins, such as Ig-like cell adhesion molecule (ICAM-1,2,3) and vascular cell adhesion molecule (VCAM-1), which are members of the Ig superfamily, also serve as cell-surface ligands for some integrins.

Integrins are heterodimeric cell surface receptors consisting of two subunits called α and β. There are at least twelve different α-subunits (α1-α6, α-L, α-M, α-X, α-IIb, α-V and α-E) and at least nine different β (β1-β9) subunits. The integrin family can be subdivided into classes based on the β subunits, which can be associated with one or more α-subunits. The most widely distributed integrins belong to the β1 class, also known as the very late antigens (VLA). The second class of integrins are leukocyte specific receptors and consist of one of three α-subunits (α-L, α-M or α-X) complexed with the β2 protein. The cytoadhesins α-IIbβ3 and α-Vβ3, constitute the third class of integrins.

The present invention principally relates to agents which modulate the interaction of the ligand VCAM-1 with its integrin receptor α4β1 (VLA-4), which is expressed on numerous hematopoietic cells and established cell lines, including hematopoietic precursors, preipheral and cytotoxic T lymphocytes, B lymphocytes, monocytes, thymocytes and eosinophils.

The integrin α4β1 mediates both cell-cell and cell-matrix interactions. Cells expressing α4β1 bind to the carboxy-terminal cell binding domain of the extracellular matrix protein fibronectin, to the cytokine-inducible endothelial cell surface protein VCAM-1, and to each other to promote homotypic aggregation. The expression of VCAM-1 by endothelial cells is upregulated by proinflammatory cytokines such as INF-γ, TNF-α and LI-1β.

Regulation of α4β1 mediated cell adhesion is important in numerous physiological processes, including T-cell proliferation, B-cell localisation to germinal centres, and adhesion of activated T-cells and eosinophils to endothelial cells. Evidence for the involvement of VLA4/VCAM-1 interaction in various disease processes such as melanoma cell division in metastasis, T-cell infiltration of synovial membranes in rheumatoid arthritis, autoimmune diabetes, collitis and leukocyte penetration of the blood-brain barrier in experimental autoimmune encephalomyelitis, atherosclerosis, peripheral vascular disease, cardiovascular disease and multiple sclerosis, has been accumulated by investigating the role of the peptide CS-1 (the variable region of fibronectin to which α4β1 binds via the sequence Leu-Asp-Val) and antibodies specific for VLA-4 or VCAM-1 in various in vitro and in vivo experimental models of inflammation. For example, in a Streptococcal cell wall-induced experimental model of arthritis in rats, intravenous administration of CS-1 at the initiation of arthritis suppresses both acute and chronic inflammation (S. M. Wahl et al., J. Clin. Invest., 1994, 24, pages 655–662). In the oxazalone-sensitised model of inflammation (contact hypersensitivity response) in mice, intravenous administration of anti-α4 specific monoclonal antibodies significantly inhibited (50–60% reduction in the ear swelling response) the efferent response (P. L. Chisholm et al. J. Immunol., 1993, 23, pages 682–688).

We have now found a novel group of substituted β-alanines which have valuable pharmaceutical properties, in particular the ability to regulate the interaction of VCAM-1 and fibronectin with the integrin VLA-4 (α4β1).

Thus, in one aspect, the present invention is directed to compounds of general formula (I):

(I)

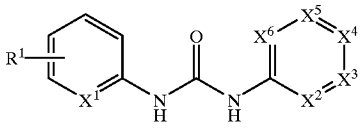

wherein:

$R^1$ is hydrogen, halogen, lower alkyl or lower alkoxy;

$X^1$, $X^2$ and $X^6$ independently represent N or $CR^2$; and one of $X^3$, $X^4$ and $X^5$ represents $CR^3$ and the others independently represents N or $CR^2$

[where $R^2$ is hydrogen, halogen, lower alkyl or lower alkoxy; and $R^3$ represents a group $—L^1—(CH_2)_n—C(=O)—N(R^4)—CH_2—CH_2—Y$ in which:

$R^4$ is aryl or heteroaryl, or $R^4$ is alkyl, alkenyl, alkynyl each optionally substituted by one or more groups chosen from halo, oxo, $R^5$, $—C(=O)—R^7$, $—NH—C(=O)—R^7$ or $—C(=O)NY^1Y^2$, or $R^4$ is cycloalkenyl, cycloalkyl or heterocycloalkyl each optionally substituted by one or more groups chosen from oxo, $R^6$ or $—L^2—R^6$ {where $R^5$ is an acidic functional group (or corresponding protected derivative), aryl, cycloalkyl, cycloalkenyl, heteroaryl, heterocycloalkyl, $—ZR^7$ or $—NY^1Y^2$; $R^6$ is an acidic functional group (or corresponding protected derivative), aryl, heteroaryl, heterocycloalkyl, —ZH, $—Z^1R^7$ or $—NY^1Y^2$; $R^7$ is alkyl, aryl, arylalkyl, cycloalkyl, cycloalkylalkyl, heteroaryl, heteroarylalkyl, heterocycloalkyl or heterocycloalkylalkyl; $L^2$ is alkylene; $Y^1$ and $Y^2$ are independently hydrogen, acyl, alkyl [optionally substituted by hydroxy, heterocycloalkyl, or one or more carboxy or $—C(=O)—NHR^8$ groups (where $R^8$ is hydrogen or lower alkyl)], alkylsulphonyl, aryl, arylalkyloxycarbonyl, arylsulphonyl, arylalkyl, heteroaryl, heteroarylalkyl, heterocycloalkyl or heterocycloalkylalkyl; or the group —$NY^1Y^2$ may form a 5–7 membered cyclic amine which (i) may be optionally substituted with one or more substituents selected from carboxamido, carboxy, hydroxy, oxo, hydroxyalkyl, $HOCH_2CH_2$—$(OCH_2CH_2)_m$— (where m is zero, or an integer one or two), or alkyl optionally substituted by carboxy or carboxamido (ii) may also contain a further heteroatom selected from O, N, S or $SO_2$ and (iii) may also be fused to additional aromatic, licteroaromatic, heterocycloalkyl or cycloalkyl rings to form a bicyclic or tricyclic ring system; Z is O or S; and $Z^1$ is O or $S(O)_m$};

$L^1$ represents a —$R^9$—$R^{10}$— linkage, in which $R^9$ is a straight or branched $C_{1-6}$alkylene chain, a straight or branched $C_{2-6}$alkenylene chain or a straight or branched $C_{2-6}$alkynylene chain, and $R^{10}$ is a direct bond, cycloalkylene, heterocycloalkylene, arylene, heteroaryidiyl, —C(=Z)—$NR^{11}$—, —$NR^{11}$—C(=Z)—, —$Z^1$, —$NR^{11}$—, —C(=O)—, —C(=$NOR^{11}$)—, —$NR^{11}$—C(=Z)—$NR^{11}$—, —$SO_2$—$NR^{11}$—, —$NR^{11}$—$SO_2$—, —O—C(=O)—, —C(=O)—O—, —$NR^{11}$—C(=O)—O— or —O—C(=O)—$NR^{11}$— (where $R^{11}$ is a hydrogen atom or $R^4$); but excluding compounds where an oxygen, nitrogen or sulphur atom is attached directly to a carbon carbon multiple bond;

Y is carboxy (or an acid bioisostere) or —C(=O)—$NY^1Y^2$; and n is an integer from 1 to 6];

and their prodrugs, and pharmaceutically acceptable salts and solvates (e.g. hydrates) of such compounds and their prodrugs.

In the present specification, the term "compounds of the invention", and equivalent expressions, are meant to embrace compounds of general formula (I) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

As used above, and throughout the description of the invention, the following terms, unless otherwise indicated, shall be understood to have the following meanings:

"Patient" includes both human and other mammals.

"Acid bioisostere" means a group which has chemical and physical similarities producing broadly similar biological properties to a carboxy group (see Lipinski, Annual Reports in Medicinal Chemistry, 1986,21,p283 "Bioisosterism In Drug Design"; Yun, Hwahak Sekyc, 1993,33,p576–579 "Application Of Bioisosterism To New Drug Design"; Zhao. Huaxue Tongbao, 1995,p34–38 "Bioisostcric Replacement And Development Of Lead Compounds In Drug Design"; Graham, Theochem, 1995,343,p105–109 "Theoretical Studies Apphed To Drug Design:ab initio Electronic Distributions In Bioisosteres"). Examples of suitable acid bioisosteres include: —C(=O)—NHOH, —C(=O)—$CH_2OH$, —C(=O)—$CH_2SH$, —C(=O)—NH—CN, sulpho, phosphono, alkylsulphonylcarbamoyl, tetrazolyl, arylsulphonylcarbamoyl, heteroarylsulphonylcarbamoyl, N-methoxycarbamoyl, 3-hydroxy-3-cyclobutene-1,2-dione, 3,5-dioxo-1,2,4-oxadiazolidinyl or heterocyclic phenols such as 3-hydroxyisoxazolyl and 3-hydoxy-1-methylpyrazolyl.

"Acidic functional group" means a group with an acidic hydrogen within it. The "corresponding protected derivatives" are those where the acidic hydrogen atom has been replaced with a suitable protecting group. For suitable protecting groups see T. W. Greene and P. G. M. Wuts in "Protective Groups in Organic Chemistry" John Wiley and Sons, 1991. Exemplary acidic functional groups include carboxyl (and acid bioisosteres), hydroxy, mercapto and imidazole. Exemplary protected derivatives include esters of carboxy groups, ethers of hydroxy groups, thioethers of mercapto groups and N-arylalkyl(e.g. N-benzyl) derivatives of imidazoles.

"Acyl" means an H—CO— or alkyl—CO— group in which the alkyl group is as described herein.

"Acylamino" is an acyl—NH— group wherein acyl is as defined herein.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably about 2 to about 4 carbon atoms in the chain. "Branched", as used herein and throughout the text, means that one or more lower alkyl groups such as methyl, ethyl or propyl are attached to a linear chain; here a linear alkenyl chain. "Lower alkenyl" means about 2 to about 4 carbon atoms in the chain which may be straight or branched. Exemplary alkenyl groups include ethenyl, propenyl, n-butenyl, i-butenyl, 3-methylbut-2-enyl, n-pentenyl, heptenyl, octenyl, cyclohexylbutenyl and decenyl.

"Alkenylene" means an aliphatic bivalent radical derived from a straighl or branched alkenyl group, in which the alkenyl group is as described herein. Exemplary alkenylene radicals include $C_{2-4}$alkenylene radicals such as vinylene and propylene.

"Alkoxy" means an alkyl—O— group in which the alkyl group is as described herein. Exemplary alkoxy groups include methoxy, ethoxy, n-propoxy, i-propoxy, n-butoxy and heptoxy.

"Alkoxycarbonyl" means an alkyl—O—CO— group in which the alkyl group is as described herein. Exemplary alkoxycarbonyl groups include methoxy- and ethoxycarbonyl.

"Alkyl" means, unless otherwise specified, an aliphatic hydrocarbon group which may be straight or branched having about 1 to about 15 carbon atoms in the chain optionally substituted by one or more halogen atoms. Particular alkyl groups have from 1 to about 6 carbon atoms. "Lower alkyl" as a group or part of a lower alkoxy group means unless otherwise specified, an aliphatic hydrocarbon group which may be straight or branched having about 1 to about 4 carbon atoms in the chain. Exemplary alkyl groups include methyl, ethyl, n-propyl, i-propyl, n-butyl, s-butyl, t-butyl, n-pentyl, 3-pentyl, heptyl, octyl, nonyl, decyl and dodecyl.

"Alkylene" means an aliphatic bivalent radical derived from a straight or branched alkyl group, in which the alkyl group is as described herein. Exemplary alkylene radicals include $C_{1-4}$alkylene radicals such as methylene, ethylene and trimethylene.

"Alkylsulphinyl" means an alkyl-SO—, group in which the alkyl group is as previously described. Preferred alkylsulphinyl groups are those in which the alkyl group is $C_{1-4}$alkyl.

"Alkylsulphonyl" means an alkyl-$SO_2$— group in which the alkyl group is as previously described. Preferred alkylsulphonyl groups are those in which the alkyl group is $C_{1-4}$alkyl.

"Alkylsulphonylcarbamoyl" means an alkyl-$SO_2$—NH—C(═O)— group in which the alkyl group is as previously described. Preferred alkylsulphonylcarbamoyl groups are those in which the alkyl group is $C_{1-4}$alkyl.

"Alkylthio" means an alkyl-S— group in which the alkyl group is as previously described. Exemplary alkylthio groups include methylthio, ethylthio, isopropyltilio and lieptylthio.

"Alkynyl" means an aliphatic hydrocarbon group containing a carbon-carbon triple bond and which may be straight or branched having about 2 to about 15 carbon atoms in the chain.

Preferred alkynyl groups have 2 to about 12 carbon atoms in the chain; and more preferably about 2 to about 4 carbon atoms in the chain. Exemplary alkynyl groups include ethynyl, propynyl, n-butynyl, i-butynyl, 3-methylbut-2-ynyl, and n-pentynyl.

"Alkynylene" means an aliphatic bivalent radical derived from a straight or branched alkynyl group, in which the alkynyl group is as described herein. Exemplary alkynylene radicals include $C_{2-4}$alkynylene radicals such as ethynylene and propynylene.

"Aroyl" means an aryl-CO— group in which the aryl group is as described herein. Exemplary aroyl groups include benzoyl and 1- and 2-naphthoyl.

"Aroylamino" is an aroyl-NH— group wherein aroyl is as previously defined.

"Aryl" as a group or part of a group denotes: (i) an optionally substituted monocyclic or multicyclic aromatic carbocyclic moiety of about 6 to about 14 carbon atoms or (ii) an optionally substituted partially saturated multicyclic aromatic carbocyclic moiety in which an aryl and a cycloalkyl or cycloalkenyl group are fused together to form a cyclic structure such as a tetrahydronaphthyl, indenyl or indanyl ring. When $R^4$ contains an optionally substituted aryl group, this may particularly represent optionally substituted phenyl with one or more aryl group substituents which may be the same or different, where "aryl group substituent" includes, for example, acyl, acylamino, alkoxy, alkoxycarbonyl, alkylsulphinyl, alkylsulphonyl, alkylthio, aroyl, aroylamino, aryl, arylalkyloxy, arylalkyloxycarbonyl, arylalkylthio, aryloxy, aryloxycarbonyl, arylsulphinyl, arylsulphonyl, arylthio, carboxy, cyano, halo, heteroaroyl, heteroaryl, heteroarylalkyloxy, heteroarylamino, heteroaryloxy, hydroxy, nitro, trifluoromethyl, $Y^3Y^4N$—, $Y^3Y^4NCO$—, $Y^3Y^4NSO_2$—(where $Y^3$ and $Y^4$ are independently hydrogen, alkyl, ar and arylalkyl), $Y^3Y^4N$—$L^3$—$Z^2$— (where $L^3$ is $C_{2-6}$alkylene and $Z^2$ is O, $NR^8$ or $S(O)_m$), alkylC(═O)—$Y^3N$—, alkyl$SO_2$—$Y^3N$— or alkyl optionally substituted with aryl, heteroaryl, hydroxy, or $Y^3Y^4N$—.

"Arylalkyl" means an aryl-alkyl- group in which the aryl and alkyl moieties are as previously described. Preferred arylalkyl groups contain a $C_{1-4}$alkyl moiety. Exemplary arylalkyl groups include benzyl, 2-phenethyl and naphthienemethyl.

"Arylalkyloxy" means an arylalkyl-O— group in which the arylalkyl groups is as previously described. Exemplary arylalkyloxy groups include benzyloxy and 1- or 2-naphthalenemethoxy.

"Arylalkyloxycarbonyl" means an arylalkyl-O—CO— group in which the arylalkyl groups is as previously described. An exemplary arylalkyloxycarbonyl group is benzyloxycarbonyl.

"Arylalkylthio" means an arylalkyl-S— group in which the arylalkyl group is as previously described. An exemplary arylalkylthio group is benzylthio.

"Arylene" means an optionally substituted bivalent radical derived from an aryl group as defined above. Exemplary arylene groups include optionally substituted phenylene, naphthylene and indanylene. Suitable substituents include one or more "aryl group substituents" as defined above, particularly halogen, methyl or methoxy.

"Aryloxy" means an aryl-O— group in which the aryl group is as previously described. Exemplary aryloxy groups include optionally substituted phenoxy and naphthoxy.

"Aryloxycarbonyl" means an aryl-O—CO— group in which the aryl group is as previously described. Exemplary aryloxycarbonyl groups include phenoxycarbonyl and naphthoxycarbonyl.

"Arylsulphinyl" means an aryl-SO— group in which the aryl group is as previously described.

"Arylsulphonyl" means an aryl-$SO_2$— group in which the aryl group is as previously described.

"Arylsulphonylcarbamoyl" means an aryl-$SO_2$—NH—C(═O)— group in which the aryl group is as previously described.

"Arylthio" means an aryl-S— group in which the aryl group is as previously described. Exemplary aryltliio groups include phenylthio and naphthylthio.

"Azaheteroaryl" means an aromatic carbocyclic moiety of about 5 to about 10 ring members in which one of the ring members is nitrogen and the other ring members are chosen from carbon, oxygen, sulphur, or nitrogen. Examples of azaheteroaryl groups include pyridyl, pyrimidinyl, quinolinyl, isoquinolinyl, quinazolinyl, imidazolyl, and benzimidazolyl.

"Cydoalkenyl" means a non-aromatic monocyclic or multicyclic ring system containing at least one carbon-carbon double bond and having about 3 to about 10 car bon atoms. Exemplary monocyclic cycloalkenyl rings include $C_{3-8}$cycloalkenyl rings such as cyclopentenyl, cyclohexenyl or cycloheptenyl.

"Cycloalkyl" means a saturated monocyclic or bicyclic ring system of about 3 to about 10 carbon atoms optionally substituted by oxo. Exemplary monocyclic cycloalkyl rings include $C_{3-8}$cycloalkyl such as cyclopropyl, cyclopentyl, cyclohexyl and cycloheptyl.

"Cycloalkylalkyl" means a cycloalkyl-alkyl- group in which the cycloalkyl and alkyl moieties are as previously described. Exemplary monocyclic cycloalkylalkyl groups include $C_{3-8}$cyclo alkyl$C_{1-4}$alkyl groups such as cyclopropylmethyl, cyclopentylmethyl, cyclohexylmethyl and cycloheptylmethyl.

"Cycloalkylene" means a divalent radical derived from a cycloalkyl group as defined above. Exemplary cycloalkylene radicals include $C_{3-8}$cycloalkylene radicals such as cyclopentylene and cyclohexylene.

"Halo" or "halogen" means fluoro, chloro, bromo, or lodo. Preferred are fluoro or chloro.

"Heteroaroyl" means a heteroaryl-CO— group in which the heteroaryl group is as described herein. Exemplary groups include pyridylcarbonyl.

"Heteroaryl" as a group or part of a group denotes: (i) an optionally substituted aromatic monocyclic or multicyclic organic moiety of about 5 to about 10 ring members in which one or more of the ring members is/are element(s) other than carbon, for example nitrogen, oxygen or sulphur (examples of such groups include benzimidazolyl, benzthriazolyl, furyl, imidazolyl a indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazoly groups, optionally substituted by one or more aryl group substituents as defined above); (ii) an optionally substituted partially saturated miulticyclic heterocarbocyclic moiety in which a heteroaryl and a cycloalkyl or cycloalkenyl group are fused together to form a cyclic structure (examples of such groups include pyrindanyl groups). Optional substituents include one or more "aryl group substituents" as defined above. When $L^1$ or $R^4$ contains an optionally substituted heteroaryl group this may particularly represent an optionally substituted "azaheteroaryl" group.

"Heteroarylalkyl" means a heteroaryl-alkyl- group in which the heteroaryl and alkyl moieties are as previously described. Preferred heteroarylalkyl groups contain a $C_{1-4}$alkyl moiety such as optionally substituted pyridyl$C_{1-4}$alkyl (e.g. optionally substituted pyridylmethyl).

"Heteroarylalkyloxy" means an heteroarylalkyl-O— group in which the heteroarylalkyl group is as previously described. Preferred heteroarylalkyloxy groups include heteroaryl$C_{1-4}$alkyloxy such as optionally substituted pyridyl$C_{1-4}$alkyloxy (e.g. optionally substituted pyridylmethoxy).

"Heteroarylamino" means a heteroaryl-NH— group in which the heteroaryl moiety are as previously described.

"Heteroaryldiyl" means a bivalent radical derived from a heteroaryl group as defined above.

"Heteroaryloxy" means an heteroaryl-O— group in which the heteroaryl group is as previously described. Exemplary heteroaryloxy groups include optionally substituted pyridyloxy. "Heteroarylsulphonylckrbamoyl" means a heteroaryl-$SO_2$—NH—C(═O)— group in which the heteroaryl group is as previously described.

"Heterocycloalkyl" means: (i) a cycloalkyl group of about 3 to 7 ring members in which one or more of the ring carbon atoms is replaced by O, S or $NY^5$ (where $Y^5$ is hydrogen, alkyl, arylalkyl, and aryl); (ii) a partially saturated bicyclic system in which an aryl or heteroaryl ring is fused to a heterocycloalkyl ring as defined in (i) above. Examples of (ii) include 1,4-benzodioxanyl, 1,3-benzodioxolyl, chromanyl, dihydrobenzofuranyl, indolinyl and dihydropyrrolopyridinyl groups).

"Heterocycloalkylalkyl" means a heterocycloalkyl-alkyl-group in which the heterocycloalkyl and alkyl moieties are as previously described.

"Heterocycloalkylene" means a bivalent radical derived from a heterocycloalkyl group as defined above.

"Hydroxyalkyl" means a HO-alkyl- group in which alkyl is as previously defined. Preferred hydroxyalkyl groups contain $C_{1-4}$alkyl for example hydroxymethyl and 2-hydroxyethyl.

"$Y^3Y^4N$—" means a substituted or unsubstituted amino group, wherein $Y^3$ and $Y^4$ are as previously described. Exemplary groups include amino ($H_2N$—), methylamino, ethylmethylamino, dimethylamino and diethylamino.

"$Y^3Y^4NCO$—" means a substituted or unsubstituted carbamoyl group, wherein $Y^3$ and $Y^4$ are as previously described. Exemplary groups are carbamoyl ($H_2NCO$—) and dimethylcarbamoyl ($Me_2NCO$—).

"$Y^3Y^4NSO_2$—" means a substituted or unsubstituted sulphamoyl group, wherein $Y^3$ and $Y^4$ are as previously described. Exemplary groups are sulphamoyl ($H_2NSO_2$—) and dimethylsulphamoyl ($Me_2NSO_2$—).

"Prodrug" means a compound which is convertible in vivo by metabolic means (e.g. by hydrolysis) to a compound of formula (I), including N-oxides thereof. For example an ester of a compound of formula (I) containing a hydroxy group may be convertible by hydrolysis in vivo to the parent molecule. Alternatively an ester of a compound of formula (I) containing a carboxy group may be convertible by hydrolysis in vivo to the parent molecule.

Suitable esters of compounds of formula (I) containing a hydroxy group, are for example acetates, citrates, lactates, tartrates, malonates, oxalates, salicylates, propionates, succinates, fumarates, maleates, methylene-bis-β-hydroxynaphthoates, gentisates, isethionates, di-p-toluoyltartrates, metlianesulplionates, ethanesulphonates, benzenesulplionates, p-toluenesulphonates, cyclohexylsulphanates and quinates.

An especially useful class of esters of compounds of formula (I) containing a hydroxy group, may be formed from acid moieties selected from those described by Bundgaard et. al., J. Med. Chem., 1989, 32, page 2503–2507, and include substituted (aminomethyl)-benzoates, for example dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl) benzoates.

Where the compound of the invention contains a carboxy group, or a sufficiently acidic bioisostere, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the patient in pharmaceutical doses of the salts, so that the beneficial inhibitory effects inherent in the free base are not vitiated by side effects ascribable to the cations. Pharmaceutically acceptable salts, including those derived from alkali and alkaline earth metal salts, within the scope of the invention include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)aminomethane, tetramethylammonium hydroxide, and the like.

Some of the compounds of the present invention are basic, and such compounds are useful in the form of the free base or in the form of a pharmaceutically acceptable acid addition salt thereof.

Acid addition salts are a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention include those derived from mineral acids and organic acids, and include hydrohalides, e.g. hydrochlorides and hydrobromides, sulphates, phosphates, nitrates, sulphamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates and quinates.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

With reference to formula (I) above, the following are particular and preferred groupings:

$R^1$ may particularly represent hydrogen, especially when $X^1$ represents C-$R^2$ where $R^2$ is lower alkyl or lower alkoxy.

$X^1$ may particularly represent $CR^2$, especially where $R^2$ is $C_{1-4}$alkyl (e.g. methyl) or $C_{1-4}$alkoxy (e.g. methoxy).

$X^2$ may particularly represent $CR^2$, especially where $R^2$ is $C_{1-4}$alkyl (e.g. methyl) or $C_{1-4}$alkoxy (e.g. methoxy).

$X^3$ may particularly represent $CR^2$ and is preferably CH.

$X^6$ may particularly represent $CR^2$ and is preferably CH.

One of $X^4$ and $X^5$ may particularly represent $CR^3$ and the other represents $CR^2$, especially CH.

Within $R^3$ the moiety $L^1$ may particularly represent a —$R^9$—$R^{10}$— linkage where $R^9$ represents a straight or branched $C_{1-6}$alkylene chain, especially a straight $C_{1-4}$alkylene chain such as methylene or ethylene, and $R^{10}$ represents —C(═Z)—$NR^{11}$—, preferably —C(═O)—$NR^{11}$— especially where $R^{11}$ is:

(i) hydrogen;

(ii) $C_{1-6}$alkyl (e.g. $C_{1-4}$alkyl groups such as ethyl, propyl or especially methyl);

(iii) $C_{1-6}$alkyl (especially $C_{1-3}$alkyl) substituted by $R^5$, where $R^5$ is aryl (e.g. phenyl);

(iv) $C_{1-6}$alkyl (especially $C_{1-3}$alkyl) substituted by $R^5$, where $R^5$ is heteroaryl (exemplary heteroaryl groups include indolyl, imidazolyl, pyridyl and furyl);

(v) $C_{1-6}$alkyl (especially $C_{1-3}$alkyl) substituted by $R^5$, where $R^5$ is cycloalkyl (e.g. $C_{3-8}$cycloalkyl such as cyclopentyl and cyclohexyl);

(vi) $C_{1-6}$alkyl (especially $C_{1-3}$alkyl) substituted by $R^5$, where $R^5$ is carboxy (or an acid bioisostere); or (vii) $C_{1-6}$alkyl (e.g. $C_{1-4}$alkyl such as ethyl or propyl) substituted by $R^5$, where $R^5$ is —$NY^1Y^2$ (exemplary —$NY^1Y^2$ groups include acylamino, aryl(alkyl)amino, N-pyrrolidinyl and 2-oxo-N-pyrrolidinyl).

Within $R^3$ the moiety $R^4$ may particularly represent straight or branched $C_{1-10}$alkyl (e.g. methyl, ethyl, n-propyl, i-propyl, n-butyl, i-butyl, n-pentyl, i-pentyl, n-hexyl, n-heptyl, n-octyl, 1,5-dimethylhexyl, n-nonyl or n-decyl).

Within $R^3$ the moiety $R^4$ may also particularly represent straight or branched $C_{1-6}$alkyl (e.g. methyl, ethyl, n-propyl, i-propyl or n-butyl) substituted by $R^5$, where $R^5$ is aryl. Exemplary aryl groups include phenyl optionally substituted by one or more "aryl group substituents", for example alkoxyphenyl, dialkoxyphenyl, arylalkyloxy(alkoxy)phenyl, halophenyl, dialkylaminophenyl, trifluoromethylphenyl and metlianesulphonylphenyl. $R^4$ is preferably straight or branched $C_{1-3}$alkyl substituted by di$C_{1-3}$alkoxyphenyl and is particularly 3,4-di$C_{1-3}$alkoxybenzyl.

Within $R^3$ the moiety $R^4$ may also particularly represent straight or branched $C_{1-6}$alkyl (e.g. methyl, ethyl, n-propyl, i-propyl or n-butyl) substituted by $R^5$, where $R^5$ is heteroaryl. Exemplary heteroaryl groups include indolyl, imidazolyl, pyridyl and furyl. $R^4$ is preferably straight or branched $C_{1-3}$alkyl substituted by azaheteroaryl and is particularly 3-(imidazol-1-yl)-$C_{1-3}$alkyl).

Within $R^3$ the moiety $R^4$ may also particularly represent straight or branched $C_{1-6}$alkyl (e.g. methyl, ethyl, n-propyl, i-propyl or n-butyl) substituted by $R^5$, where $R^5$ is $C_{3-8}$cycloalkyl. $R^4$ is preferably straight or branched $C_{1-3}$alkyl substituted by $C_{5-6}$cycloalkyl.

Within $R^3$ the moiety $R^4$ may also particularly represent straight or branched $C_{1-6}$alkyl (e.g. methyl, ethyl, n-propyl, i-propyl or n-butyl) substituted by $R^5$, where $R^5$ is $C_{1-6}$alkoxy, especially $C_{1-4}$alkoxy such as methoxy.

Within $R^3$ the moiety $R^4$ may also particularly represent straight or branched $C_{1-6}$alkyl (e.g. methyl, ethyl, n-propyl, i-propyl or n-butyl) substituted by $R^5$, where $R^5$ is halo.

Within $R^3$ the moiety $R^4$ may also particularly represent straight or branched $C_{1-6}$alkyl (e.g. methyl, ethyl, n-propyl, i-propyl or n-butyl) substituted by $R^5$, where $R^5$ is an acidic functional group. $R^4$ is preferably straight or branched $C_{1-3}$alkyl substituted by carboxy.

Within $R^3$ the moiety $R^4$ may also particularly represent straight or branched $C_{1-6}$alkyl (e.g. methyl, ethyl, n-propyl, i-propyl or n-butyl) substituted by $R^5$, where $R^5$ is heterocycloalkyl. Exemplary heterocycloalkyl groups include benzodioxolyl and benzodioxanyl. $R^4$ is preferably straight or branched $C_{1-3}$alkyl substituted by benzodioxolyl and benzodioxanyl.

Within $R^3$ the moiety $R^4$ may also particularly represent straight or branched $C_{1-6}$alkyl (e.g. methyl, ethyl, n-propyl, i-propyl or n-butyl) substituted by —$NY^1Y^2$. Exemplary —$NY^1Y^2$ groups include acyl,amino, aryl(alkylamino) and —$NY^1Y^2$ groups derived from 5–7 membered cyclic amines such as morpholine, piperidine, pyrrolidine and 2-oxo-pyrrolidine. $R^4$ is preferably straight or branched $C_{2-3}$alkyl substituted by an N-linked 5–7 membered cyclic amine, especially 3-(2-oxo-pyrrolidin-1-yl)-$C_{2-3}$alkyl.

Within $R^3$ the moiety $R^4$ may also particularly represent $C_{1-4}$alkenyl (e.g. allyl).

Within $R^3$ the moiety n may particularly represent the integer 1 to 3, especially 1.

Within $R^3$ the moiety Y may particularly represent carboxy or an acid bioisostere, especially carboxy.

It is to be understood that this invention covers all appropriate combinations of the particular and preferred groupings referred to herein.

A particular group of compounds of the invention are compounds of formula (Ia):

(1a)

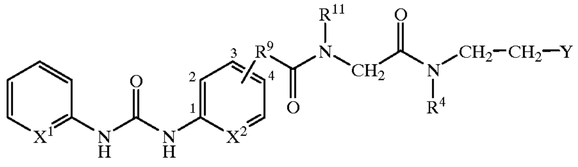

in which $R^4$, $R^9$, $R^{11}$ and Y are as hereinbefore defined, $X^1$ and $X^2$ each independently represent $CR^2$ (wherein each $R^2$ group is as hereinbefore defined), and —$R^9$—CON($R^{11}$)—$CH_2$—CON($R^4$)—$CH_2$—$CH_2$-Y is attached at the ring 3 or 4 position, and their prodrugs and pharmaceutically acceptable salts, and solvates (e.g. hydrates) of compounds of formula (Ia) and their prodrugs. Compounds of formula (Ia) in which $R^4$ represents straight or branched $C_{1-10}$alkyl (e.g. methyl, ethyl, n-propyl, i-propyl, n-butyl, i-butyl, n-pentyl, i-pentyl, n-hexyl, n-heptyl, n-octyl, 1,5-dimethylhexyl, n-nonyl, or n-decyl) are preferred.

Compounds of formula (Ia) in which $R^4$ represents straight or branched $C_{1-6}$alkyl (e.g. methyl, ethyl, n-propyl, i-propyl or n-butyl) substituted by $R^5$, where $R^5$ is aryl are also preferred. Exemplary aryl groups include phenyl optionally substituted by one or more "aryl group substituents", for example alkoxyphenyl, dialkoxyphenyl, arylalkyloxy(akoxy)phenyl, halophenyl, dialkylaminophenyl, trifluoromethyl and methanesulphonylphenyl. Compounds of formula (Ia) in which $R^4$ represents straight or branched $C_{1-3}$alkyl substituted by di$C_{1-3}$alkoxyphenyl, particularly 3,4-di$C_{1-3}$alkoxybenzyl (e.g. 3,4-dimethoxybenzyl 3,4-diethoxybenzyl and 3-ethoxy-4-methoxybenzyl), are especially preferred.

Compounds of formula (Ia) in which $R^4$ represents straight or branched $C_{1-6}$alkyl (e.g. methyl, ethyl, n-propyl, i-propyl or n-butyl) substituted by $R^5$, where $R^5$ is heteroaryl are also preferred. Exemplary heteroaryl groups include indolyl, imidazolyl, pyridyl and furyl. Compounds of formula (Ia) in which $R^4$ represents straight or branched $C_{1-3}$alkyl substituted by azaheteroaryl, particularly 3-(imidazol-1-yl)-$C_{1-3}$alkyl (e.g. 3-(imidazol-1-yl)-propyl), are especially preferred.

Compounds of formula (Ia) in which $R^4$ represents straight or branched $C_{1-6}$alkyl (e.g. methyl, ethyl, n-propyl, i-propyl or n-butyl) substituted by $R^5$, where $R^5$ is $C_{3-8}$cycloalkyl are also preferred. Compounds of formula (Ia) in which $R^4$ represents straight or branched $C_{1-3}$alkyl substituted by $C_{5-6}$cycloalkyl groups are especially preferred.

Compounds of formula (Ia) in which $R^4$ represents straight or branched $C_{1-6}$alkyl (e.g. methyl, ethyl, n-propyl, i-propyl or n-butyl) substituted by $R^5$, where $R^5$ is $C_{1-6}$alkoxy, especially $C_{1-4}$alkoxy (e.g. methoxy), are also preferred.

Compounds of formula (Ia) in which $R^4$ represents straight or branched $C_{1-6}$alkyl (e.g. methyl, ethyl, n-propyl, i-propyl or n-butyl) substituted by $R^5$, where $R^5$ is halo are also preferred.

Compounds of formula (Ia) in which $R^4$ represents straight or branched $C_{1-6}$alkyl (e.g. methyl, ethyl, n-propyl, i-propyl or n-butyl) substituted by $R^5$, where $R^5$ is an acidic functional group are also preferred. Compounds of formula (Ia) in which $R^4$ is straight or branched $C_{1-3}$alkyl substituted by carboxy are especially preferred.

Compounds of formula (Ia) in which $R^4$ represents straight or branched $C_{1-6}$alkyl (e.g. methyl, ethyl, n-propyl, i-propyl or n-butyl) substituted by $R^5$, where $R^5$ is heterocycloalkyl are also preferred. Compounds of formula (Ia) in which $R^4$ represents straight or branched $C_{1-3}$alkyl substituted by benzodioxolyl and benzodioxanyl are especially preferred.

Compounds of formula (Ia) in which $R^4$ represents straight or branched $C_{1-6}$alkyl (e.g. methyl, ethyl, n-propyl, i-propyl or n-butyl) substituted by $—NY^1Y^2$ are also preferred. Exemplary $—NY^1Y^2$ groups include acylamino, aryl(alkylamino) and $—NY^1Y^2$ groups derived from 5–7 membered cyclic amines such as morpholine, piperidine, pyrrolidine and 2-oxo-pyrrolidine. Compounds of formula (Ia) in which $R^4$ represents straight or branched $C_{1-3}$alkyl substituted by an N-linked 5–7 membered cyclic amine, especially 3-(2-oxo-pyrrolidin-1-yl)-$C_{1-3}$alkyl (e.g. 3-(2-oxo-pyrrolidin-1-yl)-propyl), are particularly preferred.

Compounds of formula (Ia) in which $R^4$ represents $C_{1-4}$alkenyl (e.g. allyl) are also preferred.

Compounds of formula (Ia) in which $R^9$ represents a straight or branched $C_{1-6}$alkylene chain, especially a straight or branched $C_{1-4}$alkylene chain, more especially methylene, are preferred.

Compounds of formula (Ia) in which $R^{11}$ represents hydrogen are preferred.

Compounds of formula (Ia) in which $R^{11}$ represents straight or branched $C_{1-4}$alkyl, particularly methyl, are also preferred.

Compounds of formula (Ia) in which $R^{11}$ represents straight or branched $C_{1-3}$alkyl substituted by $R^5$, where $R^5$ is aryl (e.g. phenyl), are also preferred. Compounds of formula (Ia) in which $R^{11}$ represents straight chain $C_{1-3}$alkyl substituted by phenyl are especially preferred.

Compounds of formula (Ia) in which $R^{11}$ represents straight or branched $C_{1-3}$alkyl substituted by $R^5$, where $R^5$ is heteroaryl, are also preferred. Exemplary heteroaryl groups include indolyl, imidazolyl, pyridyl and furyl. Compounds of formula (Ia) in which $R^{11}$ represents straight chain $C_{1-3}$alkyl substituted by azaheteroaryl (e.g. imidazolyl or pyridyl) are especially preferred.

Compounds of formula (Ia) in which $R^{11}$ represents straight or branched $C_{1-3}$alkyl substituted by $R^5$, where $R^5$ is cycloalkyl (e.g. $C_{3-8}$cycloalkyl), are also preferred. Exemplary $C_{3-8}$cycloalkyl groups include cyclopentyl and cyclohexyl. Compounds of formula (Ia) in which $R^{11}$ represents straight chain $C_{1-3}$alkyl substituted by cyclohexyl are especially preferred.

Compounds of formula (Ia) in which $R^{11}$ represents straight or branched $C_{1-3}$alkyl substituted by carboxy are also preferred.

Compounds of formula (Ia) in which $R^{11}$ represents straight or branched $C_{2-3}$alkyl (e.g. ethyl and n-propyl) substituted by $—NY^1Y^2$ are also preferred. Exemplary $—NY^1Y^2$ groups include acylamino, aryl(alkyl)amino and $—NY^1Y^2$ groups derived from 5–7 membered cyclic amines such as pyrrolidine and 2-oxo-pyrrolidine. Compounds of formula (Ia) in which $R^{11}$ represents ethyl or propyl substituted by 3-(2-oxo-pyrrolidin-1-yl), especially 3-(2-oxo-pyrrolidin-1-yl)-propyl, are preferred.

Compounds of formula (Ia) in which $X^1$ represents $CR^2$ where $R^2$ is $C_{1-4}$alky or $C_{1-4}$alkoxy (e.g. methyl or methoxy), especially methyl, are preferred.

Compounds of formula (Ia) in which $X^2$ represents $CR^2$ where $R^2$ is hydrogen or $C_{1-4}$alkoxy, especially methoxy, are also preferred.

Compounds of formula (Ia) in which Y represents carboxy are preferred.

The group $—R^9—C(=O)—N(R^{11})—CH_2—C(=O)—NR^4—CH_2—CH_2—Y$ may preferably be attached at the ring 4 position.

A preferred group of compounds of the invention are compounds of formula (Ia) in which:—$R^4$ is $C_{1-10}$alkyl, $C_{1-6}$alkyl substituted by aryl (especially 3,4-dimethoxyphenyl$C_{1-3}$alkyl), $C_{1-6}$alkyl substituted by heteroaryl (especially 3-(imidazol-1-yl)-propyl), $C_{1-6}$alkyl substituted by cycloalkyl (especially cyclopentyl- and cyclohexyl—$C_{1-3}$alkyl), $C_{1-6}$alkyl substituted by heterocycloalkyl (especially $C_{1-3}$alkyl substituted by benzodioxolyl and benzodioxanyl), $C_{1-6}$alkyl substituted by $C_{1-6}$alkoxy, $C_{1-6}$alkyl substituted by halo, $C_{1-6}$alkyl substituted by $—NY^1Y^2$, [especially (2-oxo-pyrrolidin-1-yl)propyl], or $C_{1-4}$alkenyl (e.g. allyl); $R^{11}$ represents hydrogen, $C_{1-4}$alkyl (especially methyl), $C_{1-3}$alkyl substituted by aryl (especially phenyl$C_{1-3}$alkyl), $C_{1-3}$alkyl substituted by heteroaryl (especially imidazol-1-yl$C_{1-3}$alkyl and pyridyl$C_{1-3}$alkyl), $C_{1-3}$alkyl substituted by $C_{3-8}$cycloalkyl (especially cyclohexyl$C_{1-3}$alkyl), $C_{1-3}$alkyl substituted by carboxy (especially —$(CH_2)_3CO_2H$), or $C_{2-3}$alkyl substituted by —$NY^1Y^2$ [especially (2-oxo-pyrrolidin-1-yl)propyl]; $R^9$ represents a straight or branched $C_{1-4}$alkylene chain, (preferably methylene); $X^1$ represents $CR^2$ where $R^2$ is $C_{1-4}$alkyl (especially methyl); $X^2$ represent $CR^2$ where $R^2$ is $C_{1-4}$alkoxy (e.g. methoxy); Y represents carboxy; and the group —$R^9$—C(═O)—N($R^{11}$)—$CH_2$—C(═O)—$NR^4$—$CH_2$—$CH_2$—Y is attached at the ring 4 position; and their prodrugs, and pharmaceutically acceptable salts and solvates (e.g. hydrates) of such compounds and their prodrugs.

Particular compounds of the invention are selected from the following:

3-{[({[3-methoxy-4-(3-o-tolylureido)phenyl]-acetyl}-N-methylami no)-acetyl]-[3-(2-oxo-pyrrolidin-1-yl)-prop-1-yl]-amino}-propionic acid, Compound A;

3-{[({[3-methoxy-4-(3-o-tolylureido)phenyl]-acetyl}-N-methylamino-acetyl]-[3-(3-imidazol-1-yl)prop-1-yl]-amino}-propionic acid, Compound B;

3-{(3,4-dimethoxy-benzyl)-[({[3-metloxy-4-(3-o-tolylureido)phenyl]-acetyl}-N-methylamino)-acetyl]-amino}-propionic acid. Compound C;

3-{[({[3-methoxy-4-(3-o- tolylureido)phenyl]-acetyl}-amino)-acetyl]-[3-(2-oxo-pyrrolidin-1-prop-1-yl]-amino}-propionic acid, Compound D;

3-[[2-(ethyl-m-tolyl-amino)-ethyl]-({2-[3-methoxy-4-(3-o-tolylureido)phenyl]-acetylamino}-acetyl)-amino]-propionic acid, Compound E;

3-[(2-acetylamino-ethyl)-({2-[3-methoxy-4-(3-o-tolyl ureido)phenyl]-acetylamino}-acetyl)-amino]-propionic acid, Compound F;

3-[(2-chloro-benzyl)-({2-[3-methoxy-4-(3-o-tolylureido) phenyl]-acetylamino}-acetyl)-amino]-propionic acid, Compound G;

3-[(3-methoxy-prop-1-yl)-({2-[3-methoxy-4-(3-o-tolylureido)phenyl]-acetylamino}-acetyl)-amino]-propionic acid, Compound H;

3-[cyclohexymethyl-({2-[3-methoxy-4-(3-o-tolylureido) phenyl]-acetylamino}-acetyl)-amino]-propionic acid, Compound I;

3-[(4-methoxy-benzyl)-({2-[3-methoxy-4-(3-o-tolylureido)phenyl]-acetylamino}-acetyl)-amino-]-propionic acid, Compound J;

3-[isobutyl-({2-[3-methoxy-4-(3-o-tolylureido)phenyl]-acetylamino}-acetyl)-amino]-propionic acid, Compound K;

3-[({2-[3-methoxy-4-(3-o-tolylureido)phenyl]-acetylamino}-acetyl)-(1-phenyl-ethyl)-amino]-propionic acid, Compound L;

3-{({2-[3-methoxy-4-(3-o-tolylureido)phenyl]-acetylamino}-acetyl)-[4-(5H-1,2,4-[1,2,3,]thiadiazol-4-yl)-benzyl]-amino}-propionic acid, Compound M;

3-[[1-(4-fluoro-phenyl)-ethyl]-({2-[3-methoxy-4-(3-o-tolylureido)phenyl]-acetylamino}-acetyl-amino]-propionic acid, Compound N;

3-[(2-ethoxy-benzyl)-({2-[3methoxy-4-(3-o-tolylureido) phenyl]-acetylamino}-acetyl)-amino]-propionic acid, Compound O;

3-[({2-[3-methoxy-4-(3-o-tolylureido)phenyl]-acetylamino}-acetyl)-(2-pyridin-2-yl-ethyl)-amino]-propionic acid, Compound P;

3-[[2-(3-bromo-4-methoxy-phenyl)-ethyl]-({2-[3-methoxy-4-(3-o-tolylureido)phenyl]-acetylamino}-acetyl)-amino]-propionic acid, Compound Q;

3-[(3-methoxy-benzyl)-({2-[3-methoxy-4-(3-o-tolylureido)phenyl]-acetylamino}-acetyl)-amino]-propionic acid, Compound R;

3-[(2-methoxy-ethyl)-({2-[3-metlioxy-4-(3-o-tolylureido)phenyl]-acetylamino}-acetyl)-amino]-propionic acid, Compound S;

3-[({2-[3-methoxy-4-(3-o-tolylureido)phenyl]-acetylamino}-acetyl)-(3-methyl-butyl)-amino]-propionic acid, Compound T;

3-[({2-[3-methoxy-4-(3-o-tolylureido)phenyl]-acetylamino}-acetyl)-[2-(4-phenoxy-phenyl)-ethyl]-amino}-propionic acid, Compound U;

3-[(2-benzo[1,3]dioxol-5-yl-ethyl)-({2-[3-methoxy-4-(3-tolylureido)phenyl]-acetylamino}-acetyl)-amino]-propionic acid, Compound V;

3-[butyl-({2-[3-methoxy-4-(3-o-tolylureido)phenyl]-acetylamino}-acetyl)-amino]-propionic acid, Compound W;

3-[[2-(3,5-dimethoxy-phenyl)-ethyl]-({2-[3-methoxy-4-(3-o-tolylureido)phenyl]-acetylamino}-acetyl)-amino]-propionic acid, Compound X;

3-[({2-[3-methoxy-4-(3-o-tolylureido)phenyl]-acetylamino}-acetyl)-(furan-2-y-methyl)-amino]-propionic acid, Compound Y;

3-[allyl-({2-[3-methoxy-4-(3-o-tolylureido)phenyl]-acetylamino}-acetyl )-amino]-propionic acid, Compound Z;

3-[({2-[3-methoxy-4-(3-o-tolylureido)phenyl]-acetylamino}-acetyl)-pyridin-3-ylmethyl-amino]-propionic acid, Compound AA;

3-[(3-chloro-prop-1-yl)-({2-[3-methoxy-4-(3-o-tolylureido)phenyl]-acetylamino}-acetyl)-amino]-propionic acid, Compound AB;

3-[({2-[3-methoxy-4-(3-o-tolylureido)phenyl]-acetylamino}-acetyl)-(3-phenyl-prop-1-yl)-amino]-propionic acid, Compound AC;

3-[(2-methoxyl-benzyl)-({2-[3-methoxy-4-(3-o-tolylureido)phenyl]-acetylamino}-acetyl)-amino]-propionic acid, Compound AD;

3-[({2-[3-methoxy-4-(3-o-tolylureido)phenyl]-acetylamino}-acetyl)-(2-morpholin-4yl-ethyl)-amino]-propionic acid, Compound AE;

3-[(4-methanesulfonyl-benzyl)-({2-[3-methoxy-4-(3-o-tolylureido)phenyl]-acetylamino}-acetyl)-amino] propionic acid, Compound AF;

3-[({2-[3-methoxy-4-(3-o-tolylureido)phenyl]-acetylamino}-acetyl)-methyl-amino]-propionic acid, Compound AG;

3-{({2-[3-methoxy-4-(3-o-tolylureido)phenyl]-acetylamino}-acetyl)-[2-(naphthalene-2-ylamino)-ethyl]-amino}-propionic acid, Compound AH;

3-[[2-(2,3-dimethoxy-phenyl)-ethyl]-({2-[3-methoxy-4-(3-o-tolylureido)phenyl]-acetylamino}-acetyl)-amino]-propionic acid, Compound AI;

3-[(2-diethylamino-ethyl)-({2-[3-methoxy-4-(3-o-tolylureido)phenyl]-acetylamino}-acetyl)-amino]-propionic acid, Compound AJ;

3[(1,5-dimethyl-hexyl)-({2-[3-methoxy-4-(3-o-tolylureido)phenyl]-acetylamino}-acetyl)-amino]-propionic acid, Compound AK.

3-[({2-[3-methoxy-4-(3-o-tolylureido)phenyl]-acetylamino}-acetyl)-pentyl-amino]-propionic acid, Compound AL;

3-[({2-[3-methoxy-4-(3-o-tolylureido)phenyl]-acetylamino}-acetyl)-octyl-amino]-propionic acid, Compound AM;

3-[[2-(2h-indol-3-yl)-ethyl]-({2-[3-methoxy-4-(3-o-tolylureido)phenyl]-acetylamino}-acetyl)-amino]-propionic acid, Compound AN;

3-[(2,3-dimethoxy-benzyl)-({2-[3-methoxy-4-(3-o-tolylureido)phenyl]-acetylamino}-acetyl)-amino]-propionic acid, Compound AO;

3-[({[3-methoxy-4-(3-o-tolylureido)phenyl]-acetylamino}-acetyl)-prop-1-yl-amino]-propionic acid, Compound AP;

3-[(3,3-diphenyl-prop-1-yl)-({2-[3-methoxy-4-(3-o-tolylureido)phenyl]-acetylamino}-acetyl)-amino]-propionic acid, Compound AQ;

3-[(2,2-diphenyl-ethyl)-({2-[3-methoxy-4-(3-o-tolylureido)phenyl]-acetylamino}-acetyl)-amino]-propionic acid, Compound AR;

3-[[2-(5-methoxy-2h-indol-3-yl)-ethyl]-({2-[3-methoxy-4-(3-o-tolylureido)phenyl]-acetylamino}-acetyl)-amino]-propionic acid, Compound AS;

3-[({2-[3-methoxy-4-(3-o-tolylureido)phenyl]-acetylamino}-acetyl)-(4-phenyl-butyl)-amino]-propionic acid, Compound AT;

3-[hexyl-({2-[3-methoxy-4-(3-o-tolylureido)phenyl]-acetylamino}-acetyl)-amino]-propionic acid, Compound AU;

3-[benzo[1,3]dioxol-5-ylmethyl-({2-[3-methoxy-4-(3-o-tolylureido)phenyl]-acetylamino}-acetyl)-amino]-propionic acid, Compound AV;

3-[(2-acetylamino-ethyl)-({2-[3-methoxy-4-(3-o-tolylureido)phenyl]-acetylamino}-acetyl)-amino]-propionic acid, Compound AW;

3-{({2-[3-methoxy-4-(3-o-tolylureido)phenyl]-acetylamino}-acetyl)-[2-(4-nitro-phenyl)-ethyl]-amino}-propionic acid, Compound AX;

3-[({2-[3-methoxy-4-(3-o-tolylureido)phenyl]-acetylamino}-acetyl)-(2-oxo-azepan-3-yl)-amino]-propionic acid, Compound AY;

3-[(3,5-dimethoxy-benzyl)-({2-[3-methoxy-4-(3-o-tolylureido)phenyl]-acetylamino}-acetyl)-amino]-propionic acid, Compound AZ;

3-[(3-dimethylamino-prop-1-yl)-({2-[3-methoxy-4-(3-o-tolylureido)phenyl]-acetylamino}-acetyl)-amino]-propionic acid, Compound BA;

3-[({2-[3-methoxy-4-(3-o-tolylureido)phenyl]-acetylamino}-acetyl)-naphthalen-1-ylmethyl-amino]-propionic acid, Compound BB;

3-[(1-cyclohexyl-ethyl)-({2-[3-methoxy-4-(3o-tolylureido)phenyl]-acetylamino}-acetyl)amino]-propionic acid, Compound BC;

3-[N-(3,4-dimethoxybenzyl)-2-{2-[3-methoxy-4-(3-o-tolylureido)phenyl]acetylamino}acetamido]-propionic acid, alternative name: 3-[(3,4-dimethoxy-benzyl)-({2-[3-methoxy-4-(3-o-tolylureido)-phenyl]-acetylamino}-acetyl)-amino]-propionic acid, Compound BD;

3-[(2-diethylamino-ethyl)-({2-[3-methoxy-4-(3-o-tolylureido)phenyl]-acetylamino}-acetyl)-amino]-propionic acid, Compound BE;

3-[({2-[3-methoxy-4-(3-o-tolylureido)phenyl]-acetylamino}-acetyl)-(4-nitro-benzyl)-amino]-propionic acid, Compound BF;

3-[({2-[3-methoxy-4-(3-o-tolylureido)phenyl]-acetylamino}-acetyl)-(2-piperidin-1-yl-ethyl)-amino]-propionic acid, Compound BG;

3-[benzyl-({2-[3-methoxy-4-(3-o-tolylureido)phenyl]-acetylamino}-acetyl)-amino]-propionic acid, Compound BH;

3-[cyclohexyl-({2-[3-methoxy-4-(3-o-tolylureido)phenyl]-acetylamino}-acetyl)-amino]-propionic acid, Compound BI;

3-[isobutyl-({2-[3-methoxy-4-(3-o-tolylureido)phenyl]-acetylamino}-acetyl)-amino]-propionic acid, Compound BJ;

3{(3-imidazol-1-yl-prop-1-yl)-[({[3-methoxy-4-(3-o-tolylureido)phenyl]-acetyl}-amino)-acetyl]-amino}-propionic acid, Compound BK;

3-[({2-[3-methoxy-4-(3-o-tolylureido)phenyl]-acetylamino}-acetyl)-(4-trifluoromethyl-benzyl)-amino]-propionic acid, Compound BL;

3-{({2-[3-methoxy-4-(3-o-tolylureido)phenyl]-acetylamino}-acetyl)-[2-(7-methyl-2h-indol-3-yl)-ethyl]-amino}-propionic acid, Compound BN;

3-[(4-dimethylamino-benzyl)-({2-[3-methoxy-4(3-o-tolylureido)phenyl]-acetylamino}acetyl)-amino]-propionic acid, Compound BO;

3-[isopropyl-({2-[3-methoxy-4-(3-o-tolylureido)phenyl]-acetylamino}-acetyl)-amino]-propionic acid, Compound BP;

3-[(6-chloro-2-phenoxy-phenylmethyl)-({2-[3-methoxy-4-(3o-tolylureido)phenyl]-acetylamino}-acetyl)-amino]-propionic acid, Compound BQ;

3-[({2-[3-methoxy-4-(3-o-tolylureido)phenyl]-acetylamino}-acetyl)-phenethyl-amino]-propionic acid, Compound BR;

3-[({2-[3-methoxy-4-(3-o-tolylureido)phenyl]-acetylamino}-acetyl)-(1-methyl-2-phenoxy-ethyl)-amino]-propionic acid, Compound BS;

3-[[2-(5-methoxy-2H-indol-3-yl)-ethyl]-({2-[3-methoxy-4-(3-o-tolylureido)phenyl]-acetylamino}-acetyl)-amino]-propionic acid, Compound BT;

3-[({2-[3-methoxy-4-(3-o-tolylureido)phenyl]-acetylamino}-acetyl)-(3-phenyl-prop-1-yl)-amino]-propionic acid, Compound BU;

3-{[({[3-methoxy-4-(3-o-tolylureido)phenyl]-acetyl}-prop-1-ylamino)-acetyl]-[3-(2-oxo-pyrrolidin-1-yl)-prop-1-yl]-amino}-propionic acid, Compound BV; Compounds BW to KV;

3-{[({[3-methoxy-4-(3-o-tolylureido)phenyl]-acetyl}-N-methylamino)-acetyl]-(3-carboxy-prop-1-yl)-amino}-propionic acid; Compound KW;

3-{[({[3-methoxy-4-(3-o-tolylureido)phenyl]-acetyl}-N-methylamino)-acetyl]-[2-(2-oxo-pyrrolidin-1-yl)-ethyl]-amino}-propionic acid; Compound KX;

3-{[({[3-methoxy-4-(3-o-tolylureido)phenyl]-acetyl}-amino)-acetyl]-(3-carboxy-prop-1-yl)-amino}-propionic acid; Compound LA;

3-{[({[3-methoxy-4-(3-o-tolylureido)phenyl]-acetyl}-N-methylamino)-acetyl]-[2-(2-oxo-pyrrolidin-1-yl)-ethyl]-amino}-propionic acid; Compound LB;

3-{[({[3-methoxy-4-(3-o-tolylureido)phenyl]-acetyl}-amino)-acetyl]-(2-carboxy-ethyl)-amino)}-propionic acid; Compound LC;

3-{(2,3-dimethoxy-benzyl)-[({[3-methoxy-4-(3-o-tolylureido)phenyl]-acetyl}-amino)-acetyl]-amino}-propionic acid; Compound AO;

3-{[({[3-methoxy-4-(3-o-tolylureido)phenyl]-acetyl}-amino)-acetyl]-phenyl-amino}-propionic acid; Compound LD;

3-{(3-ethoxy-4-methoxy-benzyl)-[({[3-methoxy-4-(3-o-tolylureido)phenyl]-acetyl}-amino)-acetyl]-amino}-propionic acid; Compound LE;

3-{(3,4-diethoxy-benzyl)-[({[3-methoxy-4-(3-o-tolylureido)phenyl]-acetyl}-amino)-acetyl]-amino}-propionic acid; Compound LF;

3-{(4-benzyloxy-3-methoxy -benzyl)-[({[3-methoxy-4-(3-o-tolylureido)phenyl]-acetyl}-amino)-acetyl]-amino}-propionic acid; Compound LG;

3-{[(1,4-benzodioxan-6-yl)-methyl]-[({[3-methoxy-4-(3-o-tolylureido)phenyl]-acetyl}-amino)-acetyl]-amino}-propionic acid; Compound LH;

3-{[({[3-metloxy-4-(3-o-tolylureido)phenyl]-acetyl}-amino)-acetyl]-(3-methanesulphonylamino-prop-1-yl)-amino}-propionic acid; Compound LI;

3-[(4-dimethylamino-benzyl)-[{2-[3-methoxy-4-(3-o-tolylureido)phenyl]-acetyl}-amino)-acetyl]-N-methylantino]-propionic acid;

3-{(3-nitro-benzyl)-[({[3-methoxy-4-(3-o-tolylureido)phenyl]acetyl}-amino)-acetyl]-amino}-propionic acid, Compound LJ;

3-{(2-thienylmethyl)-({[3-methoxy-4-(3-o-tolylureido)phenyl]-acetyl}-N-methylamino)-acetyl)-amino}-propionic acid, Compound LK;

3-{(2-methoxy-benzyl)-[({[3-methoxy-4-(3-o-tolylureido)phenyl]-acetyl}-N-methylamino)-acetyl]-amino}-propionic acid; Compound LL;

3-{(4-methyl-benzyl)-[({[3-methoxy-4-(3-o-tolylureido)phenyl]-acetyl}-N-methylamino)-acetyl]-amino}-propionic acid, Compound LM;

3-{(3,4-methylenedioxy-benzyl)-[({[3-methoxy-4-(3-o-tolylureido)phenyl]-acetyl}-N-methylamino)-acetyl]-amino}-propionic acid, Compound LN;

3-{(3,5-dimethoxy-benzyl)-[({[3-methoxy-4-(3-o-tolylureido)phenyl]-acetyl}-N-methylamino)-acetyl]-amino}-propionic acid, Compound LO;

3-{(2-pyridylmethyl)-[({[3-methoxy-4-(3-o-tolylureido)phenyl]-acetyl}-amino)-acetyl]-amino}-propionic acid, Compound LP;

3-{(2-furanyimethyl)-[({[3-methoxy-4-(3-o-tolylureido)phenyl]-acetyl}-N-methylamino)-acetyl]-amino}-propionic acid, Compound LQ;

3-{(2-ethoxy-benzyl)-[({[3-methoxy-4-(3-o-tolylureido)phenyl]acetyl}-N-methylamino)-acetyl]-amino}-propionic acid, Compound LR;

3-{(2-thienylmethyl)-[({[3-methoxy-4-(3-o-tolylureido)phenyl]-acetyl}-amino)-acetyl]-amino}-propionic acid, Compound LS;

3-{(4-pyridylmethyl)-[({[3-methoxy-4-(3-o-tolylureido)phenyl]-acetyl}-amino)-acetyl]-amino}-propionic acid, Compound LT;

3-{(2-pyridylmethyl)-[({[3-methoxy-4-(3-o-tolylureido)phenyl]-acetyl}-N-methylamino)-acetyl]-amino}-propionic acid, Compound LU;

3-{(3-nitro-benzyl)-[({[3-methoxy-4-(3-o-tolylureido)phenyl]-acetyl}-N-methylamino)-acetyl]-amino}-propionic acid, Compound LV;

3-{(3-pyridylmethyl)-[({[3-methoxy-4-(3-o-tolylureido)phenyl]-acetyl}-N-methylamino)-acetyl]-amino}-propionic acid, Compound LW;

3-{(4-[1,2,3-thiadiazol-4-yl]-benzyl)-[({[3-methoxy-4-(3-o-tolylureido)phenyl]-acetyl}-N-methylamino)-acetyl]-amino}-propionic acid, Compound LX;

3-{(4-pyridylmethyl)-[({[3-methoxy-4-(3-o-tolylureido)phenyl]-acetyl}-N-methylamino)-acetyl]-amino}-propionic acid, Compound LY;

3-{(benzyl)-[({[3-methoxy-4-(3-o-tolylureido)phenyl]-acetyl}-N-methylamino)-acetyl]-amino}-propionic acid, Compound LZ;

3-{(2-bromo-benzyl)-[({[3-methoxy-4-(3-o-tolylureido)phenyl]-acetyl}-N-methylamino)-acetyl]-amino}-propionic acid, Compound MA;

3-{(2-bromo-benzyl)-[({[3-methoxy-4-(3-o-tolylureido)phenyl]-acetyl}-amino)-acetyl]-amino}-propionic acid, Compound MB;

3-{(2-chloro-benzyl)-[({[3-methoxy-4-(3-o-tolylureido)phenyl]-acetyl}-N-methylamino)-acetyl]-amino}-propionic acid, Compound MC;

3-{(4-methanesulphonyl-benzyl)-[({[3-methoxy-4-(3-o-tolylureido)phenyl]-acetyl}-N-methylamino)-acetyl]-amino}-propionic acid, Compound MD;

and their prodrugs, and pharmaceutically acceptable salts and solvates (e.g. hydrates) of such compounds and their prodrugs.

Preferred compounds of the invention include:

3-{[({[3-methoxy-4-(3-o-tolylureido)phenyl]-acetyl}-N-methylamino)-acetyl]-[3-(2-oxo-pyrrolidin-1-yl)-prop-1-yl]-amino}-propionic acid, Compound A;

3-{[({[3-methoxy-4-(3-o-tolylureido)phenyl]-acetyl}-N-methylamino)-acetyl]-[3-(3-imidazol-1-yl)-prop-1-yl]-amino}-propionic acid, Compound B;

3-{(3,4-dimethoxy-benzyl)-[({[3-methoxy-4-(3-o-tolylureido)phenyl]-acetyl}-N-methylamino)-acetyl]-amino}-propionic acid, Compound C;

3-{[({[3-methoxy-4-(3-o-tolylureido)phenyl]-acetyl}-amino)-acetyl]-[3-(2-oxo-pyrrolidin-1-yl-prop-1-yl]-amino}-propionic acid, Compound D;

3-[allyl-({2-[3-methoxy-4-(3-o-tolylureido)phenyl]-acetylamino}-acetyl)-amino]-propionic acid, Compound Z;

3-[({2-[3-methoxy-4-(3-o-tolylureido)phenyl]-acetylamino}-acetyl)-(3-phenyl-prop-1-yl)-amino]-propionic acid, Compound AC;

3-[(2,3-dimethoxy-benzyl)-({2-[3-methoxy-4-(3-o-tolylureido)phenyl]-acetylamino}-acetyl)-amino]-propionic acid, Compound AO;

3-[({2-[3-methoxy-4-(3-o-tolylureido)phenyl]-acetylamino}-acetyl)-(4phenyl-butyl)-amino]-propionic acid, Compound AT;

3-[N-(3,4-dimethoxybenzyl)-2-{2-[3-methoxy-4-(3-o-tolylureido)phenyl]acetylamino}acetamido]-propionic acid, Compound BD;

3{(3-imidazol-1-yl-prop-1-yl)--[({[3-methoxy-4-(3-o-tolylureido)phenyl]-acetyl}-amino)-acetyl]-amino}-propionic acid, Compound BK;

3-[(4-dimethylamino-benzyl)-({2-[3-methoxy-4-(3-o-tolylureido)phenyl]-acetylamino}-acetyl)-amino]-propionic acid, Compound BO;

3-{[({[3-metlioxy-4-(3-o-tolylureido)phenyl]-acetyl}-N-methylamino)-acetyl]-(3-carboxy-prop-1-yl)-amino}-propionic acid; Compound KW;

3-{[({[3-methoxy-4-(3-o-tolylureido)phenyl]-acetyl}-N-methylamino)-acetyl]-[2-(2-oxo-pyrrolidin-1-yl)-ethyl-amino}-propionic acid; Compound KX;

3-{(3,4-dimethoxy-benzyl)-[({[3-methoxy-4-(3-o-tolylureido)phenyl]-acetyl}-amino)-acetyl]-amino}-propionic acid; Compound KY;

3-{[({[3-methoxy-4-(3-o-tolylureido)phenyl]-acetyl}-amino)-acetyl]-(3-carboxy-prop-1-yl)-amino}-propionic acid; Compound LA;

3-{[({[3-methoxy-4-(3-o-tolylureido)phenyl]-acetyl}-amino)-acetyl]-(2-carboxy-ethyl)-amino}-propionic acid; Compound LC;

3-{[({[3-methoxy-4-(3-o-tolylureido)phenyl]-acetyl}-amino)-acetyl]-phenyl-amino}-propionic acid; Compound LD;

3-{(3-ethoxy-4-methoxy-benzyl)-[({[3-methoxy-4-(3-o-tolylureido)phenyl]-acetyl}-amino)-acetyl]-amino}-propionic acid; Compound LE;

3-{(3,4-diethoxy-benzyl)-[({[3-methoxy-4-(3-o-tolylureido)phenyl]-acetyl}-amino)-acetyl]-amino}-propionic acid; Compound LF;

3-{(4-benzyloxy-3-methoxy-benzyl)-[({[3-methoxy-4-(3-o-tolylureido)phenyl]-acetyl}-amino)-acetyl]-amino}-propionic acid; Compound LG;

3-{[(1,4-benzodioxan-6-yl)-methyl]-[({[3-methoxy-4-(3-o-tolylureido)phenyl]-acetyl}-amino)-acetyl]-amino}-propionic acid; Compound LH;

3-{[({[3-methoxy-4-(3-o-tolylureido)phenyl]-acetyl}-amino)-acetyl]-(3-methanesulphonylamino-prop-1-yl)-amino-propionic acid; Compound LI;

3-{(3-nitro-benzyl)-[({[3-methoxy-4-(3-o-tolylureido)phenyl]-acetyl}-amino)-acetyl]-amino}-propionic acid, Compound LJ;

3-{(2-thienylmethyl)-({[3-methoxy-4-(3-o-tolylureido)phenyl]-acetyl}-N-methylamino}-acetyl)-amino}-propionic acid, Compound LK;

3-{(2-methoxy-benzyl)-[({[3-methoxy-4-(3-o-tolylureido)phenyl]-acetyl}-N-methylamino)-acetyl]-amino}-propionic acid; Compound LL;

3-{(4-methyl-benzyl)-[({[3-methoxy-4-(3-o-tolylureido)phenyl]-acetyl}-N-methylamino)-acetyl]-amino}-propionic acid, Compound LM;

3-{(3,4-methylenedioxy-benzyl)-[({[3-methoxy-4-(3-o-tolylureido)phenyl]-acetyl}-N-methylamino)-acetyl]-amino}-propionic acid, Compound LN;

3-{(3,5-dimethoxy-benzyl)-[({[3-methoxy-4-(3-o-tolylureido)phenyl]-acetyl}-N-methylamino)-acetyl]-amino}-propionic acid, Compound LO;

3-{(2-pyridylmethyl)-[({[3-methoxy-4-(3-o-tolylureido)phenyl]-acetyl}amino)-acetyl]-amino}-propionic acid, Compound LP;

3-{(2-furanylmethyl)-[({[3-methoxy-4-(3-o-tolylureido)phenyl]-acetyl}-N-methylamino)-acetyl]-amino}-propionic acid, Compound LQ;

3-{(2-ethoxy-benzyl)-[({[3-methoxy-4-(3-o-tolylureido)phenyl]-acetyl}-N-methylamino)-acetyl]-amino}-propionic acid, Compound LR;

3-{(2-thienylmethyl)-[({[3-methoxy-4-(3-o-tolylureido)phenyl]-acetyl}-amino)-acetyl]-amino}-propionic acid, Compound LS;

3-{(4-pyridylmethyl)-[({[3-methoxy-4-(3-o-tolylureido)phenyl]-acetyl}-amino)-acetyl]-amino}-propionic acid, Compound LT;

and their prodrugs, and pharmaceutically acceptable salts and solvates (e.g. hydrates) of such compounds and their prodrugs.

Especially preferred compounds of the invention include:

3-{[({[3-methoxy-4-(3-o-tolylureido)phenyl]-acetyl}-N-methylamino)-acetyl]-[3-(2-oxo-pyrrolidin-1-yl)-prop-1-yl]-amino}-propionic acid, Compound A;

3-{(3,4-dimethoxy-benzyl)-[({[3-methoxy-4-(3-o-tolylureido)phenyl]-acetyl}-N-methylamino)-acetyl]-amino}-propionic acid, Compound C;

3-{[({[3-methoxy-4-(3-o-tolylureido)phenyl]-acetyl}-amino)-acetyl]-[3-(2-oxo-pyrrolidin-1-yl)-prop-1-yl]-amino}-propionic acid, Compound D;

3-[(2,3-dimethoxy-benzyl)-({2-[3-methoxy-4-(3-o-tolylureido)phenyl]-acetylamino}-acetyl)-amino]-propionic acid, Compound AO;

3-[N-(3,4-dimethoxybenzyl)-2-{2-[3-methoxy-4-(3-o-tolylureido)phenyl]acetylamino}acetamido]-propionic acid, Compound BD;

3-{[({[3-methoxy-4-(3-o-tolylureido)phenyl]-acetyl}-N-methylamino)-acetyl]-(3-carboxy-prop-1-yl)-amino}-propionic acid; Compound KW;

3-{(3-ethoxy-4-methoxy-benzyl)-[({[3-methoxy-4-(3-o-tolylureido)phenyl]-acetyl}amino)-acetyl]-amino}-propionic acid; Compound LE;

3-{(3,4-diethoxy-benzyl)-[({[3-methoxy-4-(3-o-tolylureido)phenyl]-acetyl}-amino)-acetyl]-amino}-propionic acid; Compound LF;

and their prodrugs, and pharmaceutically acceptable salts and solvates (e.g. hydrates) of such compounds and their prodrugs.

The compounds of the invention exhibit useful pharmacological activity and accordingly are incorporated into pharmaceutical compositions and used in the treatment of patients suffering from certain medical disorders. The present invention thus provides, according to a further aspect, compounds of the invention and compositions containing compounds of the invention for use in therapy.

Compounds within the scope of the present invention block the interaction of the ligand VCAM-1 to its integrin receptor VLA-4 ($\alpha 4\beta 1$) according to tests described in the literature and described in vitro and in vivo procedures hereinafter, and which tests results are believed to correlate to pharmacological activity in humans and other mammals. Thus, in a further embodiment, the present invention provides compounds of the invention and compositions containing compounds of the invention for use in the treatment of a patient suffering from, or subject to, conditions which can be ameliorated by the administration of an inhibitor of $\alpha 4\beta 1$ mediated cell adhesion. For example, compounds of the present invention are useful in the treatment of inflammatory diseases, for example joint inflammation, including arthritis, rheumatoid arthritis and other arthritic conditions such as rheumatoid spondylitis, gouty arthritis, traumatic arthritis, rubella arthritis, psoriatic arthritis and osteoarthritis. Additionally, the compounds are useful in the treatment of acute synovitis, autoimmune diabetes, autoimmune encephalomyelitis, collitis, a therosclerosis, peripheral vascular disease, cardiovascular disease, multiple sclerosis, asthma, psoriasis restenosis, myocarditis, inflammatory bowel disease and melanoma cell division in metastasis.

A special embodiment of the therapeutic methods of the present invention is the treating of asthma.

Another special embodiment of the therapeutic methods of the present invention is the treating of joint inflammation.

Another special embodiment of the therapeutic methods of the present invention is the treating of inflammatory bowel disease.

According to a further feature of the invention there is provided a method for the treatment of a human or animal patient suffering from, or subject to, conditions which can be ameliorated by the administration of an inhibit or of the interaction of the ligand VCAM-1 to its integrin receptor VLA-4 (α4β1), for example conditions as hereinbefore described, which comprises (the administration to the patient of an effective amount of compound of the invention or a composition containing a compound of the invention. "Effective amount" is meant to describe an amount of compound of the present invention effective in inhibiting the interaction of the ligand VCAM-1 to its integrin receptor VLA-4 (α4β1), and thus producing the desired therapeutic effect.

References herein to treatment should be understood to include prophylactic therapy as well as treatment of established conditions.

The present invention also includes within its scope pharmaceutical compositions comprising at least one of the compounds of the invention in association with a pharmaceutically acceptable carrier or excipient.

Compounds of the invention may be administered by any suitable means. In practice compounds of the present invention may generally be administered parenterally, topically, rectally, orally or by inhalation, especially by the oral route.

Compositions according to the invention may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavourings, colourings, or stabilisers in order to obtain pharmaceutically acceptable preparations. The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as stareh, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilised by heating, irradiation or microfiltration.

For topical administration, gels (water or alcohol based), creams or ointments containing compounds of the invention may be used. Compounds of the invention may also be incorporated in a gel or matrix base for application in a patch, which would allow a controlled release of compound through the transdermal barrier.

For administration by inhalation compounds of the invention may be dissolved or suspended in a suitable carrier for use in a nebuliser or a suspension or solution aerosol, or may be absorbed or adsorbed onto a suitable solid carrier for use in a dry powder inhaler.

Solid compositions for rectal administration include suppositories formulated in accordance with known methods and containing at least one compound of the invention.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

The compounds according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for some patients, it will be necessary to prescribe not more than one or two doses per day.

Compounds of the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Thus, for example, compounds of formula (I), wherein $R^1$, $X^1$, $X^2$, $X^3$, $X^4$, $X^5$ and $X^6$ are as hereinbefore defined, and where the Y moiety within one of $X^3$, $X^4$ and $X^5$ is carboxy, may be prepared by hydrolysis of esters of formula (I), wherein $R^1$, $X^1$, $X^2$, $X^3$, $X^4$, $X^5$ and $X^6$ are as hereinbefore defined, and where the Y moiety within one of $X^3$, $X^4$ and $X^5$ is $—CO_2R^{12}$ group (in which $R^{12}$ is alkyl, alkenyl or arylalkyl). The hydrolysis may conveniently be carried out by alkaline hydrolysis using a base, such as an alkali metal hydroxide, e.g. lithium hydroxide, or an alkali metal carbonate, e.g. potassium carbonate, in the presence of an aqueous/organic solvent mixture, using organic solvents such as dioxan, tetrahydrofuran or methanol, at a temperature from about ambient to about reflux. The hydrolysis of the esters may also be carried out by acid hydrolysis using an inorganic acid, such as hydrochloric acid, in the presence of an aqueous/inert organic solvent mixture, using organic solvents such as dioxan or tetrahydrofuran, at a temperature from about 50° C. to about 80° C.

As another example compounds or formula (I), wherein $R^1$, $X^1$, $X^2$, $X^3$, $X^4$, $X^5$ and $X^6$ are as hereinbefore defined, and where the Y moiety within one of $X^3$, $X^4$ and $X^5$ is carboxy, may be prepared by acid catalysed removal of the tert-butyl group of tert-butyl esters of formula (I), wherein $R^1$, $X^1$, $X^2$, $X^3$, $X^4$, $X^5$ and $X^6$ are as hereinbefore defined, and where the Y moiety within one of $X^3$, $X^4$ and $X^5$ is —$CO_2R^{12}$ (in which $R^{12}$ is —$CO_2{}^tBu$), using standard reaction conditions.

In a process A compounds of formula (I), wherein $R^1$, $X^1$, $X^2$, $X^3$, $X^4$, $X^5$ and $X^6$ are as hereinbefore defined, and where the Y moiety within one of $X^3$, $X^4$ and $X^5$ is carboxy, may be prepared by coupling of an acid (or an acid halide) with an amine to give an amide bond within $R^3$ using standard peptide coupling procedures as described hereinafter.

As an example of process A, compounds of formula (I), wherein $R^1$, $X^1$, $X^2$, $X^3$, $X^4$, $X^5$ and $X^6$ are as hereinbefore defined, and where the Y moiety within one of $X^3$, $X^4$ and $X^5$ is carboxy, may be prepared by:

(i) treating Wang resin (4-hydroxymethylphenoxylated styrene/divinylbenzene copolymer) with acryloyl chloride, in the presence of a tertiary amine, such as diisopropylethylamine, in an inert solvent, such as dichloromethane, at a temperature at about room temperature, to give Resin A:

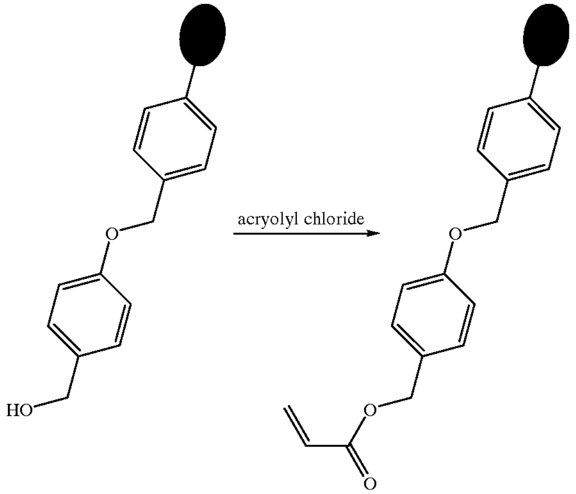

(Wang Resin) (Resin A)

where

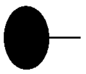

represents the polymeric core comprising polystyrene crosslinked with 1% to 2% divinylbenzene.

(ii) reaction of Resin A with amines of formula (II), wherein $R^4$ is as defined hereinbefore, in the presence of a base, such as a tertiary organic base, for example diisopropylethylamine, in dimethylformamide an at a temperature at about room temperature, to give Resin 1, in which $R^4$ and

are as defined hereinbefore:

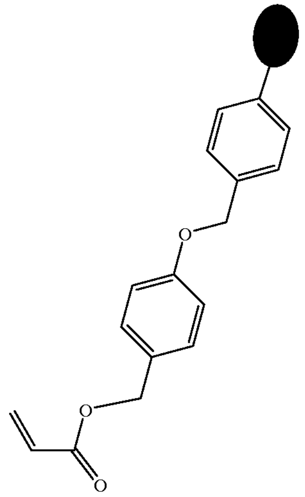

(Resin A)

\+ $R^4$—$NH_2$ (II)

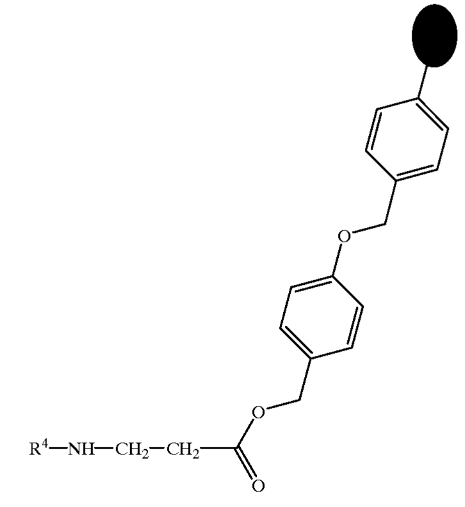

(Resin 1)

(iii) reaction of Resin 1 with compounds of formula (III)

(III)

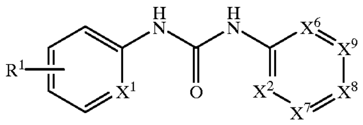

wherein $R^1$, $X^1$, $X^2$ and $X^6$ are as hereinbefore defined, one of $X^7$, $X^8$ and $X^9$ represents $CR^{14}$ [in which $R^{14}$ is —$L^1$—$(CH_2)_n$—$CO_2H$ (in which $L^1$ and n are as hereinbefore defined)], and the others independently represent N or $CR^2$ (in which $R^2$ is as hereinbefore defined), in the presence of O-(7-azabenzotriazol-1-yl)-1,1,3,3-tetramethyluronium hexafluorophosphate and diisopropylethylamine in dimethylformamide, at room temperature, to give resin 2 wherein $R^4$, $R^9$, n and

are as hereinbefore defined and $R^{15}$ represents a monovalent radical derived from (III) in which $R^1$, $X^1$, $X^2$ and $X^6$ are as hereinbefore defined, one of $X^7$, $X^8$ and $X^9$ represents CH and the others independently represent N or $CR^2$ (in which $R^2$ is as hereinbefore defined) by removing one of the hydrogen atoms from $X^7$, $X^8$ or $X^9$:

(Resin 2)

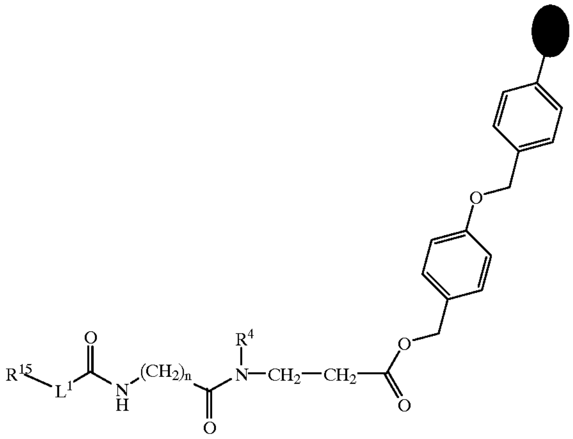

(iv) Resin 2 may then be treated with trifluoroacetic acid in an inert solvent such as dichioromethane and at a temperature at about room temperature.

As another example of process A, compounds of formula I, wherein $R^1$, $X^1$, $X^2$, $X^3$, $X^4$, $X^5$ and $X^6$ are as hereinbefore defined, and where the $L^1$ and Y moieties within one of $X^3$, $X^4$ and $X^5$ are —$R^9$—C(=O)—NH— (where $R^9$ is as hereinbefore defined) and carboxy respectively, may be prepared by:

(i) treating Resin 1, wherein $R^4$ and

are as hereinbefore defined, with a suitably protected amino-acid of formula (IV), wherein $R^{13}$ is a suitable amino protecting group (such as 9-fluorenylmethoxycarbonyl, FMOC) and n is as hereinbefore defined, in the presence of O-(7-azabenzotriazol-1-yl)-1,1,3,3-tetramethyluronium hexafluorophosphate and diisopropylethylamine in dimethylformamide, at room temperature to give Resin 3, wherein $R^4$ and

are as hereinbefore defined:

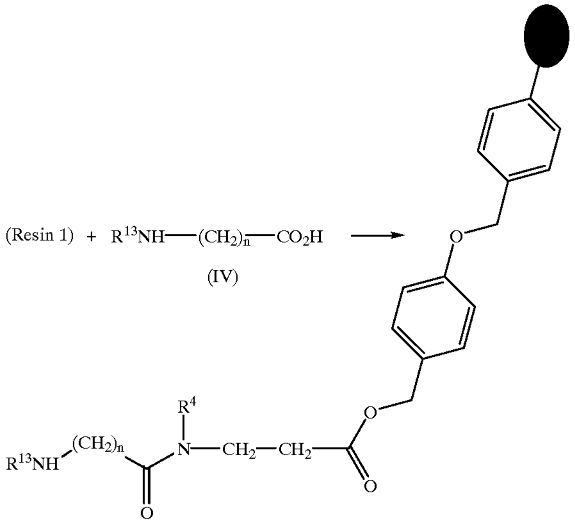

(Resin 3)

(ii) The resulting Resin 3, may then be deprotected, for example by tetreating with piperidine in dimethylformamide, at room temperature, to give Resin 4, wherein $R^4$, n and

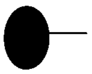

are as hereinbefore defined:

(Resin 4)

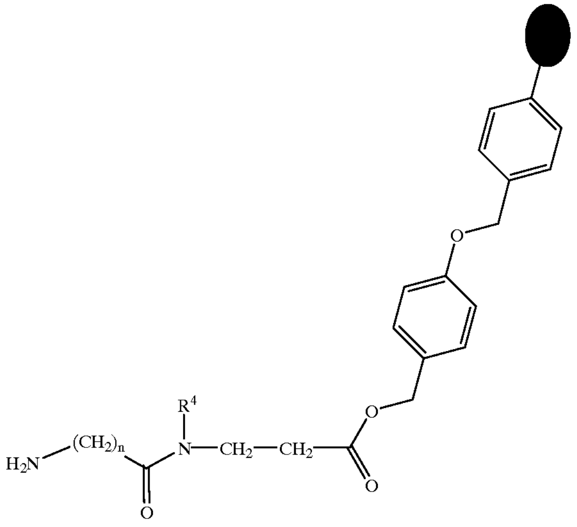

(iii) Resin 4 may then be treated with compounds of general formula (III), wherein $R^1$, $X^1$, $X^2$ and $X^6$ are as hereinbefore defined, one of $X^7$, $X^8$ and $X^9$ represents $CR^{14}$ [in which $R^{14}$ is —$R^9$—$CO_2H$ (where $R^9$ is as hereinbefore defined)], and the others independently represent N or $CR^2$ (in which $R^2$ is as hereinbefore defined), using standard peptide coupling procedures, for example those described hereinabove, to give resin 5, wherein $R^4$, $R^9$, $R^{15}$, n and

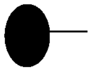

are as hereinbefore defined:

(Resin 5)

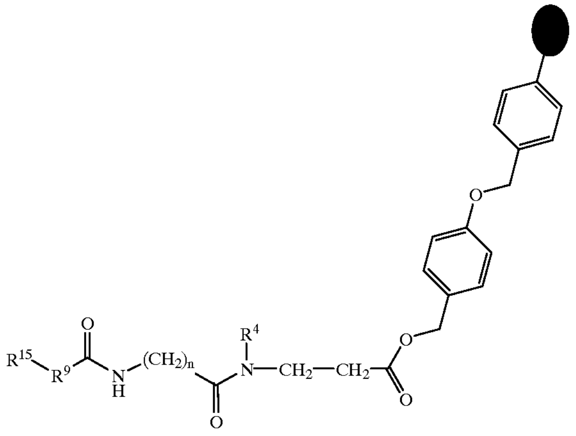

(iv) Resin 5 may then be treated with trifluoroacetic acid in an inert solvent such as dichloromethane and at a temperature at about room temperature.

As another example of process A, compounds of formula (I), wherein $R^1$, $X^1$, $X^2$, $X^3$, $X^4$, $X^5$ and $X^6$ are as hereinbefore defined, and where the $L^1$ and Y moieties within one of $X^3$, $X^4$ and $X^5$ are —$R^9$—C(=O)—($NR^{11}$)— (where $R^9$ and $R^{11}$ is as hereinbefore defined) and carboxy respectively, may be prepared by:

(i) treating Resin 1, wherein $R^4$ and

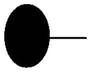

are as hereinbefore defined, with compounds of formula (V), wherein n is as hereinbefore defined and $X^{10}$ is a halogen atom, preferably bromine, using standard peptide coupling procedures, for example those described hereinabove, to give Resin 6:

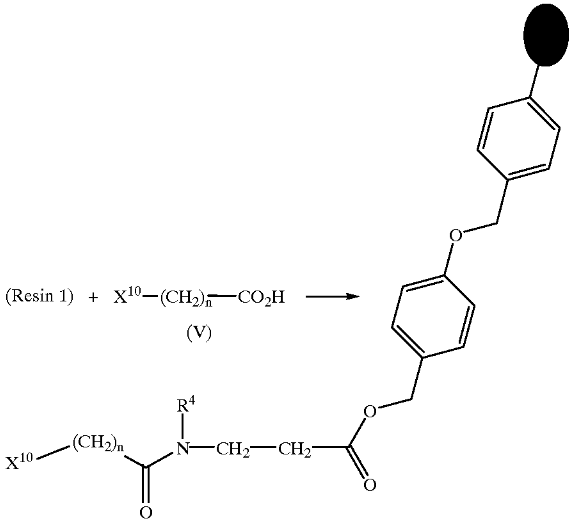

(Resin 6)

(ii) Reaction of Resin 6 with amines of formula (VI), wherein $R^{11}$ is as hereinbefore defined, in an inert solvent such as dimethyl sulphoxide, and at a temperature at about 80° C. to give Resin 7, wherein $R^4$, $R^{11}$, and

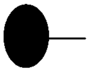

are as hereinbefore defined:

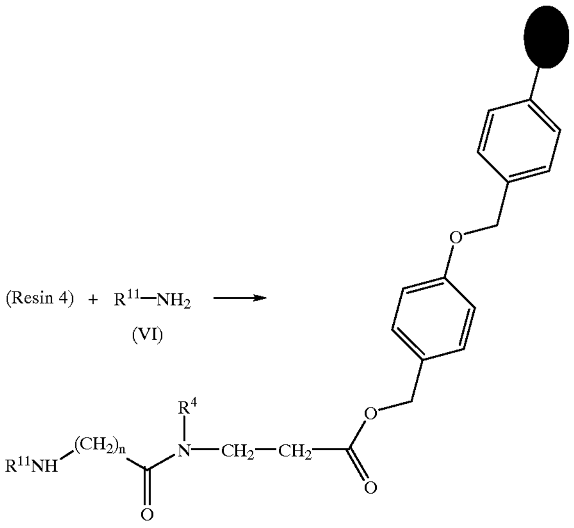

(Resin 7)

(iii) Resin 7 may then be treated with compounds of general formula (III), wherein $R^1$, $X^1$, $X^2$ and $X^6$ are as hereinbefore defined, one of $X^7$, $X^8$ and $X^9$ represents $CR^{14}$ [in which $R^{14}$ is —$R^9$ —$CO_2H$ (where $R^9$ is as hereinbefore defined)], and the others independently represent N or $CR^2$ (in which $R^2$ is as hereinbefore defined), using standard peptide coupling procedures, for example those described hereinabove, to give resin 8 wherein $R^4$, $R^9$, $R^{11}$, $R^{15}$ n and

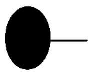

are as hereinbefore defined:

(Resin 8)

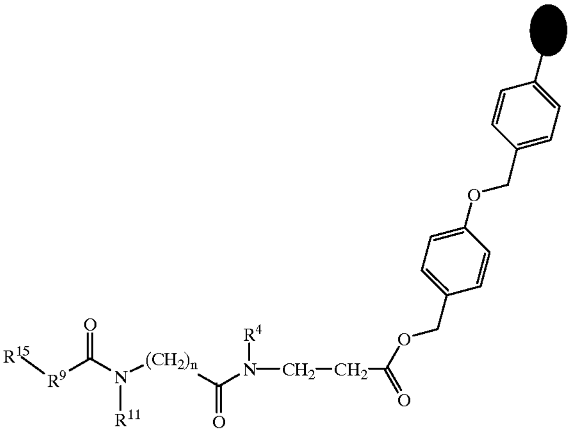

(iv) Resin 8 may then be treated with trifluoroacetic acid in an inert solvent such as dichloromethane and at a temperature at about room temperature.

Esters of formula (I), wherein $R^1$, $X^1$, $X^2$, $X^3$, $X^4$, $X^5$ and $X^6$ are as hereinbefore defined and where Y moiety within one of $X^3$, $X^4$ and $X^5$ is a —$CO_2R^{12}$ group (in which $R^{12}$ is as hereinbefore defined), may be prepared by reaction of compounds of formula (III), wherein $R^1$, $X^1$, $X^2$ and $X^6$ are as hereinbefore defined, one of $X^7$, $X^8$ and $X^9$ represents C-$R^{14}$ [in which $R^{14}$ is —$L^1$—$(CH_2)_n$—C(=O)$X^{11}$ (where $L^1$ and n are as hereinbefore defined and $X^{11}$ is a hydroxy group, or a halogen, preferably chlorine, atom)] and the others independently represent N or $CR^2$ (where $R^2$ is as hereinbefore defined), with amines of formula (VII):

$$R^4—HN—CH_2—CH_2—CO_2R^{12} \quad (VII)$$

wherein $R^4$ and $R^{12}$ are as hereinbefore defined. When $X^{11}$ is a hydroxy group the reaction may be carried out using standard peptide coupling procedures as described hereinbefore. When $X^{11}$ is a halogen atom the reaction may be carried out with the aid of a base, such pyridine, preferably in a solvent such as tetrahydrofuran and at a temperature at about room temperature.

According to a further process B compounds of the invention may be prepared by interconversion of other compounds of the invention.

For example compounds of formula (I) wherein $R^1$, $X^1$, $X^2$, $X^3$, $X^4$, $X^5$ and $X^6$ are as hereinbefore defined, and where the Y moiety within one of $X^3$, $X^4$ and $X^5$ is —C(=O)—NHOH, may be prepared by reaction of compounds of formula (I), wherein $R^1$, $X^1$, $X^2$, $X^3$, $X^4$, $X^5$ and $X^6$ are as hereinbefore defined, and where the Y moiety within one of $X^3$, $X^4$ and $X^5$ is carboxy, with hydroxylamine using standard peptide coupling procedures such as treatment with a carbodiimide, for example dicyclohexylcarbodiimide, in the presence of triethylamine, in an inert solvent such as dichloromethane or tetrahydrofuran and at a temperature at about room temperature. The coupling may also be carried out using 1-hiydroxybenzotriazole and 1-(3-dimethylamiinopropyl)-3-ethylcarbodiimide in dichilorometliane at room temperature. The preparation may also be carried out using an O-protected hiydroxylamine such as O-(trimethylsilyl) hydroxylamine, O-(t-butyldimethylsilyl)-hydroxylamine, or O-(tetrahydropyranyl)hydroxylamine followed by treatment with acid.

As another example of the interconversion process, compounds of formula (I) containing sulphioxide linkages may be prepared by the oxidation of corresponding compounds containing —S— linkages. For example, the oxidation may conveniently be carried out by means of reaction with a peroxyacid, e.g. 3-chloroperbenzoic acid, preferably in an inert solvent, e.g. dichloromethane, preferably at or near room temperature, or alternatively by means of potassium hydrogen peroxomonosulphate in a medium such as aqueous methanol, buffered to about pH5, at temperatures between about 0° C. and room temperature. This latter method is preferred for compounds containing an acid-labile group.

As another example of the interconversion process, compounds of formula (I) containing sulphone linkages may be prepared by the oxidation of corresponding compounds containing —S— or sulphoxide linkages. For example, the oxidation may conveniently be carried out by means of reaction with a peroxyacid, e.g. 3-chloroperbenzoic acid, preferably in an inert solvent, e.g. dichloromethane, preferably at or near room temperature.

It will be appreciated that compounds of the present invention may contain asymmetric centres. These asymmetric centres may independently be in either the R or S configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds of formula (I) hereinabove. Such isomers can be separated from their mixtures, by the application or adaptation of known methods, for example chromatographic techniques and recrystallisation techniques, or they are separately prepared from the appropriate isomers of their intermediates.

According to a further feature of the invention, acid addition salts of the compounds of this invention may be prepared by reaction of the free base with the appropriate acid, by the application or adaptation of known methods. For example, the acid addition salts of the compounds of this invention may be prepared either by dissolving the free base in water or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

Compounds of this invention can be regenerated from their base addition salts by the application or adaptation of known methods. For example, parent compounds of the invention can be regenerated from their base addition salts by treatment with an acid, e.g. hydrochloric acid.

Compounds of the present invention may be conveniently prepared, or formed during the process of the invention, as solvates (e.g. hydrates). Hydrates of compounds of the present invention may be conveniently prepared by recrystallisation from an aqueous/organic solvent mixture, using organic solvents such as dioxan, tetrahydrofuran or methanol.

According to a further feature of the invention, base addition salts of the compounds of this invention may be prepared by reaction of the free acid with the appropriate base, by the application or adaptation of known methods. For example, the base addition salts of the compounds of this invention may be prepared either by dissolving the free acid in water or aqueous alcohol solution or other suitable solvents containing the appropriate base and isolating the salt by evaporating the solution, or by reacting the free acid and base in an organic solvent, in which case the salt separates directly or can be obtained by concentration of the solution.

The starting materials and intermediates may be prepared by the application or adaptation of known methods, for example methods as described in the Reference Examples or their obvious chemical equivalents.

Compounds of formula (III), wherein $R^1$, $X^1$, $X^2$ and $X^6$ are as hereinbefore defined, one of $X^7$, $X^8$ and $X^9$ represents C-$R^{14}$ (in which $R^{14}$ is as described hereinabove, or a suitably protected derivative thereof) and the others independently represent N or $CR^{10}$ (where $R^{10}$ is as hereinbefore defined), maybe prepared by the application or adaptation of methods described in prepared as described in the specification of International Patent Application Publication No. WO 96/22966.

Intermediates of formulae (Resin 1), (Resin 2), (Resin 3), (Resin 4), (Resin 5), (Resin 6), (Resin 7) and (Resin 8) are novel compounds and, as such, they and their processes described herein for their preparation constitute further features of the present invention.

The present invention is further Exemplified but not limited by the following illustrative Examples and Reference Examples.

In the nuclear magnetic resonance spectra (NMR) the chemical shifts are expressed in ppm relative to tetramethylsilane. Abbreviations have the following significances: s=singlet; d=doublet; t=triplet; m=multiplet; dd=doublet of doublets; b=broad.

Mass spectra (MS) were recorded on a Micromass Platform II mass spectrometer fitted with an Electrospray source and an HP1100 liquid chromatograph; using a mixture of acetonitrile and water (1:1, v/v) as the mobile phase, a flow rate of 0.3 ml/minute, an injection volume of 20 $\mu$l, a run time of 2.0 minutes, a scan range of 150–850 Daltons Positive/Negative, a scan time of 2.0 seconds, an ESI voltage of 3.5 Kv, an ESI pressure of 20 n/m2 Nitrogen. Abbreviations have the following significances: w=weak.

EXAMPLE 1

Compounds A, B and C

A solution of ({[3-methoxy-4-(3-o-tolylureido)phenyl]-acetyl}-N-methylamino)-acetic acid [0.80 g, Reference Example 1] and 3-[3-(2-oxo-pyrrolidin-1-yl)-prop-l1ylamino]-propionic acid ethyl ester (0.51 g, Reference Example 2(c)] in dimethylformamide (25 ml) was treated with [O-(7-azabenzotriazol-1-yl)-1,1,3,3,-tetramethyluronium hexafluorophosphate (0.80 g) and diisopropylethylamine (0.75 ml). After stirring at room temperature for 2 hours the reaction mixture was treated with water (100 ml) then extracted three times with ethyl acetate. The combined organic extracts were washed with hydrochloric acid (1M), then with brine, then dried over magnesium sulphate and then evaporated. The residual oil was subjected to flash chromatography on silica eluting with a mixture of dichloromethane and methanol (25:1, v/v) to give 3-{[({[3-methoxy-4-(3-o-tolylureido)phenyl]-acetyl}-N-methylamino)-acetyl]-[3-(2-oxo-pyrrolidin-1-yl)-prop-1-yl]-amino}-propionic acid ethyl ester as a colourless oil (0.76 g). The ester was dissolved in tetrahydrofuran (50 ml) and then treated with lithium hydroxide hydrate (0.065 g) in water (10 ml). After stirring at room temperature for 2 hours the mixture was concentrated to remove the tetrahydrofuran. The residual aqueous residue was washed with ethyl acetate then acidified by addition of hydrochloric acid (1M) and then extracted three times with dichloromethane. The combined organic extracts were washed with brine, then dried over magnesium sulphate and then evaporated to give 3-{[({[3-methoxy-4-(3-o-tolylureido)phenyl]-acetyl}-N-methylamino)-acetyl]-[3-(2-oxo-pyrrolidin-1-yl)-prop-1-yl]-amino}-propionic acid as a white solid (0.58 g, Compound A), m.p.73–76° C. [Elemental analysis:- C,60.69; H,6.85; N,11.79% Calculated for $C_{30}H_{39}N_5O_7.0.67H_2O$:- C,60.69; H,6.69; N,11.58%]. MS: 580 $[MH]^-$. HPLC: $R_T$=9.72 minutes (gradient elution using a mixture of acetonitrile and water 1:4 to 4:1).

(b) By proceeding in a manner similar to Example 1(a) but using 3-(3-imidazol-1-yl-prop-1-ylamino)-propionic acid ethyl ester [Reference Example 2(b)] there was prepared 3-{[({[3-methoxy-4-(3-o-tolylureido)phenyl]-acetyl}-N-methylamino)-acetyl-]-[3-(3-imidazol-1-yl)-prop-1-yl]-amino}-propionic acid as a white solid (Compound B), m.p. 58–62° C. MS: 563 $[MH]^-$. HPLC: $R_T$=9.70 minutes (gradient caution using a mixture of acetonitrile and water 1:4 to 4:1).

(c) By proceeding in a manner similar to Example 1(a) but using 3-(3,4-dimethoxy-benzylamino)-propionic acid ethyl ester [Reference Example 2(a)] there was prepared 3-{(3,4-dimethoxy-benzyl)-[({[3-methoxy-4-(3-o-tolylureido)phenyl]-acetyl}-N-methylamino)-acetyl]-amino}-propionic acid as a white solid (Compound C), m.p. 104–106° C. [Elemental analysis:- C,62.19; H,6.43; N,8.94% Calculated for $C_{32}H_{38}N_4O_8.0.67H_2O$:- C,62.13; H,6.40; N,9.05%].

MS: 605 $[MH]^-$. HPLC: $R_T$=11.92 minutes (gradient elution using a mixture of acetonitrile and water 1:4 to 4:1).

EXAMPLE 2

Compounds D to BU

Step 1. Wang resin (3.0 g, 0.92 mmol/g) was allowed to swell in dichloromethane (30 ml) for 15 minutes, then treated with diisopropylethylamine (1.8 ml) followed by acryloyl chloride (0.9 ml). The mixture was kept at room temperature for 3 hours with occasional gentle shaking then filtered to give resin A which was washed (i) three times with dichloromethane (15 ml), (ii) three times with methanol (15 ml), (iii) three times with dimethylformamide (15 ml), (iv) three times with methanol (15 ml), (v) three times with dichloromethane (15 ml) and then dried in a desiccator under high vacuum for 2 hours.

Step 2. Resin A (40 mg) was placed in a Jones tube, suspended in dimethylformamide (1 ml) and then treated with 1-(3-aminopropyl-1-yl)-2-pyrrolidinone (50 mg). After standing at room temperature for 90 minutes the mixture was filtered to give resin B which was washed (i) four times with dimethylformamide (5 ml), (ii) three times with methanol (5 ml), (iii) dimethylformamide (5 ml).

Step 3. Resin B from step 2 was treated with a solution of ({[3-methoxy-4-(3-o-tolylureido)phenyl]-acetyl}-amino]- acetic acid (30 mg, Reference Example 3) in dimethylformamide (1 ml), and then with a solution of [O-(7-azabenzotriazol-1-yl)-1,1,3,3,-tetramethyluronium hexafluorophosphate] (30 mg) in dimethylformamide (1 ml) and diisopropylethylamine (30 $\mu$l). After standing at room temperature for 3 hours with occasional agitation the mixture was filtered to give resin C which was washed (i) four times with dimethylformamide (5 ml), (ii) three times with methanol(5 ml), (iii) four times with dichloromethane (45 ml) and then dried in a desiccator under vacuum for 2 hours.

Step 4. Resin C from step 3 was treated with a mixture of dichloromethane and trifluoroacetic acid (2 ml, 1:1 v/v). After standing at room temperature for 45 minutes the mixture was filtered, and the resin was washed with dichloromethane. The combined filtrate and washing were evaporated to give 3-{[({[3-methoxy-4-(3-o-tolylureido)phenyl]-acetyl}-amino)-acetyl]-[3-(2-oxo-pyrrolidin-1-yl)-prop-1-yl]-amino}-propionic acid (Compound D). MS: 568 $[MH]^+$. HPLC: $R_T$=3.11 minutes, area of main peak as a percentage of the total sample =96% (gradient elution using a mixture of acetonitrile and water 3:7 to 17:3 v/v).

By proceeding in a similar manner to Example 2, but using the appropriately substituted amines in step 2, there were prepared Compounds E to BU depicted in Table 1.

TABLE 1

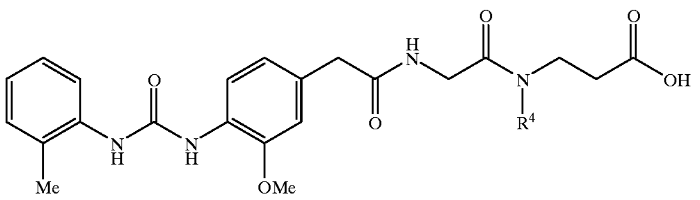

| Compound number | $R^4$ | MOLECULAR FORMULA | HPLC $R_T$ | $MH^+$ | $MH^-$ |
|---|---|---|---|---|---|
| Compound E | 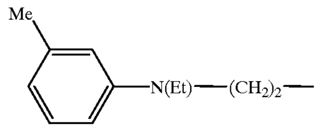 | $C_{33}H_{41}N_5O_6$ | 4.5, 95% | 604 | |
| Compound F | $CH_3C(=O)NH—(CH_2)_2—$ | $C_{26}H_{33}N_5O_7$ | 2.7, 86% | 528 | 526 |
| Compound G | 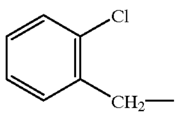 | $C_{29}H_{31}ClN_4O_6$ | 5.4, 93% | 567 | 565 |
| Compound H | $MeO—(CH_2)_3$ | $C_{26}H_{34}N_4O_7$ | 3.6, 96% | 515 | 513 |
| Compound I | 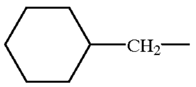 | $C_{29}H_{38}N_4O_6$ | 5.7, 98% | 539 | 537 |
| Compound J | 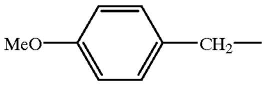 | $C_{30}H_{34}N_4O_7$ | 5.0, 85% | 563 | 561 |
| Compound K | $(CH_3)_2CH—CH_2—$ | $C_{26}H_{34}N_4O_6$ | 4.6, 92% | 499 | 497 |
| Compound L | 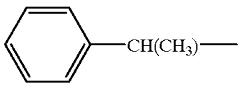 | $C_{30}H_{34}N_4O_6$ | 5.2, 82% | 547w | 545 |
| Compound M | 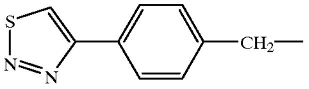 | $C_{31}H_{32}N_6O_6S$ | 7.7, 60% | 617w | 615 |
| Compound N | 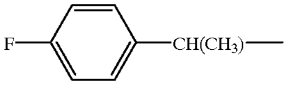 | $C_{30}H_{33}FN_4O_6$ | 8.0, 81% | 565 | 563 |

TABLE 1-continued
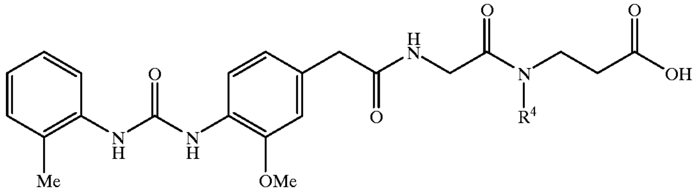
| Compound number | $R^4$ | MOLECULAR FORMULA | HPLC $R_T$ | $MH^+$ | $MH^-$ |
|---|---|---|---|---|---|
| Compound O | 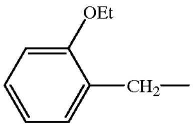 | $C_{31}H_{36}N_4O_7$ | 5.6, 97% | | |
| Compound P | 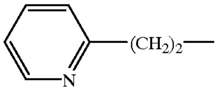 | $C_{29}H_{33}N_5O_6$ | 2.7, 96% | 548 | 546 |
| Compound Q | 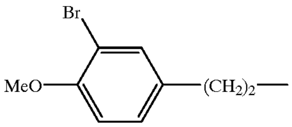 | $C_{31}H_{35}N_4BrO_7$ | 5.8, 95% | 657 | 655 |
| Compound R | 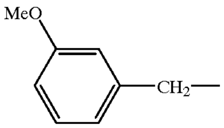 | $C_{30}H_{34}N_4O_7$ | 5.0, 89% | 563 | 561 |
| Compound S | $MeO-(CH_2)_2-$ | $C_{25}H_{32}N_4O_7$ | 3.5, 94% | 501 | 499 |
| Compound T | $(CH_3)_2CH-(CH_2)_2-$ | $C_{27}H_{36}N_4O_6$ | 5.2, 90% | 513 | 511 |
| Compound U | 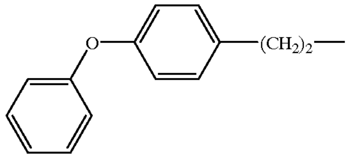 | $C_{36}H_{38}N_4O_7$ | 7.0, 86% | 639 | 637 |
| Compound V | 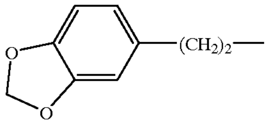 | $C_{31}H_{34}N_4O_8$ | 7.8, 68% | 591 | 589 |
| Compound W | $CH_3-(CH_2)_3-$ | $C_{26}H_{34}N_4O_6$ | 4.7, 97% | 499 | 497 |
| Compound X | 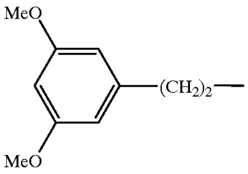 | $C_{32}H_{38}N_4O_8$ | 5.4, 88% | 607 | 605 |
| Compound Y | 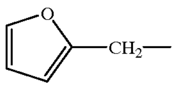 | $C_{27}H_{30}N_4O_7$ | 4.5, 95% | 523 | 521 |
| Compound Z | $CH_2{=}CH-CH_2-$ | $C_{25}H_{30}N_4O_6$ | 3.9, 97% | 483 | 481 |

TABLE 1-continued

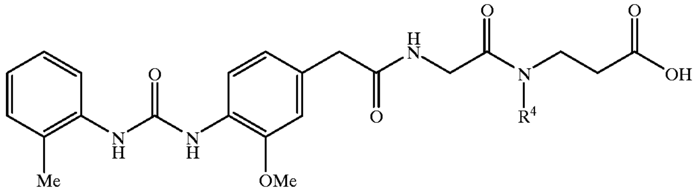

| Compound number | $R^4$ | MOLECULAR FORMULA | HPLC $R_T$ | $MH^+$ | $MH^-$ |
|---|---|---|---|---|---|
| Compound AA | 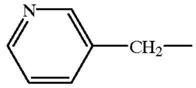 | $C_{28}H_{31}N_5O_6$ | 2.6, 95% | 534 | 532 |
| Compound AB | $Cl—(CH_2)_3—$ | $C_{25}H_{31}ClN_4O_6$ | 4.5, 95% | 519 | 517 |
| Compound AC | 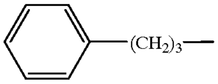 | $C_{31}H_{36}N_4O_6$ | 5.7, 88% | 561 | 559 |
| Compound AD | 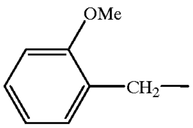 | $C_{30}H_{34}N_4O_7$ | 5.1, 83% | 563 | 561 |
| Compound AE | 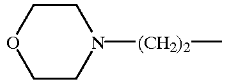 | $C_{28}H_{37}N_5O_7$ | 2.6, 91% | 556 | 554 |
| Compound AF | 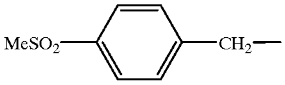 | $C_{30}H_{34}N_4O_8S$ | 6.4, 76% | 611 | 609 |
| Compound AG | $CH_3—$ | $C_{23}H_{28}N_4O_6$ | 3.2, 89% | | 455 |
| Compound AH | 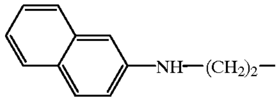 | $C_{34}H_{37}N_5O_6$ | 5.9, 97% | 612 | 610 |
| Compound AI | 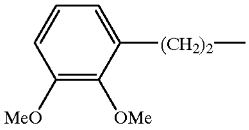 | $C_{32}H_{38}N_4O_8$ | 5.3, 96% | 607 | 605 |
| Compound AJ | $Et_2N—(CH_2)_2—$ | $C_{28}H_{39}N_5O_6$ | 3.0, 96% | 542 | 540 |
| Compound AK | $(CH_3)_2CH—(CH_2)_3—CH(CH_3)—$ | $C_{30}H_{42}N_4O_6$ | 5.3, 96% | 555 | 553 |
| Compound AL | $CH_3—(CH_2)_4—$ | $C_{27}H_{36}N_4O_6$ | 5.2, >90% | 513 | 511 |
| Compound AM | $CH_3—(CH_2)_7—$ | $C_{30}H_{42}N_4O_6$ | 7.4, 93% | 555 | 553 |
| Compound AN | 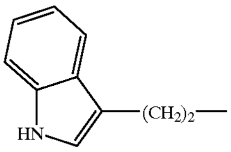 | $C_{32}H_{35}N_5O_6$ | 5.1, 67% | 586 | 584 |

TABLE 1-continued
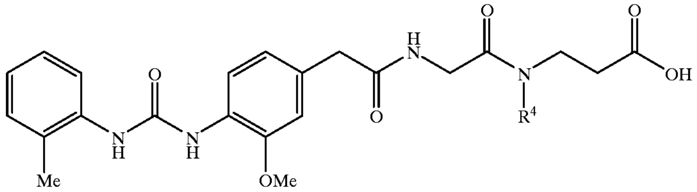
| Compound number | $R^4$ | MOLECULAR FORMULA | HPLC $R_T$ | $MH^+$ | $MH^-$ |
|---|---|---|---|---|---|
| Compound AO | 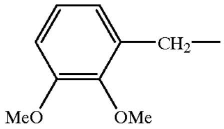 | $C_{31}H_{36}N_4O_8$ | 7.6, 79% | 593 | 591 |
| Compound AP | $CH_3$—$(CH_2)_2$ | $C_{25}H_{32}N_4O_6$ | 4.1, 98% | 485 | 483 |
| Compound AQ | 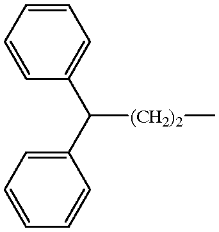 | $C_{37}H_{40}N_4O_6$ | 6.9, 96% | 637 | 635 |
| Compound AR | 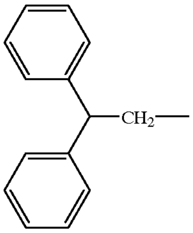 | $C_{36}H_{38}N_4O_6$ | 6.4, 96% | 623 | 621 |
| Compound AS | 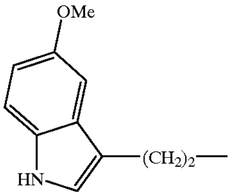 | $C_{33}H_{37}N_5O_7$ | 5.0, 82% | 616 | 614 |
| Compound AT | 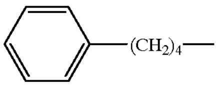 | $C_{32}H_{38}N_4O_6$ | 6.2, 95% | 575 | 573 |
| Compound AU | $CH_3$—$(CH_2)_5$— | $C_{28}H_{38}N_4O_6$ | 6.0, >90% | 527 | 525 |
| Compound AV | 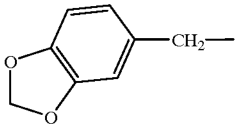 | $C_{30}H_{32}N_4O_8$ | 4.9, 88% | 577 | 575 |
| Compound AW | $CH_3C(=O)NH$—$(CH_2)_2$— | $C_{26}H_{33}N_5O_7$ | 1.8, 67% | 528 | 526 |

TABLE 1-continued
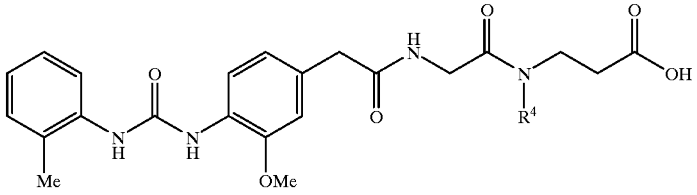
| Compound number | $R^4$ | MOLECULAR FORMULA | HPLC $R_T$ | $MH^+$ | $MH^-$ |
|---|---|---|---|---|---|
| Compound AX | 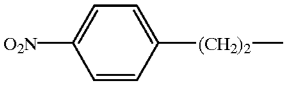 | $C_{30}H_{33}N_5O_8$ | 7.9, 74% | 592 | 590 |
| Compound AY | 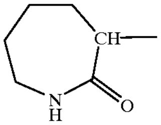 | $C_{28}H_{35}N_5O_7$ | 3.3, >95% | 554 | 552 |
| Compound AZ | 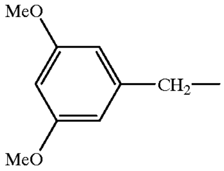 | $C_{31}H_{36}N_4O_8$ | 5.2, 76% | 593 | 591 |
| Compound BA | $Me_2N—(CH_2)_3—$ | $C_{27}H_{37}N_5O_6$ | 2.6, 93% | 528 | 526 |
| Compound BB | 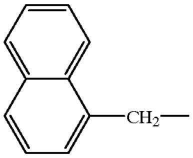 | $C_{33}H_{34}N_4O_6$ | 6.0, 74% | 583 | 581 |
| Compound BC | 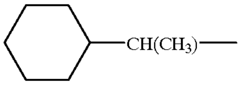 | $C_{30}H_{40}N_4O_6$ | 6.0, 95% | 553 | 552 |
| Compound BD | 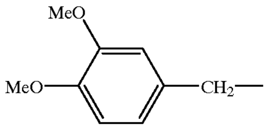 | $C_{31}H_{36}N_4O_8$ | 4.7, 87% | 593 | 591 |
| Compound BE | $Et_2N—(CH_2)_2—$ | $C_{28}H_{39}N_5O_6$ | 1.9, 83% | 542 | 540 |
| Compound BF | 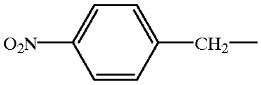 | $C_{29}H_{31}N_5O_8$ | 7.7, 76% | 578 | 576 |
| Compound BG | 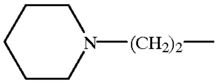 | $C_{29}H_{39}N_5O_6$ | 3.1, 97% | 554 | 552 |
| Compound BH | 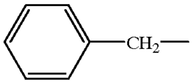 | $C_{29}H_{32}N_4O_6$ | 5.0, 96% | 533 | 531 |

TABLE 1-continued
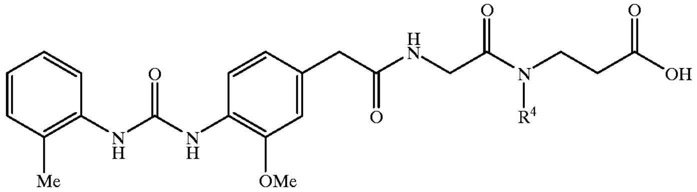
| Compound number | $R^4$ | MOLECULAR FORMULA | HPLC $R_T$ | $MH^+$ | $MH^-$ |
|---|---|---|---|---|---|
| Compound BI | 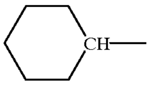 | $C_{28}H_{36}N_4O_6$ | 5.0, 97% | 525 | 523 |
| Compound BJ | $(CH_3)_2CH—CH_2—$ | $C_{26}H_{34}N_4O_6$ | 4.6, 95% | 499 | 497 |
| Compound BK | 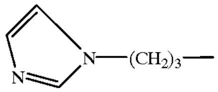 | $C_{28}H_{34}N_6O_6$ | 2.6, 98% | 551 | 549 |
| Compound BL | 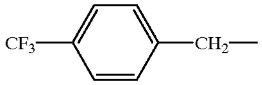 | $C_{30}H_{31}F_3N_4O_6$ | 6.0, 83% | 601 | 599 |
| Compound BN | 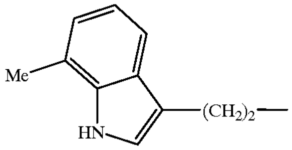 | $C_{33}H_{37}N_5O_6$ | 8.6, 58% | | 598 |
| Compound BO | 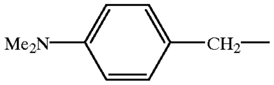 | $C_{31}H_{37}N_5O_6$ | 1.8, 83% | 576 | 574 |
| Compound BP | $(CH_3)_2—CH—$ | $C_{25}H_{32}N_4O_6$ | 3.9, 95% | 485 | 483 |
| Compound BQ | 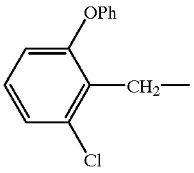 | $C_{35}H_{35}ClN_4O_7$ | 6.7, 88% | 659 | 657 |
| Compound BR | 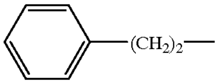 | $C_{30}H_{34}N_4O_6$ | 5.2, 93% | 547 | 545 |
| Compound BS | 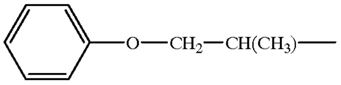 | $C_{31}H_{36}N_4O_7$ | 5.5, 88% | 577 | 575 |
| Compound BT | 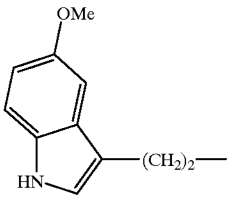 | $C_{33}H_{37}N_5O_7$ | 8.0, 52% | | 614 |

TABLE 1-continued

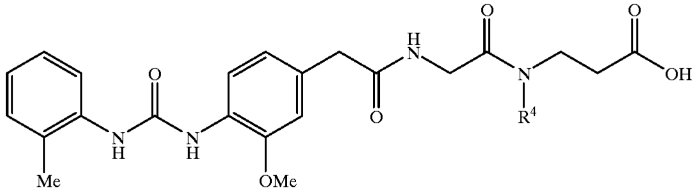

| Compound number | $R^4$ | MOLECULAR FORMULA | HPLC $R_T$ | $MH^+$ | $MH^-$ |
|---|---|---|---|---|---|
| Compound BU | 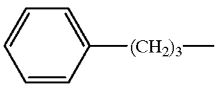 | $C_{31}H_{36}N_4O_6$ | 8.4, 85% | 561 | 559 |

EXAMPLE 3

Compounds BV to FJ

Step 1. Resin B from Step 2 Example 2 was treated with bromoacetic acid (0.47 g) in dimethylformamide (7 ml) and diisopropylcarbodiimide (0.67 ml). After standing at room temperature for 1.5 hours the mixture was filtered to give resin D which was washed.

Step 2. Resin D (100 mg) was swelled with dimethyl sulphoxide (1.5 ml) and then treated with propylamine (10 equivalents). After heating for 2 hours at 80° C. the mixture was filtered to give resin E which was washed (i) three times with dimethylformamide, (ii) three times with tetrahydrofuran, (iii) three times with dichloromethane.

Step 3. Resin E was treated with a solution of [3-methoxy-4-(3-o-tolylureido)phenyl]-acetic acid (70 mg, Reference Example 5) in dimethylformamide (1 ml), a solution of [O-(7-azabenzotriazol-1-yl)-1,1,3,3,-tetramethyluronium hexafluorophosphate] (75 mg) in dimethylformamide (1 ml), and diisopropylethylamine (100 $\mu$l). After standing at room temperature for 2 hours with occasional agitation the mixture was filtered to give resin F which was washed (i) four times with dimethylformamide, (ii) three times with methanol, (iii) three times with dichloromethane and then dried under vacuum.

Step 4. Resin F was treated with a mixture of dichloromethane and trifluoroacetic acid (2 ml, 1:1 v/v) and allowed to stand for 45 minutes. The mixture was filtered and the resin was washed with dichloromethane. The combined filtrate and washing were evaporated to give 3-{[({[3-methoxy-4-(3-o-tolylureido)phenyl]-acetyl}-prop-1-ylamino)-acetyl]-[3-(2-oxo-pyrrolidin-1-yl)-prop-1-yl]-amino}-propionic acid (Compound BV).

By proceeding in a similar manner to Example 3, but using the appropriately substituted amines in step 1 and the appropriately substituted amines step 3, there were prepared Compounds BW to FJ depicted in Table 2.

TABLE 2

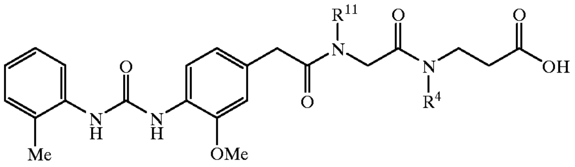

| Compound Number | $R^{11}$ | $R^4$ | MOLECULAR FORMULA | HPLC $R_T$ | $MH^+$ | $MH^-$ |
|---|---|---|---|---|---|---|
| Compound BW | 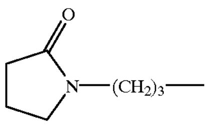 | $CH_2$=CH—$CH_2$— | C32H41N5O7 | 2.7, 80% | 625 $(M + 18)^+$ | |
| Compound BX | $CH_3C$(=O)—NH—$(CH_2)_2$— | $CH_2$=CH—$CH_2$— | C29H37N5O7 | 2.5, 78% | 568 | |
| Compound BY | 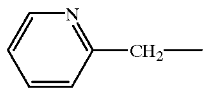 | $CH_2$=CH—$CH_2$— | C31H35N5O6 | 2.8, 68% | 574 | |
| Compound BZ | $CH_3$—$(CH_2)_2$— | $CH_2$=CH—$CH_2$— | C28H36N4O6 | 6.7, 100% | 542 $[M + 18]^+$ | |

TABLE 2-continued

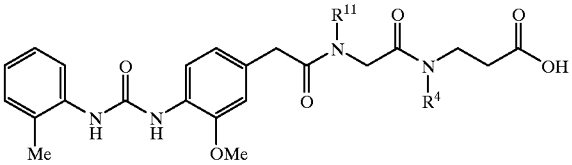

| Compound Number | $R^{11}$ | $R^4$ | MOLECULAR FORMULA | HPLC $R_T$ | $MH^+$ | $MH^-$ |
|---|---|---|---|---|---|---|
| Compound CA | 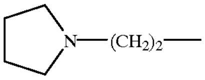 | $CH_2{=}CH—CH_2—$ | C31H41N5O6 | 2.0, 100% | 580 | |
| Compound CB | 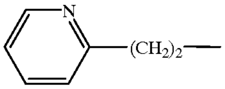 | $CH_2{=}CH—CH_2—$ | C32H37N5O6 | 3.5, 40% | 588 | |
| Compound CC | 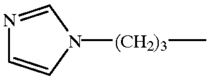 | $CH_2{=}CH—CH_2—$ | C31H38N6O6 | 3.0, 95% | 591 | |
| Compound CD | 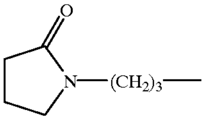 | $CH_3C({=}O)—NH—(CH_2)_2—$ | C33H44N6O8 | 2.3, 77% | | |
| Compound CE | $CH_3C({=}O)—NH—(CH_2)_2—$ | $CH_3C({=}O)—NH—(CH_2)_2—$ | C30H40N6O8 | 2.2, 79% | 630 [M + 18]$^+$ | |
| Compound CF | 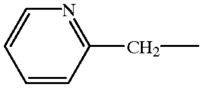 | $CH_3C({=}O)—NH—(CH_2)_2—$ | C32H38N6O7 | 2.4, 81% | 619 | |
| Compound CG | $CH_3—(CH_2)_2—$ | $CH_3C({=}O)—NH—(CH_2)_2—$ | C29H39N5O7 | 1.8, 100% | 570 | |
| Compound CH | 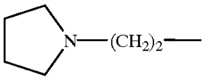 | $CH_3C({=}O)—NH—(CH_2)_2—$ | C32H44N6O7 | 2.4, 81% | 625 | |
| Compound CI | 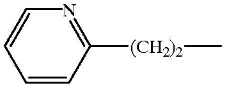 | $CH_3C({=}O)—NH—(CH_2)_2—$ | C33H40N6O7 | 2.3, 75% | 633 | |
| Compound CJ | 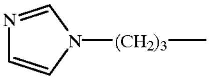 | $CH_3C({=}O)—NH—(CH_2)_2—$ | C32H41N7O7 | 2.2, 89% | 636 | |
| Compound CK | $HO—(O{=})C—(CH_2)_3—$ | 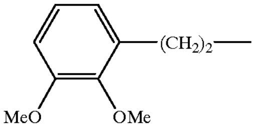 | C36H44N4O10 | 6.7, 100% | 690 | |
| Compound CL | 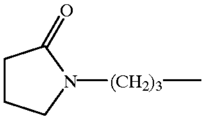 | 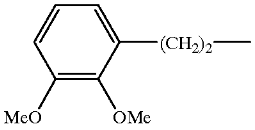 | C39H49N5O9 | 6.8, 100% | 730 | |

TABLE 2-continued
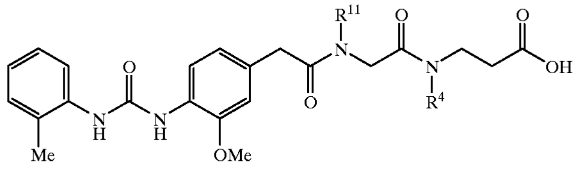
| Compound Number | $R^{11}$ | $R^4$ | MOLECULAR FORMULA | HPLC $R_T$ | $MH^+$ | $MH^-$ |
|---|---|---|---|---|---|---|
| Compound CM | $CH_3C(=O)—NH—(CH_2)_2—$ | 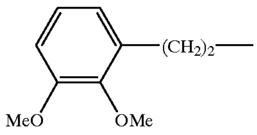 | C36H45N5O9 | 6.3, 100% | 689 | |
| Compound CN | 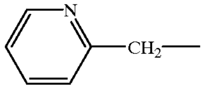 | 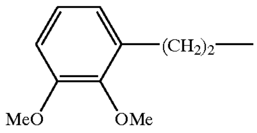 | C38H43N5O8 | 6.8, 81% | 698 | |
| Compound CO | $CH_3—(CH_2)_2—$ | 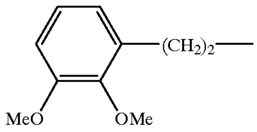 | C35H44N4O8 | 8.5, 100% | 666 $[M + 18]^+$ | |
| Compound CP | 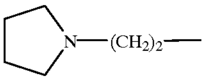 | 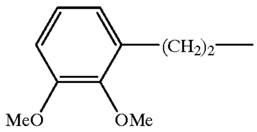 | C38H49N5O8 | 6.9, 100% | 704 | |
| Compound CQ | 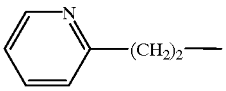 | 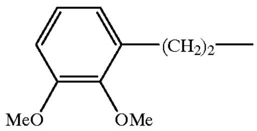 | C39H45N5O8 | 6.7, 89% | 712 | |
| Compound CR | 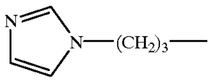 | 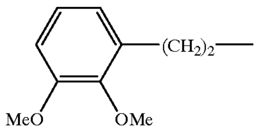 | C38H46N6O8 | 6.1, 69% | 715 | |
| Compound CS | $HO—(O=)C—(CH_2)_3—$ | 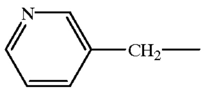 | C32H37N5O8 | 2.1, 22% | 620 | |
| Compound CT | 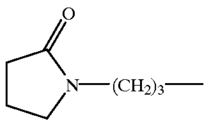 | 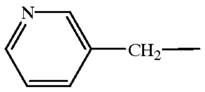 | C35H42N6O7 | 1.8, 82% | | 657 |
| Compound CU | $CH_3C(=O)—NH—(CH_2)_2—$ | 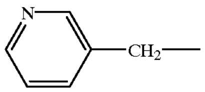 | C32H38N6O7 | 2.2, 18% | 619 | |

TABLE 2-continued
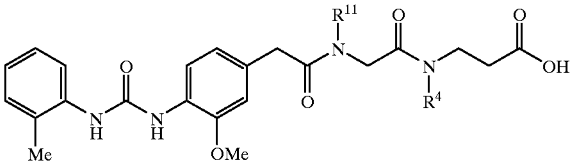
| Compound Number | $R^{11}$ | $R^4$ | MOLECULAR FORMULA | HPLC $R_T$ | $MH^+$ | $MH^-$ |
|---|---|---|---|---|---|---|
| Compound CV | 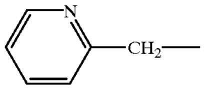 | 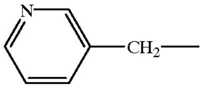 | C34H36N6O6 | 2.2, 50% | 625 | |
| Compound CW | $CH_3$—$(CH_2)_2$— | 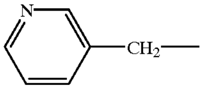 | C31H37N5O6 | | 576 | |
| Compound CX | 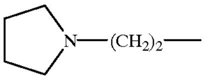 | 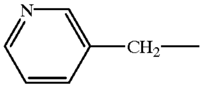 | C34H42N6O6 | 2.1, 16% | 631 | |
| Compound CY | 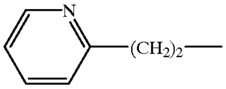 | 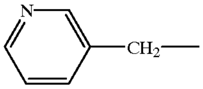 | C35H38N6O6 | 2.1, 37% | 639 | |
| Compound CZ | 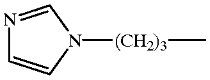 | 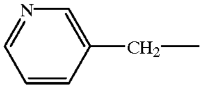 | C34H39N7O6 | 2.1, 40% | 642 | |
| Compound DA | HO—(O═)C—$(CH_2)_3$— | 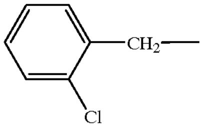 | C33H37ClN4O8 | 7.0, 100% | | 651 |
| Compound DB | 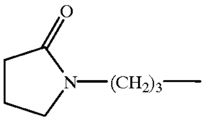 | 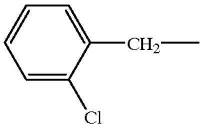 | C36H42ClN5O7 | 7.0, 55% | 709 $[M + 18]^+$ | |
| Compound DC | $CH_3C$(═O)—NH—$(CH_2)_2$— | 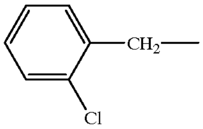 | C33H38ClN5O7 | 6.6, 30%<br>2.6, 70% | | 650 |
| Compound DD | 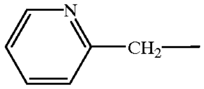 | 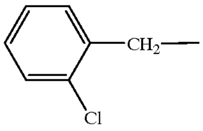 | C35H36ClN5O6 | 7.0, 62% | 566 | |
| Compound DE | $CH_3$—$(CH_2)_2$— | 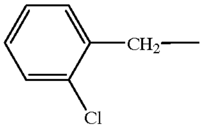 | C32H37ClN4O6 | 6.6, 64%<br>8.7, 46% | 566 | |

TABLE 2-continued
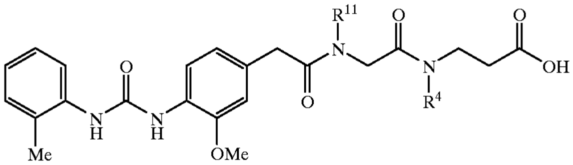
| Compound Number | $R^{11}$ | $R^4$ | MOLECULAR FORMULA | HPLC $R_T$ | $MH^+$ | $MH^-$ |
|---|---|---|---|---|---|---|
| Compound DF | 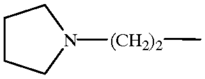 | 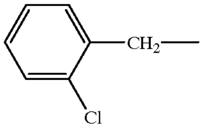 | C35H42ClN5O6 | 7.0, 50% | 664 | |
| Compound DG | 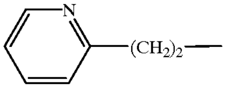 | 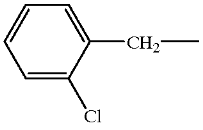 | C36H38ClN5O6 | 6.8, 53% | 672 | |
| Compound DH | 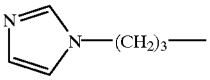 | 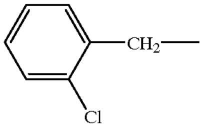 | C35H39ClN6O6 | 6.4, 23% | 675 | |
| Compound DI | $HO—(O{=})C—(CH_2)_3—$ | 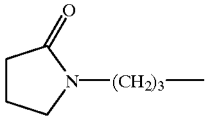 | C33H43N5O9 | 2.5, 46% | 612 | 652 |
| Compound DJ | 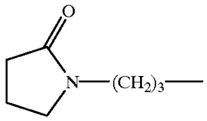 | 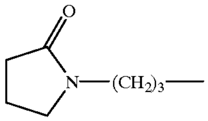 | C36H48N6O8 | 2.5, 67% | 710 [M + 18]+ | |
| Compound DK | $CH_3C({=}O)—NH—(CH_2)_2—$ | 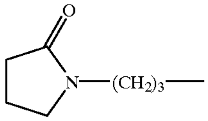 | C33H44N6O8 | 2.3, 86% | 670 [M + 18]+ | |
| Compound DL | 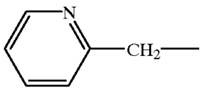 | 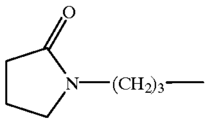 | C35H42N6O7 | 2.6, 67% | 659 | |
| Compound DM | $CH_3—(CH_2)_2—$ | 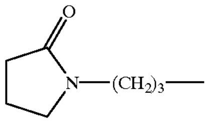 | C32H43N5O7 | 2.0, 61% | 627 | |
| Compound DN | 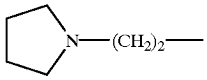 | 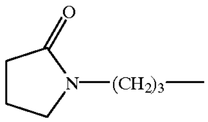 | C35H48N6O7 | 2.6, 72% | 665 | |

TABLE 2-continued
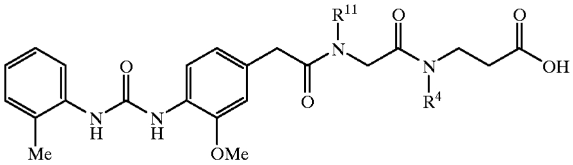
| Compound Number | $R^{11}$ | $R^4$ | MOLECULAR FORMULA | HPLC $R_T$ | $MH^+$ | $MH^-$ |
|---|---|---|---|---|---|---|
| Compound DO | 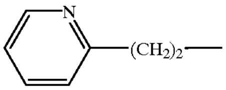 | 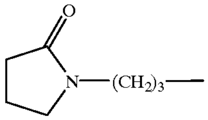 | C36H44N6O7 | 2.5, 67% | 673 | |
| Compound DP | 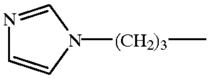 | 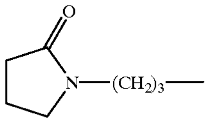 | C35H45N7O7 | 5.4, 76% | 676 | |
| Compound DQ | HO—(O═)C—$(CH_2)_3$— | 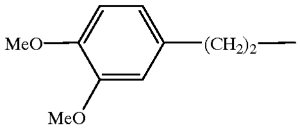 | C35H42N4O10 | 5.5, 30% | 612 | |
| Compound DR | 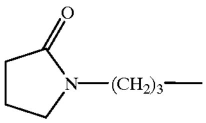 | 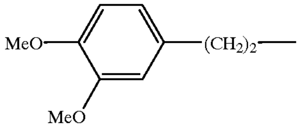 | C38H47N5O9 | 5.4, 67% | 701 | |
| Compound DS | $CH_3C$(═O)—NH—$(CH_2)_2$— | 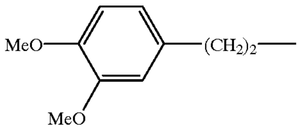 | C35H43N5O9 | 2.2, 100% | 678 | |
| Compound DT | 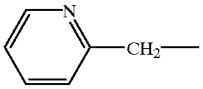 | 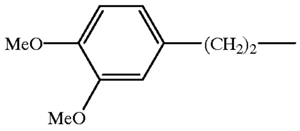 | C37H41N5O8 | 5.5, 53% | 684 | |
| Compound DU | $CH_3$—$(CH_2)_2$— | 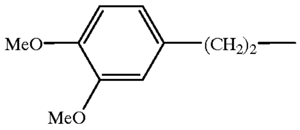 | C34H42N4O8 | 7.4, 100% | 652 [M + 18]$^+$ | |
| Compound DV | 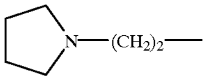 | 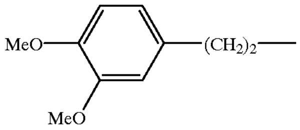 | C37H47N5O8 | 5.6, 50% | 690 | |
| Compound DW | 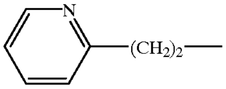 | 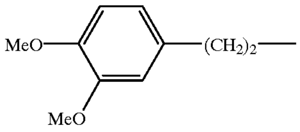 | C38H43N5O8 | 2.3, 84% | 698 | |

TABLE 2-continued
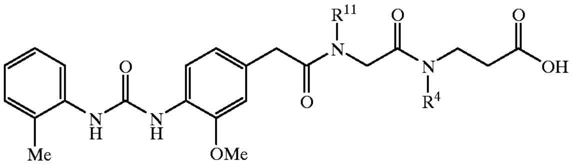
| Compound Number | $R^{11}$ | $R^4$ | MOLECULAR FORMULA | HPLC $R_T$ | $MH^+$ | $MH^-$ |
|---|---|---|---|---|---|---|
| Compound DX | 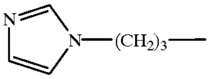 | 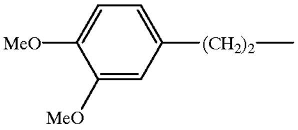 | C37H44N6O8 | 2.1, 100% | 701 | |
| Compound DY | HO—(O═)C—$(CH_2)_3$— | 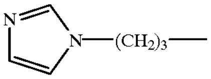 | C32H40N6O8 | 2.3, 41%, | 637 | |
| Compound DZ | 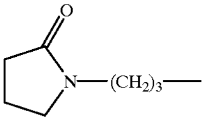 | 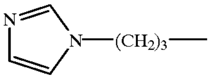 | C35H45N7O7 | 2.4, 55%, | 676 | |
| Compound EA | $CH_3C(═O)$—NH—$(CH_2)_2$— | 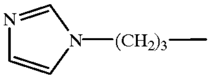 | C32H41N7O7 | 2.2, 55% | 636 | |
| Compound EB | 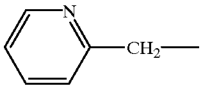 | 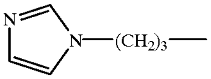 | C34H39N7O6 | 2.2, 34%, | 642 | |
| Compound EC | $CH_3$—$(CH_2)_2$— | 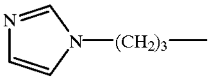 | C31H40N6O6 | 1.7, 100% | 593 | |
| Compound ED | 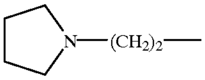 | 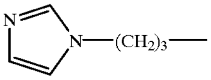 | C34H45N7O6 | 6.0, 26%, | 648 | |
| Compound EE | 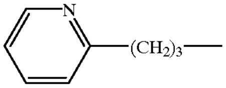 | 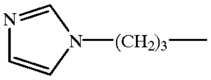 | C35H41N7O6 | 2.1, 72% | 656 | |
| Compound EF | 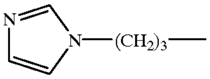 | 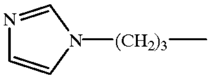 | C34H42N8O6 | 2.1, 66% | 659 | |
| Compound EG | HO—(O═)C—$(CH_2)_3$— | 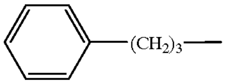 | C35H42N4O8 | 7.3, 66%, 8.5, 34% | 598 | |
| Compound EH | 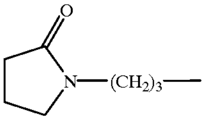 | 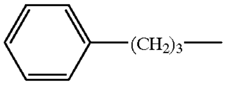 | C38H47N5O7 | 7.4, 65% | 703 $[M + 18]^+$ | |

TABLE 2-continued
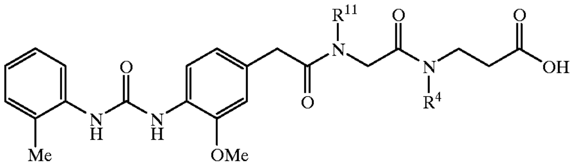
| Compound Number | $R^{11}$ | $R^4$ | MOLECULAR FORMULA | HPLC $R_T$ | $MH^+$ | $MH^-$ |
|---|---|---|---|---|---|---|
| Compound EI | $CH_3C(=O)—NH—(CH_2)_2—$ | 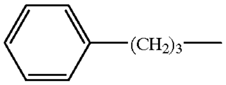 | C35H43N5O7 | 7.0, 71% | 646 | |
| Compound EJ | 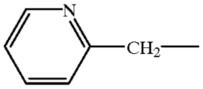 | 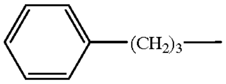 | C37H41N5O6 | 7.5, 50%, 7.8, 24%, 8.6, 27% | 652 | |
| Compound EK | $CH_3—(CH_2)_2—$ | 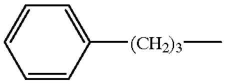 | C34H42N4O6 | 8.9, 72% | 620 $[M + 18]^+$ | |
| Compound EL | 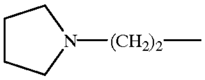 | 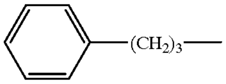 | C37H47N5O6 | 7.5, 56% 8.6, 38% | 658 | |
| Compound EM | 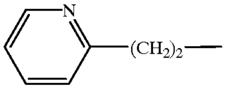 | 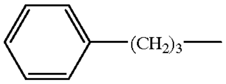 | C38H43N5O6 | 7.3, 65%, 8.6, 35% | 666 | |
| Compound EN | 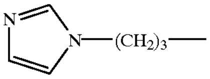 | 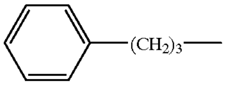 | C37H44N6O6 | 6.8, 64%, 8.6, 36% | 669 | |
| Compound EO | 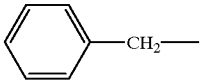 | 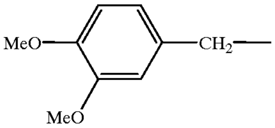 | C38H42N4O8 | 14.1, 89% | 683 | 681 |
| Compound EP | 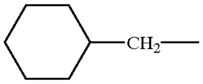 | 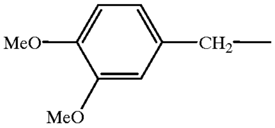 | C38H48N4O8 | 15.3, 92% | 689 | 687 |
| Compound EQ | 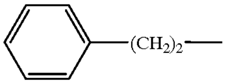 | 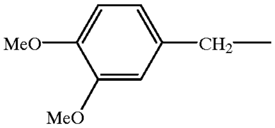 | C39H44N4O8 | 14.5, 84% | 697 | |
| Compound ER | 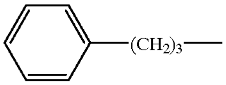 | 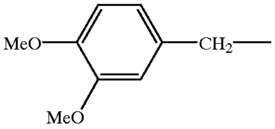 | C40H46N4O8 | 15.0, 83% | 711 | 709 |

TABLE 2-continued
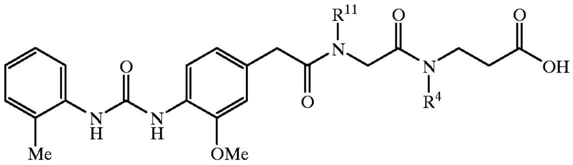
| Compound Number | $R^{11}$ | $R^4$ | MOLECULAR FORMULA | HPLC $R_T$ | $MH^+$ | $MH^-$ |
|---|---|---|---|---|---|---|
| Compound ES | 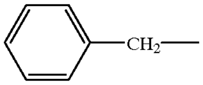 | 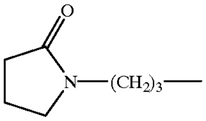 | C36H43N5O7 | 13.4, 87% | 658 | 656 |
| Compound ET | 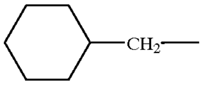 | 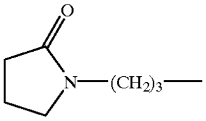 | C36H49N5O7 | 14.5, 88% | 664 | 662 |
| Compound EU | 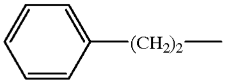 | 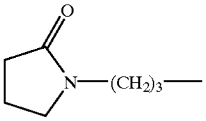 | C37H45N5O7 | 13.9, 89% | 672 | 670 |
| Compound EV | 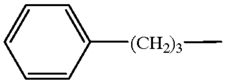 | 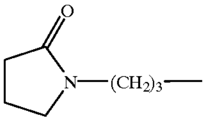 | C38H47N5O7 | 14.4, 84% | 686 | 684 |
| Compound EW | 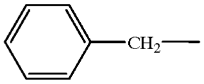 | 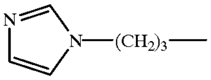 | C35H40N6O6 | 12.8, 81% | 641 | 639 |
| Compound EX | 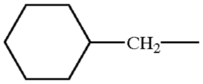 | 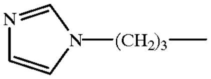 | C35H46N6O6 | 13.9, 30% | 647 | 645 |
| Compound EY | 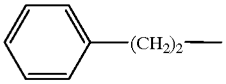 | 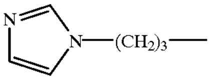 | C36H42N6O6 | 13.2, 51% | 655 | 653 |
| Compound EZ | 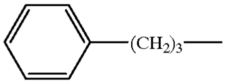 | 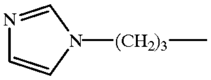 | C37H44N6O6 | 13.7, 45% | 669 | 667 |
| Compound FA | 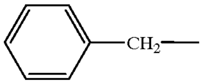 | 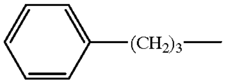 | C38H42N4O6 | 16.8, 92% | | |
| Compound FB | 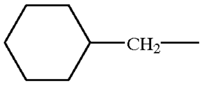 | 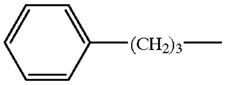 | C38H48N4O6 | 18.1, 92% | 657 | 655 |
| Compound FC | 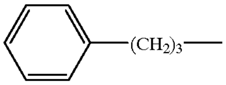 | 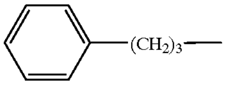 | C39H44N4O6 | 17.2, 92% | 665 | 663 |

TABLE 2-continued

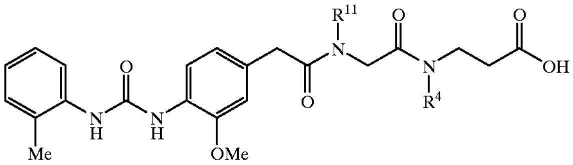

| Compound Number | $R^{11}$ | $R^4$ | MOLECULAR FORMULA | HPLC $R_T$ | $MH^+$ | $MH^-$ |
|---|---|---|---|---|---|---|
| Compound FD | 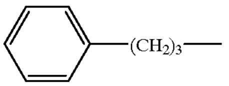 | 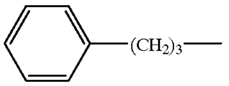 | C40H46N4O6 | 17.7, 86% | 679 | 677 |
| Compound FE | 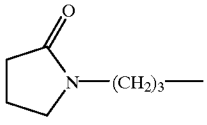 | 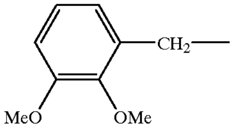 | C38H47N5O9 | 13.4, 73% | 718 | 716 |
| Compound FF | 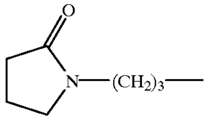 | 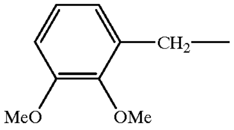 | C38H42N4O8 | 15.9, 82% | 683 | 681 |
| Compound FG | 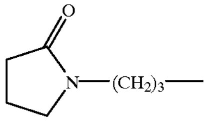 | 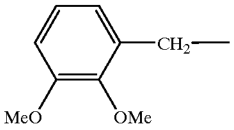 | C38H48N4O8 | 17.1, 83% | 689 | 687 |
| Compound FH | 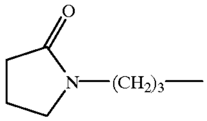 | 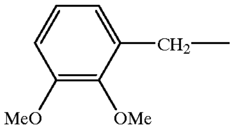 | C39H44N4O8 | 16.5, 82% | 697 | 695 |
| Compound FI | 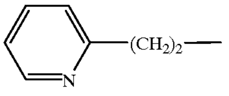 | 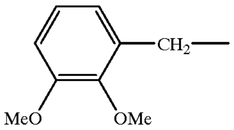 | C38H43N5O8 | 13.0, 85% | 698 | 696 |
| Compound FJ | 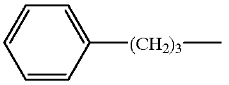 | 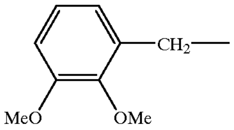 | C40H46N4O8 | 16.8, 70% | 711 | 709 |

EXAMPLE 4

Compounds FK to KV

Step 1. Resin A from Step 1 Example 2 was suspended in dimethylformamide (30 ml) and then treated with phenethylamine (10 eqivalents). After standing at room temperature overnight the mixture was filtered to give resin G which was washed with (i) dimethylformamide, (ii) tetrahydrofuran, (iii) dichloromethane and then dried in a desiccator under high vacuum for 2 hours.

By proceeding in a similar manner but replacing phenethylamine by allylamine, isobutylamine, (cyclohexyl) methylamine, 3-(2-oxo-1-pyrrolydinyl)prop-1-ylamine, 4-phenyl-1-butylamine, piperonylamine, 3-(1-imidazolyl) prop-1-ylamine, 3-(2-methyl-1-piperdinyl)prop-1-ylamine, 2-(2-pyridinyl)ethylamine, (2-acetamido)ethylamine or 2-methoxybenzylamine there were prepared resins H to R.

A library of 144 compounds were prepared from resins H to R, using an ACT496 robot (96 well plate format), in the following manner.

Step 2. The appropriate resin (40 mg, resins H to S prepared as described above) was placed in each well and treated with dimethylformamide (1.2 ml) for 5 minutes and then drained. Dimethylformamide (0.35 ml) was added to each well, the system was warmed to 30° C., and each well was treated with (i) a solution of diisopropylethylamine in dimethylformamide (0.5 ml, 0.66M), (ii) a solution of N-(9-fluorenylmethoxycarbonyl)glycine in dimethylformamide (0.375 ml, 0.294M) and (iii) a solution of [O-(7- azabenzotriazol-1-yl)-1,1,3,3,-tetramethyluronium hexafluorophosphate] in dimethylformamide (0.375 ml, 0.294M). After standing at 30° C. for 2 hours with mixing the wells were drained and the resins in each well were then washed five times with dimethylformamide (1.2 ml) with mixing for 5 minutes. Further batches of resins H to S were similarly modified by replacing N-(9-fluorenylmethoxycarbonyl)glycine with N-(9-fluorenylmethoxycarbonyl)-3-amino propionic acid, N-(9-fluorenylmethoxycarbonyl)-4-aminobutyric acid, N-(9-fluorenylmethoxycarbonyl)sareosine or N-(9-fluorenylmethoxycarbonyl)-4-N-methylaminobutyric acid.

Step 3. The resins from Step 2 in each well were then treated with 20% piperidine in dimethylformamide (1.2 ml) with mixing for 5 minutes, the wells were drained and the procedure repeated. The resins in each well were then washed (with mixing for 5 minutes) seven times with dimethylformamide (1.2 ml).

Step 4. Dimethylformamide (0.35 ml) was added to the resin in each well followed by (i) a solution of diisopropylethylamine in dimethylformamide (0.5 ml, 0.44M), (ii) a solution of 4-(phenylureido)phenylacteic acid in dimethylformamide (0.375 ml, 0.196M), (iii) a solution of [O-(7-azabenzotriazol-1-yl)-1,1,3,3,-tetramethyluronium hexafluorophosphate] in dimethylformamide (0.375 ml, 0.196M). After mixing for 2 hours the wells drained and each well was washed (with mixing for 5 minutes) (i) three times with dimethylformamide (1.2 ml), (ii) five times with tetrahydrofuran (1.2 ml), (iii) seven times with dichloromethane (1.2 ml). Further batches of resins from Step 3 were similarly modified by replacing [4-(phenylureido)phenyl]-acetic acid with [4-(3-o-tolylureido)phenyl]-acetic acid, [4-(phenylureido)phenyl]-propionic acid, [3-(phenylureido)phenyl]-acetic acid, [3-methoxy-4-(3-o-tolylureido)phenyl]-acetic acid or [3-methoxy-4-(3-o-tolylureido)phenyl]-propionic acid.

Step 5. The system heating was switched off. The resins in each well were treated with a mixture of trifluoroacetic acid and dichloromethane (2 ml, 1:1 v/v) for 45 minutes, the filtrate was collected and the procedure repeated once more. The combined filtrates were evaporated on a turbovap evaporator (vortexed $N_2$ gas) to give Compounds FK to KV depicted in tables 3 to 15. The retention times ($R_T$), and area of main peak as a percentage of the total sample, shown in tables 3 to 15 were determined under HPLC conditions using as elutant (i) mixture of 0.05% trifluoroacetic acid in acetonitrile and 0.05% trifluoroacetic acid in water (1:19, v/v) for 2 minutes (ii) a mixture of 0.05% trifluoroacetic acid in acetonitrile and 0.05% trifluoroacetic acid in water (1:19 to 19:1, v/v) gradient elution over 10 minutes, (iii) a mixture of 0.05% trifluoroacetic acid in acetonitrile and 0.05% trifluoroacetic acid in water (19:1, v/v) for 2 minutes, (iv) a mixture of 0.05% trifluoroacetic acid in acetonitrile and 0.05% trifluoroacetic acid in water (19:1 to 1:19, v/v) gradient elution over 2 minutes.

TABLE 3

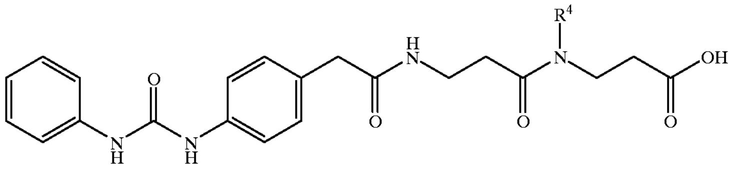

| Compound number | $R^4$ | MOLECULAR FORMULA | HPLC $R_T$ | $MH^+$ | $MH^-$ |
|---|---|---|---|---|---|
| Compound FK | 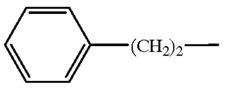 | $C_{29}H_{32}N_4O_5$ | 14.0, >75% | 517 | |
| Compound FL | $CH_2{=}CH{-}CH_2{-}$ | $C_{24}H_{28}N_4O_5$ | 12.0, >90% | 453 | |
| Compound FM | $(CH_3)_2CH{-}CH_2{-}$ | $C_{25}H_{32}N_4O_5$ | 13.1, >90% | 469 | |
| Compound FN | 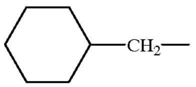 | $C_{28}H_{36}N_4O_5$ | 14.8, >90% | 509 | |
| Compound FO | 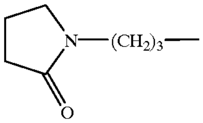 | $C_{28}H_{35}N_5O_6$ | 11.0, >90% | 560 [M + Na]$^+$ | |
| Compound FP | 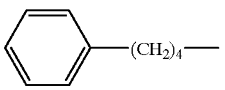 | $C_{31}H_{36}N_4O_5$ | 15.2, >90% | | |

TABLE 3-continued

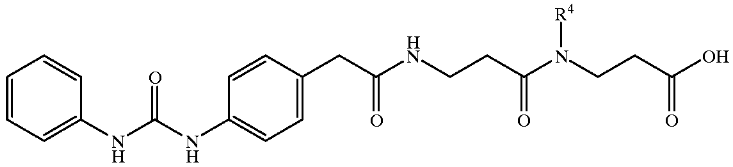

| Compound number | $R^4$ | MOLECULAR FORMULA | HPLC $R_T$ | $MH^+$ | $MH^-$ |
|---|---|---|---|---|---|
| Compound FQ | 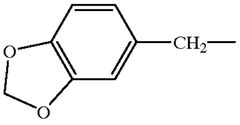 | $C_{29}H_{30}N_4O_7$ | 13.6, >75% | 569 $[M + Na]^+$ | |
| Compound FR | 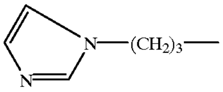 | $C_{27}H_{32}N_6O_5$ | 10.0, >75% | 521 | |
| Compound FS | 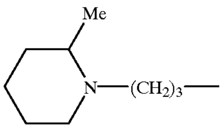 | $C_{30}H_{41}N_5O_5$ | 11.3, >90% | 552 | |
| Compound FT | 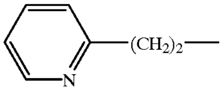 | $C_{28}H_{31}N_5O_5$ | 10.2, >90% | 518 | |
| Compound FU | $CH_3C(=O)NH-(CH_2)_2-$ | $C_{25}H_{31}N_5O_6$ | 10.1, >90% | 498 | |
| Compound FV | 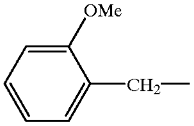 | $C_{29}H_{32}N_4O_6$ | 13.7, >75% | 533 | |

TABLE 4

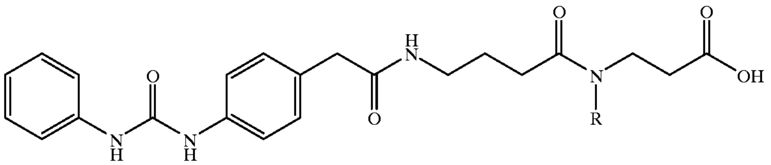

| Compound number | $R^4$ | MOLECULAR FORMULA | HPLC $R_T$ | $MH^+$ | $MH^-$ |
|---|---|---|---|---|---|
| Compound FW | 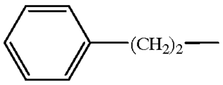 | $C_{30}H_{34}N_4O_5$ | 10.3, >75% | 531 | |
| Compound FX | $CH_2=CH-CH_2-$ | $C_{25}H_{30}N_4O_5$ | 13.9, >50% | 467 | |
| Compound FY | $(CH_3)_2CH-CH_2-$ | $C_{26}H_{34}N_4O_5$ | 14.7, >50% | 483 | |

TABLE 4-continued
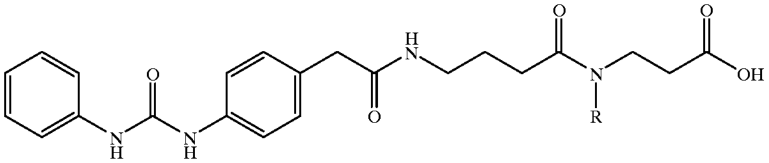
| Compound number | $R^4$ | MOLECULAR FORMULA | HPLC $R_T$ | $MH^+$ | $MH^-$ |
|---|---|---|---|---|---|
| Compound FZ | 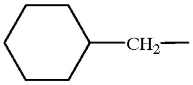 | $C_{29}H_{38}N_4O_5$ | 11.0, <50% | 537 | |
| Compound GA | 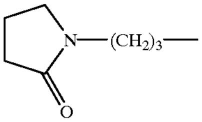 | $C_{29}H_{37}N_5O_6$ | 13.7, >75% | | 550 |
| Compound GB | 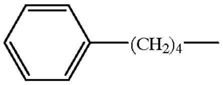 | $C_{32}H_{38}N_4O_5$ | 10.8, >75% | 559 | |
| Compound GC | 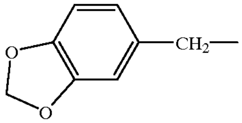 | $C_{30}H_{32}N_4O_7$ | 9.9, >75% | | 559 |
| Compound GD | 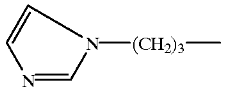 | $C_{28}H_{34}N_6O_5$ | 8.4, >75% | | 533 |
| Compound GE | 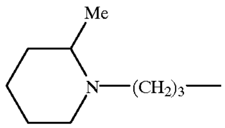 | $C_{31}H_{43}N_5O_5$ | 8.8, >75% | | 564 |
| Compound GF | 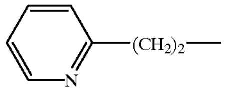 | $C_{29}H_{33}N_5O_5$ | 8.5, >75% | | 530 |
| Compound GG | $CH_3C(=O)NH-(CH_2)_2-$ | $C_{26}H_{33}N_5O_6$ | 8.5, >75% | | 510 |
| Compound GH | 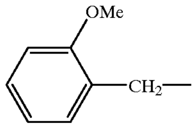 | $C_{30}H_{34}N_4O_6$ | 10.0, >75% | | 545 |

TABLE 5
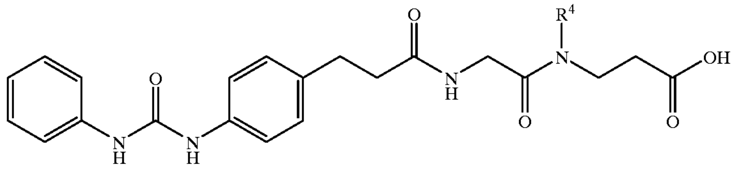
| Compound number | $R^4$ | MOLECULAR FORMULA | HPLC $R_T$ | $MH^+$ | $MH^-$ |
|---|---|---|---|---|---|
| Compound GI | 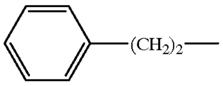 | $C_{29}H_{32}N_4O_5$ | 14.0, >75% | 517 | |
| Compound GJ | $CH_2{=}CH{-}CH_2{-}$ | $C_{24}H_{28}N_4O_5$ | 12.0, >90% | 453 | |
| Compound GK | $(CH_3)_2CH{-}CH_2{-}$ | $C_{25}H_{32}N_4O_5$ | 13.1, >90% | 469 | |
| Compound GL | 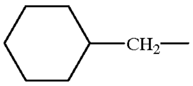 | $C_{28}H_{36}N_4O_5$ | 14.8, >90% | 509 | |
| Compound GM | 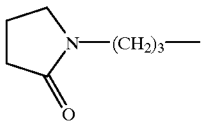 | $C_{28}H_{35}N_5O_6$ | 11.0, >90% | 560 | |
| Compound GN | 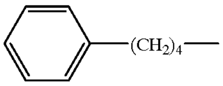 | $C_{31}H_{36}N_4O_5$ | 15.2, >90% | | |
| Compound GO | 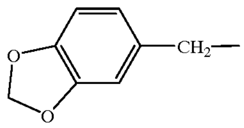 | $C_{29}H_{30}N_4O_7$ | 13.6, >75% | 569 $[M + Na]^+$ | |
| Compound GP | 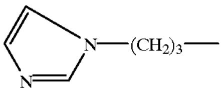 | $C_{27}H_{32}N_6O_5$ | 10.0, >75% | 521 | |
| Compound GQ | 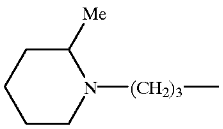 | $C_{30}H_{41}N_5O_5$ | 11.3, >90% | 552 | |
| Compound GR | 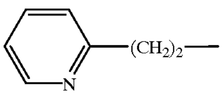 | $C_{28}H_{31}N_5O_5$ | 10.2, >90% | 518 | |
| Compound GS | $CH_3C({=}O)NH{-}(CH_2)_2{-}$ | $C_{25}H_{31}N_5O_6$ | 10.1, >90% | 498 | |
| Compound GT | 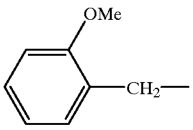 | $C_{29}H_{32}N_4O_6$ | 13.7, >75% | 533 | |

TABLE 6

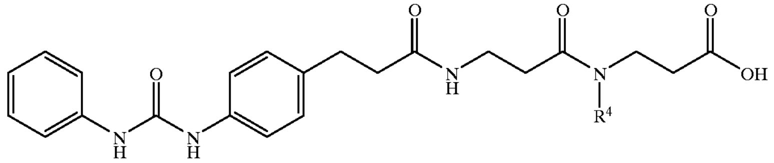

| Compound number | $R^4$ | MOLECULAR FORMULA | HPLC $R_T$ | $MH^+$ | $MH^-$ |
|---|---|---|---|---|---|
| Compound GU | 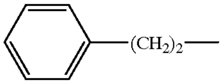 | $C_{30}H_{34}N_4O_5$ | 13.8, >90% | 531 | |
| Compound GV | $CH_2{=}CH{-}CH_2{-}$ | $C_{25}H_{30}N_4O_5$ | 11.9, >90% | 467 | |
| Compound GW | $(CH_3)_2CH{-}CH_2{-}$ | $C_{26}H_{34}N_4O_5$ | 12.8, >90% | 483 | |
| Compound GX | 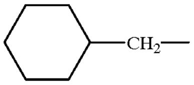 | $C_{29}H_{38}N_4O_5$ | 14.3, >90% | 523 | |
| Compound GY | 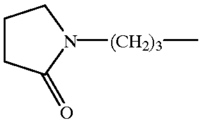 | $C_{29}H_{37}N_5O_6$ | 11.5, >90% | 614 $[M + Na]^+$ | |
| Compound GZ | 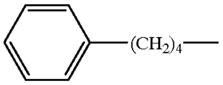 | $C_{32}H_{38}N_4O_5$ | 15.7, >95% | 621 $[M + Na]^+$ | |
| Compound HA | 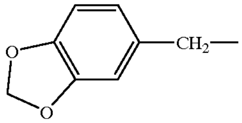 | $C_{30}H_{32}N_4O_7$ | 14.0, >90% | 623 $[M + Na]^+$ | |
| Compound HB | 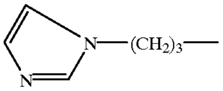 | $C_{28}H_{34}N_6O_5$ | 10.6, >90% | 575 | |
| Compound HC | 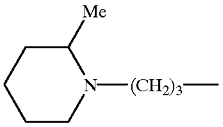 | $C_{31}H_{43}N_5O_5$ | 8.9, >75% | | 564 |
| Compound HD | 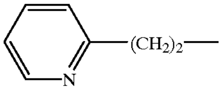 | $C_{29}H_{33}N_5O_5$ | 8.4, >75% | | 530 |
| Compound HE | $CH_3C({=}O)NH{-}(CH_2)_2{-}$ | $C_{26}H_{33}N_5O_6$ | 8.5, >90% | | 510 |
| Compound HF | 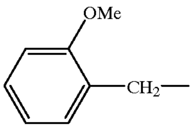 | $C_{30}H_{34}N_4O_6$ | 10.1, >90% | | 545 |

TABLE 7
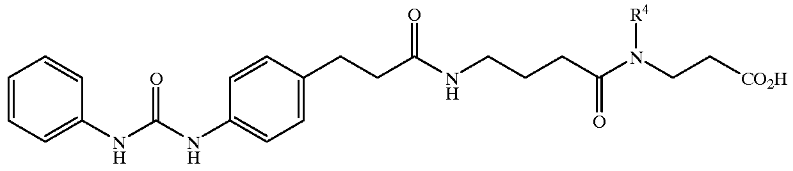
| Compound number | $R^4$ | MOLECULAR FORMULA | HPLC $R_T$ | $MH^+$ | $MH^-$ |
|---|---|---|---|---|---|
| Compound HG | 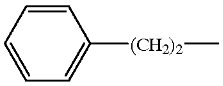 | $C_{31}H_{36}N_4O_5$ | 10.7, >90% | 545 | |
| Compound HH | $CH_2{=}CH{-}CH_2{-}$ | $C_{26}H_{32}N_4O_5$ | 14.1, >75% | 481 | |
| Compound HI | $(CH_3)_2CH{-}CH_2{-}$ | $C_{27}H_{36}N_4O_5$ | 9.9, >75% | 497 | |
| Compound HJ | 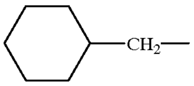 | $C_{30}H_{40}N_4O_5$ | 11.1, >75% | 537 | |
| Compound HK | 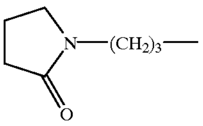 | $C_{30}H_{39}N_5O_6$ | 8.8, >75% | | 564 |
| Compound HL | 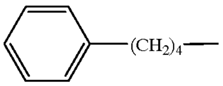 | $C_{33}H_{40}N_4O_5$ | 10.8, >90% | | 571 |
| Compound HM | 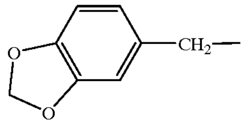 | $C_{31}H_{34}N_4O_7$ | 10.0, >90% | | 573 |
| Compound HN | 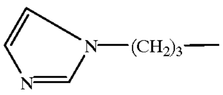 | $C_{29}H_{36}N_6O_5$ | 8.5, >75% | | 547 |
| Compound HO | 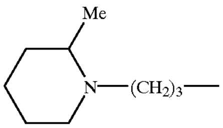 | $C_{32}H_{45}N_5O_5$ | 8.9, >90% | | 575 |
| Compound HP | 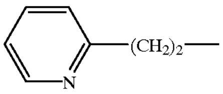 | $C_{30}H_{35}N_5O_5$ | 8.5 , >90% | | 544 |
| Compound HQ | $CH_3C({=}O)NH{-}(CH_2)_2{-}$ | $C_{27}H_{35}N_5O_6$ | 8.6, >90% | | 524 |
| Compound HR | 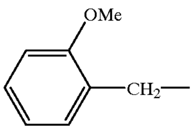 | $C_{31}H_{36}N_4O_6$ | 8.2, >95% | | 559 |

TABLE 8

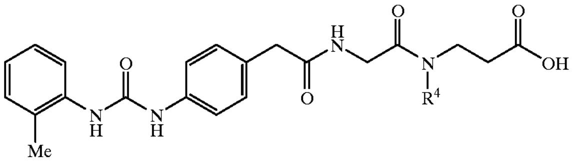

| Compound number | $R^4$ | MOLECULAR FORMULA | HPLC $R_T$ | $MH^+$ | $MH^-$ |
|---|---|---|---|---|---|
| Compound HS | 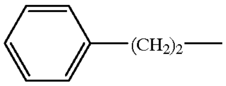 | $C_{29}H_{32}N_4O_5$ | 14.2, >75% | 517 | |
| Compound HT | $CH_2{=}CH{-}CH_2{-}$ | $C_{24}H_{28}N_4O_5$ | 12.0, >90% | 453 | |
| Compound HU | $(CH_3)_2CH{-}CH_2{-}$ | $C_{25}H_{32}N_4O_5$ | 13.1, >90% | 469 | |
| Compound HV | 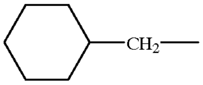 | $C_{28}H_{36}N_4O_5$ | 14.9, >90% | 509 | |
| Compound HW | 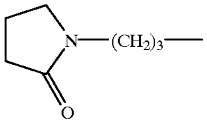 | $C_{28}H_{35}N_5O_6$ | 11.0, >90% | 560 $[M + Na]^+$ | |
| Compound HX | 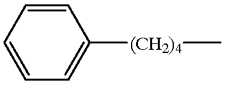 | $C_{31}H_{36}N_4O_5$ | 15.4, >90% | 567 $[M + Na]^+$ | |
| Compound HY | 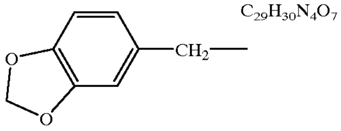 | $C_{29}H_{30}N_4O_7$ | 13.7, >75% | 569 $[M + Na]^+$ | |
| Compound HZ | 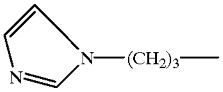 | $C_{27}H_{32}N_6O_5$ | 10.0, >75% | 521 | |
| Compound JA | 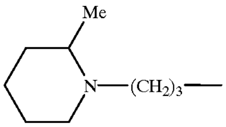 | $C_{30}H_{41}N_5O_5$ | 11.2, >90% | 552 | |
| Compound JB | 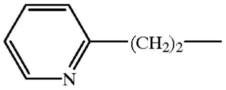 | $C_{28}H_{31}N_5O_5$ | 10.2, >90% | 518 | |
| Compound JC | $CH_3C({=}O)NH{-}(CH_2)_2{-}$ | $C_{25}H_{31}N_5O_6$ | 10.0, >90% | 498 | |
| Compound JD | 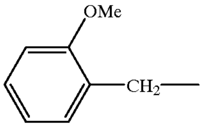 | $C_{29}H_{32}N_4O_6$ | 13.7, >75% | 533 | |

TABLE 9

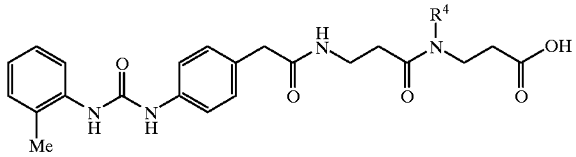

| Compound number | $R^4$ | MOLECULAR FORMULA | HPLC $R_T$ | $MH^+$ | $MH^-$ |
|---|---|---|---|---|---|
| Compound JF | 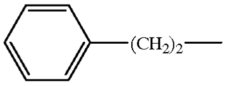 | $C_{30}H_{34}N_4O_5$ | 13.8, >90% | 531 | |
| Compound JG | $CH_2{=}CH{-}CH_2{-}$ | $C_{25}H_{30}N_4O_5$ | 11.9, >90% | 467 | |
| Compound JH | $(CH_3)_2CH{-}CH_2{-}$ | $C_{26}H_{34}N_4O_5$ | 12.8, >90% | 483 | |
| Compound JI | 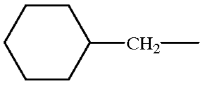 | $C_{29}H_{38}N_4O_5$ | 14.5, >90% | 523 | |
| Compound JJ | 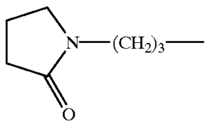 | $C_{28}H_{37}N_5O_6$ | 11.5, >90% | 614 $[M + Na + CH_3CN]^+$ | |
| Compound JK | 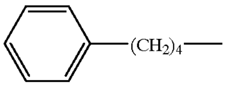 | $C_{32}H_{38}N_4O_5$ | 15.8, >95% | | |
| Compound JL | 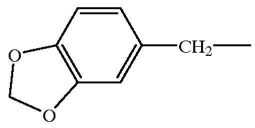 | $C_{30}H_{32}N_4O_7$ | 14.0, >9.0% | 623 $[M + Na + CH_3CN]^+$ | |
| Compound JM | 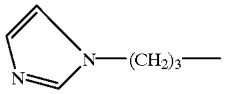 | $C_{28}H34N_6O_5$ | 10.3, >90% | 575 $[M + CH_3CN]^+$ | |
| Compound JN | 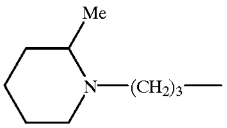 | $C_{31}H_{43}N_5O_5$ | 8.9, >50% | | 564 |
| Compound JO | 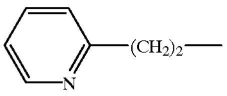 | $C_{29}H_{33}N_5O_5$ | 8.6, >50% | | 530 |
| Compound JP | $CH_3C({=}O)NH{-}(CH_2)_2{-}$ | $C_{26}H_{33}N_5O_6$ | 8.6, >75% | | 510 |
| Compound JQ | 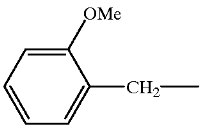 | $C_{30}H_{34}N_4O_6$ | 10.1, >90% | | 545 |

TABLE 10
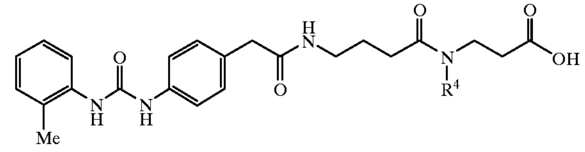
| Compound number | $R^4$ | MOLECULAR FORMULA | HPLC $R_T$ | $MH^+$ | $MH^-$ |
|---|---|---|---|---|---|
| Compound JR | 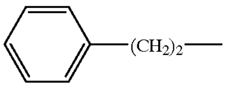 | $C_{21}H_{36}N_4O_5$ | 10.7, >75% | 545 | |
| Compound JS | $CH_2$=CH—$CH_2$— | $C_{26}H_{32}N_4O_5$ | 14.0, >75% | 481 | |
| Compound JT | $(CH_3)_2$CH—$CH_2$— | $C_{27}H_{36}N_4O_5$ | 10.0, >50% | 497 | |
| Compound JU | 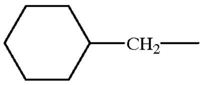 | $C_{30}H_{40}N_4O_5$ | 11.1, >75% | 537 | |
| Compound JV | 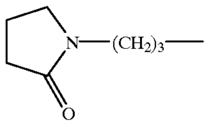 | $C_{30}H_{39}N_5O_6$ | 8.9, >75 % | | 564 |
| Compound JW | 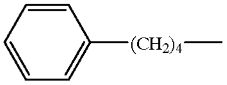 | $C_{33}H_{40}N_4O_5$ | 10.9, >90% | | 571 |
| Compound JX | 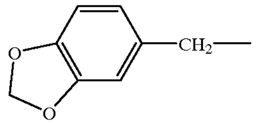 | $C_{21}H_{34}N_4O_7$ | 10.0, >75% | | 573 |
| Compound JY | 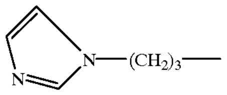 | $C_{29}H_{36}N_6O_5$ | 8.6, >75% | | 547 |
| Compound JZ | 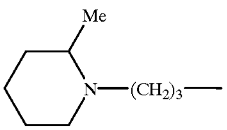 | $C_{32}H_{45}N_5O_5$ | 9.0, >75% | | 578 |
| Compound KA | 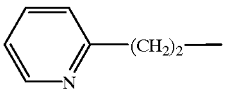 | $C_{30}H_{35}N_5O_5$ | 8.6, >75% | | 544 |
| Compound KB | $CH_3C(=O)NH—(CH_2)_2$— | $C_{27}H_{35}N_5O_6$ | 8.7, >75% | | 524 |
| Compound KC | 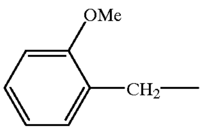 | $C_{21}H_{36}N_4O_6$ | 10.1, >95% | | 559 |

TABLE 11
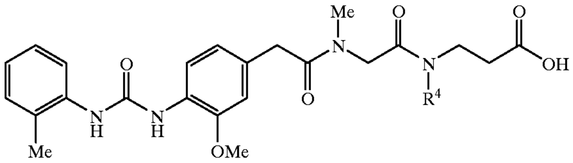
| Compound number | $R^4$ | MOLECULAR FORMULA | HPLC $R_T$ | $MH^+$ | $MH^-$ |
|---|---|---|---|---|---|
| Compound KD | 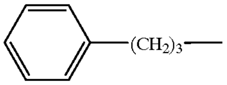 | $C_{32}H_{38}N_4O_6$ | 8.0, 100% | 575 | 573 |
| Compound KF | 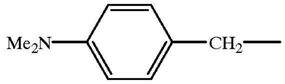 | $C_{32}H_{39}N_5O_6$ | 2.8, 100% | | 588 |
TABLE 12
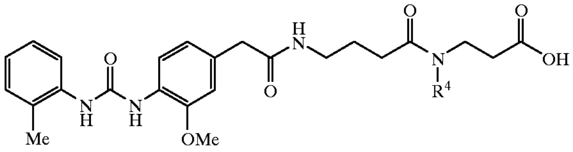
| Compound number | $R^4$ | MOLECULAR FORMULA | HPLC $R_T$ | $MH^+$ | $MH^-$ |
|---|---|---|---|---|---|
| Compound KG | 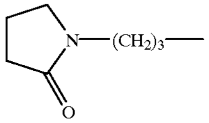 | $C_{31}H_{41}N_5O_7$ | 2.7, 95% | 596 | 594 |
| Compound KH | 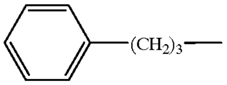 | $C_{33}H_{40}N_4O_6$ | 7.6, 97% | | 588 |
| Compound KI | 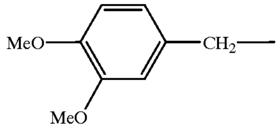 | $C_{33}H_{40}N_4O_8$ | 5.8, 83% | | 620 |
| Compound KJ | 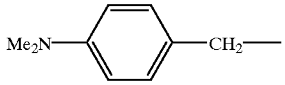 | $C_{33}H_{41}N_5O_6$ | 2.5, 97% | | 602 |

TABLE 13
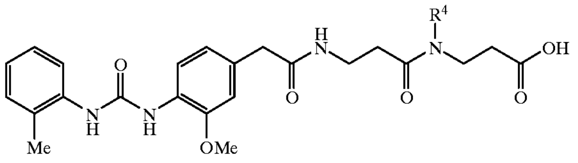
| Compound number | $R^4$ | MOLECULAR FORMULA | HPLC $R_T$ | $MH^+$ | $MH^-$ |
|---|---|---|---|---|---|
| Compound KK | 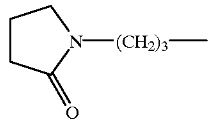 | $C_{30}H_{39}N_5O_7$ | 2.7, 96% | 582 | 580 |
| Compound KL | 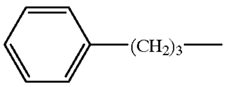 | $C_{32}H_{38}N_4O_6$ | 7.5, 97% | 575 | 573 |
| Compound KM | 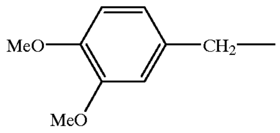 | $C_{32}H_{38}N_4O_8$ | 5.9, 70% | 607 | |
| Compound KN | 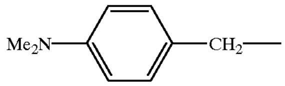 | $C_{32}H_{39}N_5O_6$ | 2.4, 93% | 590 | |
TABLE 14
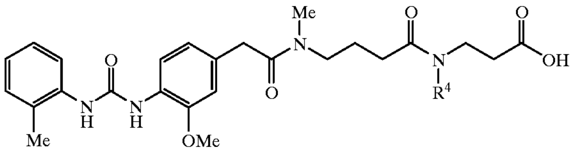
| Compound number | $R^4$ | MOLECULAR FORMULA | HPLC $R_T$ | $MH^+$ | $MH^-$ |
|---|---|---|---|---|---|
| Compound KO | 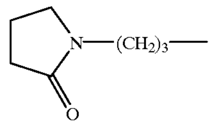 | $C_{32}H_{43}N_5O_7$ | 3.0, 100% | 610 | 609 |
| Compound KP | 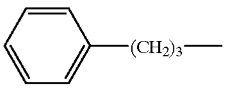 | $C_{34}H_{42}N_4O_6$ | 8.0, 85% | 603 | |
| Compound KQ | 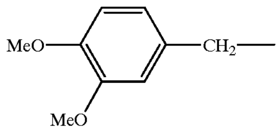 | $C_{34}H_{42}N_4O_8$ | 6.3, 65% | 635 | |

TABLE 14-continued

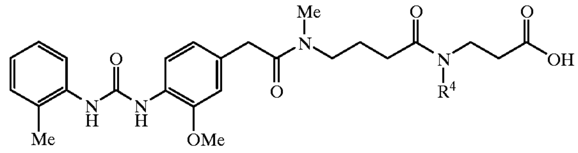

| Compound number | $R^4$ | MOLECULAR FORMULA | HPLC $R_T$ | $MH^+$ | $MH^-$ |
|---|---|---|---|---|---|
| Compound KR | 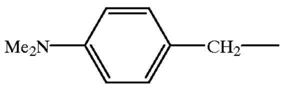 | $C_{34}H_{43}N_5O_6$ | 2.6, 90% | 618 | |

TABLE 15

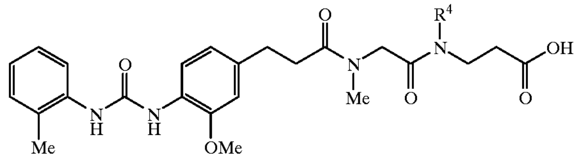

| Compound number | $R^4$ | MOLECULAR FORMULA | HPLC $R_T$ | $MH^+$ | $MH^-$ |
|---|---|---|---|---|---|
| Compound KS | 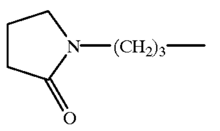 | $C_{21}H_{41}N_5O_7$ | 3.7, 96% | | 595 |
| Compound KT | 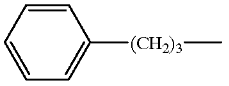 | $C_{33}H_{40}N_4O_6$ | 8.4, 100% | 590 | 587 |
| Compound KU | 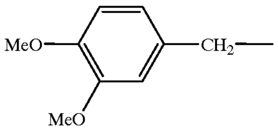 | $C_{33}H_{40}N_4O_8$ | 6.8, 100% | 621 | |
| Compound KV | 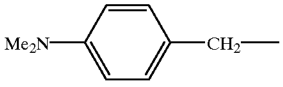 | $C_{33}H_{41}N_5O_6$ | 3.0, 88% | | 603 |

EXAMPLE 5

Compounds C, KW and KX

A solution of 3-{(3,4-dimethoxy-benzyl)-[({[3-methoxy-4-(3-o-tolylureido)phenyl]-acetyl}-N-methylamino)-acetyl]-amino}-propionic acid ethyl ester [2.0 g, Reference Example 4(a)] in ethanol (50 ml) was treated with sodium hydroxide (3.5 ml, 1M). After stirring at room temperature for 3 hours the mixture was concentrated to dryness. The residue was dissolved in water (12 ml) and the pH of the solution was adjusted to 1.0 by addition of concentrated hydrochloric acid (0.25 ml) and then extracted three times with dicliloromethiane. The resultant solid was collected and recrystallised twice from 20% aqueous isopropanol to give 3-{(3,4-dimethoxy-benzyl)-[({[3-methoxy-4-(3-o-tolylureido)phenyl]-acetyl}-N-methylamino)-acetyl]-amino}-propionic acid (Compound C) as a white solid (0.25 g,), m.p. 183–187° C.

[Elemental analysis:- C,63.2; H,6.3; N,9.2% Calculated for $C_{32}H_{38}N_4O_8$:- C,63.4; H,6.3; N,9.2%].

MS: 605 $[MH]^-$. HPLC: $R_T$=11.92 minutes (gradient clution using a mixture of acetonitrile and water 1:4 to 4:1).

(b) By proceeding in a manner similar to Example 5(a) but using 3-{[({[3-methoxy-4-(3-o-tolylureido)phenyl]-acetyl}-N-methylamino)-acetyl]-(3-carboxy-prop-1-yl)-amino}-propionic acid ethyl ester [Reference Example 4(b)] there was prepared 3-{[({[3-methoxy-4-(3-o-tolylureido)phenyl]- acetyl}-N-methylamino)-acetyl]-(3-carboxy-prop-1-yl)-amino}-propionic acid (Compound KW) as a white foam. [Elemental analysis:- C,57.2; H,6.5; N,9.9%. Calculated for $C_{27}H_{34}N_4O_8.H_2O$:- C,57.2; H,6.3; N,9.8%]. MS: 543 $[MH]^+$.

(c) By proceeding in a manner similar to Example 5(a) but 3-{[({[3-methoxy-4-(3-o-tolylureido)phenyl]-acetyl}-N-methylamino)-acetyl]-[2-(2-oxo-pyrrolidin-1-yl)-ethyl]-amino}-propionic acid ethyl ester [Reference Example 4(c)] there was prepared 3-{[({[3-methoxy-4-(3-o-tolylureido) phenyl]-acetyl}-N-methylamino)-acetyl]-[2-(2-oxo-pyrrolidin-1-yl)-ethyl]-amino}-propionic acid (Compound KX) as a yellow foam. [Elemental analysis:- C,59.5; H,6.5; N,11.9%. Calculated for $C_{29}H_{37}N_5O7.H_2O$:- C,59.5; H,6.7; N,11.95%]. MS: 568 $[MH]^+$.

EXAMPLE 6

Compounds BD, D, LA, LB, LC, AO, AC and LD to LH (a) Step 1. A solution of ({[3-methoxy-4-(3-o-tolylureido) phenyl]-acetyl}-amino)-acetic acid [50 g, Reference Example 3] and 3-(3,4-dimethoxy-benzylamino)-propionic acid ethyl ester [36 g, Reference Example 2(a)] in dimethylformamide (500 ml) was treated with [O-(7-azabenzotriazol-1-yl)-1,1,3,3,-tetramethyluronium hexafluorophosphate] (53.2 g) and diisopropylethylamine (59 ml). After stirring at ambient temperature for 3 hours the reaction mixture was evaporated to dryness and the residue was treated with water (3L). The mixture was extracted twice with ethyl acetate (1L) and then concentrated to dryness. The residue was subjected to flash chromatography on silica eluting initially with ethyl acetate and then with a mixture of ethyl acetate and methanol (9:1, v/v) to give 3-[N-(3,4-dimethoxybenzyl)-2-{2-[3-methoxy-4-(3-o-tolylureido)phenyl]acetylamino}acetamido]propionic acid ethyl ester as a yellow oil (49 g).

Step 2. This material was treated with methanol (1L) and sodium hydroxide (160 ml, 1.0M) and the reaction mixture was heated at 40° C. for 2 hours. After this time, the reaction mixture was cooled then evaporated and then treated with water (1.5L). The aqueous solution was washed twice with ethyl acetate (500 ml) and then acidified to pH 1.0 by addition of concentrated hydrochloric acid. The resultant solid was collected, washed with water and dried under vacuum. This material was recrystallised from 10% aqueous methanol to give 3-[N-(3,4-dimethoxy-benzyl)-2-{2-[3-methoxy-4-(3-o-tolylureido)phenyl]acetylamino}-acetamido]propionic acid (Compound BD) as a white solid (33 g), m.p. 172-174° C. [Elemental analysis:- C,62.4; H,6.2; N,9.5%. Calculated for $C_{31}H_{36}N_4O_8$:- C,62.8; H,6.1; N,9.4%.

MS: 593 $[MH]^+$.

(b) By proceeding in a manner similar to Example 6(a) but using 3-(3-imidazol-1-yl-prop-1-ylamino)-propionic acid ethyl ester [Reference Example 2(b)] to replace 3-(3,4-dimethoxy-benzylamino)-propionic acid ethyl ester, there was prepared 3{(3-imidazol-1-yl-prop-1-yl)-[({[3-methoxy-4-(3-o-tolylureido)phenyl]-acetyl}-amino)-acetyl]-amino}-propionic acid (Compound BK) as a white foam. MS: 551 $[MH]^+$.

(c) By proceeding in a manner similar to Example 6(a) but using 3-[3-(2-oxo-pyrrolidin-1-yl)-prop-1-ylamino]-propionic acid ethyl ester [Reference Example 2(c)] to replace 3-(3,4-dimethoxy-benzylamino)-propionic acid ethyl ester, there was prepared 3-{[({[3-methoxy-4-(3-o-tolylureido)phenyl]-acetyl}-amino)-acetyl]-[3-(2-oxo-pyrrolidin-1-yl)-prop-1-yl]-amino}-pronionic acid (Compound D) as a white foam. [Elemental analysis:- C,58.9; H,6.2; N,11.5%. Calculated for $C_{29}H_{37}N_5O_7.H_2O$:- C,59.5; H,6.7; N,11.95%]. MS: 586 $[MH]^+$.

(d) By proceeding in a manner similar to Example 6(a) but using 3-(3-carboxy-prop-1-ylamino)-propionic acid di-ethyl ester [Reference Example 2(d)] to replace 3-(3,4-dimethoxy-benzylamino)-propionic acid ethyl ester, there was prepared 3-{[({[3-methoxy-4-(3-o-tolylureido)phenyl]-acetyl}-amino)-acetyl]-(3-carboxy-prop-1-yl)-amino}-propionic acid (Compound LA) as a white solid, m.p. 179–181° C. [Elemental analysis:- C,59.0; H,6.1; N,10.55%. Calculated for $C_{26}H_{32}N_4O_8$:- C,59.1; X,6.1; N,10.6%]. MS: 529 $[MH]^+$.

(e) By proceeding in a manner similar to Example 6(a) but using 3-[2-(2oxo-pyrrolidin-1-yl)-ethylamino]-propionic acid ethyl ester [Reference Example 2(c)] to replace 3-(3,4-dimethoxy-benzylamino)-propionic acid ethyl ester, there was prepared 3-{[({[3-methoxy- 4-(3-o-tolylureido) phenyl]-acetyl}-amino)-acetyl]-[2-(2-oxo-pyrrolidin-1-yl)-ethyl]-amino}-propionic acid (Compound LB) as a white foam. [Elemental analysis:- C,58.2; H,6.5; N,12.0% Calculated for $C_{28}H_{35}N_5O_7.H_2O$:- C,58.8; H,6.5; N,12.25%]. MS: 553 $[MH]^+$.

(f) By proceeding in a manner similar to Example 6(a) but using 3-(2-carboxy-ethylamino)-propionic acid di-ethyl ester [Reference Example 2(f)] to replace 3-(3,4-dimethoxy-benzylamino)-propionic acid ethyl ester, there was prepared 3-{[({[3-methoxy-4-(3-o-tolylureido)phenyl]-acetyl}-amino)-acetyl]-(2-carboxy-ethyl)-amino}-propionic acid (Compound LC) as a white solid, m.p. 117–121° C. [Elemental analysis:- C,56.5; H,5.85; N,10.6% Calculated for $C_{25}H_{30}N_4O_8.H_2O$:- C,56.4; H,6.1; N,10.5%]. MS: 533 $[MH]^+$.

(g) By proceeding in a manner similar to Example 6(a) but using 3-(2,3-dimethoxy-benzylamino)-propionic acid ethyl ester [Reference Example 2(g)] to replace 3-(3,4-dimethoxy-benzylamino)-propionic acid ethyl ester, there was prepared 3-{(2,3-dimethoxy-benzyl)-[({[3-methoxy-4-(3-o-tolylureido)phenyl]-acetyl}-amino)-acetyl]-amino}-propionic acid (Compound AO) as a white solid, m.p. 134–136° C. [Elemental analysis:- C,63.0; H,6.6; N,9.6% Calculated for $C_{31}H_{36}N_4O_8$:- C,62.8; H,6.1; N,9.45%]. MS: 593 $[MH]^+$.

(h) By proceeding in a manner similar to Example 6(a) but using 3-(3-phenyl-prop-1-ylamino)-propionic acid ethyl ester [Reference Example 2(h)] to replace 3-(3,4-dimethoxy-benzylamino)-propionic acid ethyl ester, there was prepared 3-{[({[3-methoxy-4-(3-o-tolylureido)phenyl]-acetyl}-amino)-acetyl]-(3-phenyl-prop-1-yl)-amino}-propionic acid (Compound AC) as a white solid, m.p. 149–150° C. (Elemental analysis:- C,65.65; H,6.1; N,9.7% Calculated for $C_{31}H_{36}N_4O_6$:- C,66.4; H,6.5; N,10.0%]. MS: 561 $[MH]^+$.

(i) By proceeding in a manner similar to Example 6(a) but using 3-(phenylamino)-propionic acid ethyl ester (prepared according to the procedure described by Kano, Shinzo; Ebata, Tsutomu; Sliibuya, Shiroshi. J. Chem. Soc., Perkin Trans. 1 (1980), Issue 10. 2105-11) to replace 3-(3,4-dimethoxy-benzylamino)-propionic acid ethyl ester, there was prepared 3-{[({[3-methoxy-4-(3-o-tolylureido)phenyl]-acetyl}-amino)-acetyl]-phenyl-amino}-propionic acid (Compound LD) as a beige solid. MS: 519 $[MH]^+$.

(k) By proceeding in a manner similar to Example 6(a) but using 3-(3-ethoxy-4-methoxy-benzylamino)-propionic acid ethyl ester [Reference Example 7(a)] to replace 3-( 3,4dimethoxy-benzylamino)-propionic acid ethyl ester, there was prepared 3-{(3-ethoxy-4-methoxy-benzyl)-[({[3-methoxy-4-(3-o-tolylureido)phenyl]-acetyl}-amino)-acetyl]-amino}-propionic acid (Compound LE) as a white solid, m.p. 187–189° C. [Elemental analysis:- C,63.1; H,6.5; N,9.2% Calculated for $C_{32}H_{38}N_4O_8$:- C,6335; H,6.3; N,9.2%]. MS: 607 $[MH]^+$.

(l) By proceeding in a manner similar to Example 6(a) but using 3-(3,4-diethoxy -benzylamino)-propionic acid ethyl ester [Reference Example 7(b)] to replace 3-(3,4-dimethoxy-benzylamino)-propionic acid ethyl ester, there was prepared 3-{(3,4-diethoxy-benzyl)-[({[3-methoxy-4-(3-o-tolylureido)phenyl]-acetyl}-amino)-acetyl]-amino}-propionic acid (Compound LF) as a white solid, m.p. 197–198° C. [Elemental analysis:- C,63.95; H,6.4; N,8.9% Calculated for $C_{33}H_{40}N_4O_8$:- C,63.9; H,6.5; N,9.0%]. MS: 621 $[MH]^+$.

(m) By proceeding in a manner similar to Example 6(a) but using 3-(4-benzyloxy-3-methoxy-benzylamino)-propionic acid ethyl ester [Reference Example 7(c)] to replace 3-(3,4-dimethoxy-benzylamino)-propionic acid ethyl ester, there was prepared 3-{(4-benzyloxy-3-methoxy-benzyl )-[({[3-methoxy-4-(3-o-tolylureido)phenyl]-acetyl}-amino)-acetyl]-amino}-propionic acid (Compound LG) as a white solid, m.p. 160–162° C. [Elemental analysis:- C,65.7; H,5.9; N,835% Calculated for $C_{37}H_{40}N_4O_8.0.26H_2O$:- C,66.0; H,6.1; N,8.3%]. MS: 669 $[MH]^+$.

(n) By proceeding in a manner similar to Example 6(a) but using 3-[(1,4-benzodioxan-6-yl)-methylamino]-propionic acid ethyl ester [Reference Example 7(d)] to replace 3-(3,4-dimethoxy-benzylamino)-propionic acid ethyl ester, there was prepared 3-{[(1,4-benzodioxan-6-yl)-methyl]-[({[3-methoxy-4-(3-o-tolylureido)phenyl]-acetyl}-amino)-acetyl]-amino}-propionic acid (Compound LH) as a white solid, m.p. 175–178° C. (with decomposition). [Elemental analysis:- C,62.0; H,6.1; N,9.5%. Calculated for $C_{31}H_{34}N_4O_8.0.55H_2O$:- C,62.0; H,5.9; MS: 591 $[MH]^+$.

EXAMPLE 7

Compound LI

Step1. By proceeding in a manner similar to step 1 of Example 6(a) but using 3-(3-tert-butoxycarbonylamino-prop-1-ylamino)-propionic acid ethyl ester (Reference Example 2(i)) to replace 3-(3,4-dimethoxy-benzylamino)-propionic acid ethyl ester, there was prepared 3-{[({[3-methoxy-4-(3-o-tolylureido)phenyl]-acetyl}-amino)-acetyl]-(3-tert-butoxycarbonylamino-prop-1-yl)-amino}-propionic acid ethyl ester.

Step2. A solution of this material (0.75 g) in dicliloromethane (10 ml) was treated with trifluoracetic acid (1.75 ml) and stirred at ambient temperature for 2.5 hours. The reaction mixture was evaporated to give 3-{[({[3-methoxy-4-(3-o-tolylureido)phenyl]-acetyl}-amino)-acetyl]-(3-amino-prop-1-yl)-amino}-propionic acid ethyl ester trifluoroacetate salt (1.0 g) which was treated with dichloromethane (10 ml). The resulting solution was cooled to 0° C. and then treated with triethylamine (1.8 ml) followed by methanesulphonyl chloride (0.1 ml). The reaction mixture was stirred for 3 hours at ambient temperature then diluted with dichloromethane (10 ml) and washed with hydrochloric acid (10 ml, 1M), then with water (10 ml), then with saturated sodium bicarbonate solution (10 ml) and then with brine. The organic layer was dried over magnesium sulphate and evaporated. The residue was subjected to flash chromatography on silica eluting with a mixture of ethyl acetate and methanol (9:1, v/v) to give a white foam (0.63 g). This material was hydrolysed according to the procedure described in step 2 of Example 3(a) to give 3-{[({[3-methoxy-4-(3-o-tolylureido)phenyl]-acetyl }-amino)-acetyl]-(3-methanesulphonylamino-prop-1-yl)-amino}-pronionic acid (Compound LI) as a colourless foam (0.43 g). MS: 578 $[MH]^+$.

EXAMPLE 8

Compounds LJ to MD

By proceeding in a similar manner to Example 3, but using the appropriately substituted amines in step 2 and ({[3-methoxy-4-(3-o-tolylureido)phenyl]-acetyl}-N-methylamino)-acetic acid (Reference Example 1) or ({[3-methoxy-4-(3-o-tolylureido)phenyl]-acetyl}-amino)-acetic acid (Reference Example 3) in step 3 there were prepared Compounds Lj to MD depicted in Table 16.

TABLE 16

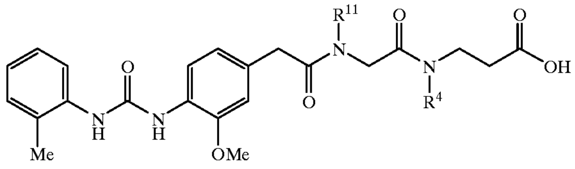

| Compound number | $R^{11}$ | $R^4$ | MOLECULAR FORMULA | $MH^+$ | $MH^-$ |
|---|---|---|---|---|---|
| Compound LJ | H | 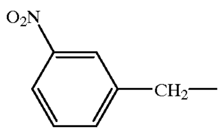 | C29H31N5O8 | 578 | 576 |
| Compound LK | $CH_3$ | 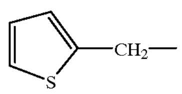 | C28H32N4O6S | | |

TABLE 16-continued
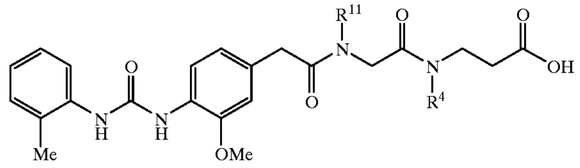
| Compound number | $R^{11}$ | $R^4$ | MOLECULAR FORMULA | $MH^+$ | $MH^-$ |
|---|---|---|---|---|---|
| Compound LL | $CH_3$ | 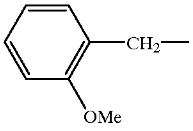 | C31H36N4O7 | 577 | 575 |
| Compound LM | $CH_3$ | 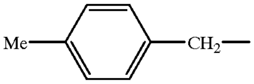 | C31H36N4O6 | 561 | 559 |
| Compound LN | $CH_3$ | 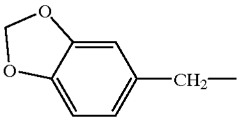 | C31H34N4O8 | 591 | 589 |
| Compound LO | $CH_3$ | 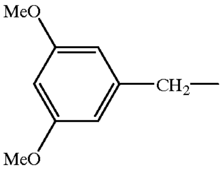 | C32H38N4O8 | 607 | 605 |
| Compound LP | H | 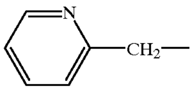 | C28H31N5O6 | 534 | 532 |
| Compound LQ | $CH_3$ | 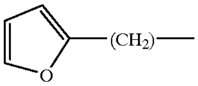 | C28H32N4O7 | 537 | 535 |
| Compound LR | $CH_3$ | 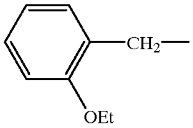 | C32H38N4O7 | 591 | 589 |
| Compound LS | H | 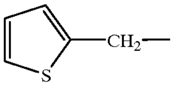 | C27H30N4O6S | 539 | 537 |
| Compound LT | H | 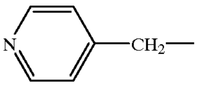 | C28H31N5O6 | 534 | 532 |
| Compound LU | $CH_3$ | 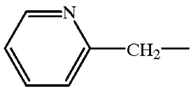 | C29H32N5O6 | 548 | 546 |

TABLE 16-continued

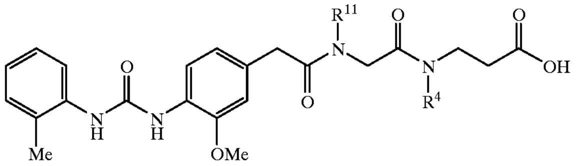

| Compound number | $R^{11}$ | $R^4$ | MOLECULAR FORMULA | $MH^+$ | $MH^-$ |
|---|---|---|---|---|---|
| Compound LV | $CH_3$ | 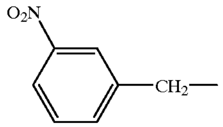 | C30H33N5O8 | 592 | |
| Compound LW | $CH_3$ | 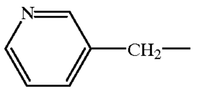 | C29H33N5O6 | 548 | 546 |
| Compound LX | $CH_3$ | 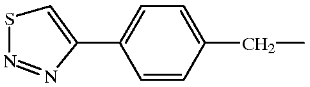 | C32H34N6O6S | 631 | 629 |
| Compound LY | $CH_3$ | 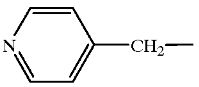 | C29H33N5O6 | 548 | 546 |
| Compound LZ | $CH_3$ | 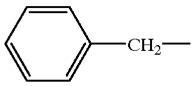 | C30H34N4O6 | 547 | 545 |
| Compound MA | $CH_3$ | 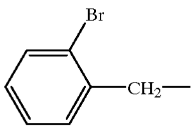 | C30H33BrN4O6 | | 624 |
| Compound MB | H | 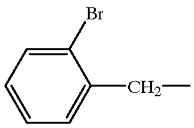 | C29H31BrN4O6 | 613 | 611 |
| Compound MC | $CH_3$ | 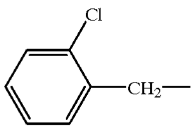 | C30H33ClN4O6 | 581 | 579 |
| Compound MD | $CH_3$ | 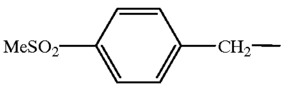 | C31H36N4O8S | 625 | 623 |

EXAMPLE 9

(a) 3-{(3,4-Dimethoxy-benzyl)-[({[3-methoxy-4-(3-o-tolylureido)phenyl]-acetyl}-N-methylamino)-acetyl]-amino}-propionic acid sodium salt A solution of 3-{(3,4-dimethoxy-benzyl)-[({[3-methoxy-4-(3-o-tolylureido)phenyl]-acetyl}-N-methylamino)-acetyl]-amino}-propionic acid [17 g, Example 5(a)] in ethanol (170 ml) was treated with sodium hydroxide solution (23.3 ml, 1N). After stirring at ambient temperature for 24 hours the reaction mixture was filtered through a short pad of diatomaceous earth and then evaporated. The residue was triturated with hot ethyl acetate (200 ml) and dried under vacuum. The resultant foam was dissolved in water (200 ml) and freeze dried for 40 hours to yield the title compound as a white solid (15.4 g), m.p. 225° C. (with decomposition).

[Elemental analysis:- C,57.8; H,6.05; N,8.2; Na,3.5%. Calculated for $C_{32}H_{37}N_4NaO_8.2H_2O$:- C,57.8; H,6.2; N,8.4; Na,3.5%].

(b) By proceeding in a manner similar to Example 9(a) but using 3-{[({[3-methoxy-4-(3-o-tolylureido)phenyl]-acetyl}-N-methylamino)-acetyl]-[3-(2-oxo-pyrrolidin-1-yl)-prop-1-yl]-amino}-propionic acid [Example 1(a)], there was prepared 3-{[({[3-methoxy-4-(3-o-tolylureido)phenyl]-acetyl}-N-methylamino)-acetyl]-[3-(2-oxo-pyrrolidin-1-yl)-prop-1-yl]-amino}-propionic acid sodium salt. m.p. 213° C. (with decomposition). [Elemental analysis:- C,57.55; H,6.4; N,10.85; Na,3.5% Calculated for $C_{30}H_{38}N_5NaO_7.H_2O$:- C.57.95; H,6.5; N,11.25; Na,3.7%].

(c) By proceeding in a manner similar to Example 9(a) but using $^3$-{(3,4-dimethoxy-benzyl)-[({[3-methoxy-4-(3-o-tolylureido)-phenyl]-acetyl}-amino)-acetyl]-amino}-propionic acid [Example 6(a)], there was prepared 3-{[({[3-methoxy-4-(3-o-tolylureido)-phenyl]-acetyl}-amino)-acetyl]-[3-(2-oxo-pyrrolidin-1-yl)-prop-1-yl]-amino}-propionic acid sodium salt, m.p. >250° C. (with decomposition).

REFERENCE EXAMPLE 1

({[3-Methoxy-4-(3-o-tolylureido)phenyl]-acetyl}-N-methylamino)-acetic acid

A solution of [3-methoxy-4-(3-o-tolylureido)phenyl]-acetic acid (2.50 g, Reference Example 5) and sareosine ethyl ester hydrochloride(1.23 g) in dimethylformamide (75 ml) was treated with [O-(7-azabenzotriazol-1-yl)-1,1,3,3,-tetramethyluronium hexafluorophosphate] (3.03 g) and diisopropylethylamine (430 ml). The reaction mixture was stirred at room temperature for 2 hours, then treated with water (200 ml) and then filtered. The white solid was suspended in tetrahydrofuran (100 ml) and the mixture was then treated with lithium hydroxide hydrate (0.45 g) in water (20 ml). After stirring for 45 minutes the mixture was concentrated to remove the tetrahydrofuran. The remaining aqueous phase was washed with ethyl acetate then acidified by addition of hydrochloric acid (1M), then extracted three times with ethyl acetate. The combined organic extracts were washed with brine, then dried over magnesium sulphate and then evaporated to yield the title compound (2.24 g) as a white solid, m. p. 125–130° C. (with decomposition). HPLC: $R_T$=10.83 minutes (gradient elution using a mixture of acetonitrile and water 1:4 to 4:1 v/v). MS(-ve) $[M-1]^-$ 384.

REFERENCE EXAMPLE 2

(a) 3-(3,4-dimethoxy-benzylamino)-propionic acid ethyl ester

A mixture of 3,4-dimethoxy-benzylamine (100 g) and ethyl acrylate (65 ml) in ethanol (2L) and cylcohexane (1L) was stirred at room temperature for 20 hours then evaporated to give the title compound as a colourless oil (154 g). MS: 268 $[MH]^+$.

(b) By proceeding in a manner similar to Reference Example 2(a) but using 1-(3-aminoprop-1-yl)-imidazole there was prepared 3-(3-imidazol-1-yl-prop-1-ylamino)-propionic acid ethyl ester. MS: 226 $[MH]^+$.

(c) By proceeding in a manner similar to Reference Example 2(a) but using 1-(3-aminoprop-1-yl)-2-pyrrolidinone there was prepared 3-[3-(2-oxo-pyrrolidin-1-yl)-prop-1-ylamino]-propionic acid ethyl ester. MS: 243 $[MH]^+$.

(d) By preceding in a manner similar to Reference Example 2(a) but using 4-amino-butanoic acid ethyl ester there was prepared 3-(3-carboxy-prop-1-ylamino)-propionic acid di-ethyl ester.

(e) By proceeding in a manner similar to Reference Example 2(a) but using 1-(2-aminoethyl)-2-pyrrolidin none there was prepared, 3-[2-(2-oxo-pyrrolidin-1-yl)-ethylamino]-propionic acid ethyl ester.

(f) By proceeding in a manner similar to Reference Example 2(a) but using β-alanine ethyl ester there was prepared 3-(2-carboxy-ethylamino)-propionic acid di-ethyl ester.

(g) By proceeding in a manner similar to Reference Example 2(a) but using 2,3-dimethoxy-benzylamine, there was prepared 3-(2.3-dimethoxy-benzylamino)-propionic acid ethyl ester.

(h) By proceeding in a manner similar to Reference Example 2(a) but using 3-phenyl-prop-1-ylamine, there was prepared 3-(3-phenyl-prop-1-ylamino)-propionic acid ethyl ester.

(i) By proceeding in a manner similar to Reference Example 2(a) but using 3-(tert-butoxycarbonylamino)prop-1-ylamine (prepared according to the procedure described by Muller, Dan; Zeltser, I rena; Bitan, Gal; Gilon, Chaim. J. Org. Chem. 1997, 62, page 411–416), there was prepared 3-(3-tert-butoxycarbonylamino-prop-1-ylamino)-propionic acid ethyl ester.

REFERENCE EXAMPLE 3

({[3-Methoxy-4-(3-o-tolylureido)phenyl]-acetyl}-amino)-acetic acid

A stirred solution of [3-methoxy-4-(3-o-tolylureido) phenyl]-acetic acid (7.53 g, Reference Example 5) in a mixture of dimethylformamide (15 ml) and dichloromethane (150 ml) was treated with 1-(3-dimethylaminoprop-1-yl)-3-ethylcarbodiimide (4.98 g), then with 1-hydroxybenzotriazole (3.57 g), then with glycine methyl ester hydrochloride (3.01 g) and then with diisopropylethylamine (4.10 ml). After stirring at room temperature for 20 hours the reaction mixture was diluted with water (100 ml). The organic phase was washed with saturated sodium bicarbonate (100 ml), then with hydrochloric acid (1M) and then with brine, then dried over magnesium sulphate and then evaporated. The residue was triturated with petroleum ether and the resulting cream coloured solid (6.25 g) was dissolved in tetrahydrofuran (200 ml). The solution was treated with water (50 ml) and then with lithium hydroxide hydrate (0.75 g). The mixture was stirred at room temperature for 4 hours and then the tetrahydrofuran was removed under vacuum. The aqueous phase was acidified by addition of hydrochloric acid (12M). The resulting solid was washed with diethyl ether and then dried to give the title compound (5.76 g), m. p. 130–134° C. (with decomposition). MS: 370 $[M-1]^-$. HPLC: $R_T$=10.16 minutes (gradient clution using a mixture of acetonitrile and water 4:1 to 1:4 v/v).

REFERENCE EXAMPLE 4

(a) 3-{(3,4-Dimethoxy-benzyl)-[({[3-methoxy-4-(3-o-tolylureido)phenyl]-acetyl}-N-methylamino)-acetyl]-amino}-propionic acid ethyl ester A solution of ({[3-methoxy-4-(3-o-tolylureido)phenyl]-acetyl}-N-methylamino)-acetic acid [18.4 g, Reference Example 1] and 3-(3,4-dimethoxy-benzylamino)-propionic acid ethyl ester [13.4 g, Reference Example 2(a)] in dimethylformamide (400 ml) was treated with [O-(7-azabenzotriazol-1-yl)-1,1,3,3,-tetramethyluronium hexafluorophosphate] (19.1 g) and diisopropylethylamine (10.5 ml). After stirring at ambient temperature for 20 hours the reaction mixture was evaporated to dryness. The residue was treated with water (800 ml) followed by hydrochloric acid (175 ml 1 M) and the mixture was extracted twice with ethyl acetate (500 ml). The combined organic extracts were washed with hydrochloric acid (500 ml, 1M), then with water (400 ml), then with saturated aqueous sodium bicarbonate solution (500 ml), then dried over magnesium sulphate and then evaporated. The residual oil was subjected to flash chromatography on silica eluting with a mixture of dichloromethane and methanol (49:1, v/v) to give the title compound as a fawn coloured foam (26.4 g), m.p. 97–105° C. [Elemental analysis:- C,63.4; H,6.7; N,8.7% Calculated for $C_{34}H_{42}N_4O_8.0.5H_2O$:- C,63.3; H,6.8; N,8.8%].

(b) By proceeding in a manner similar to Reference Example 4(a) but using 3-(3-carboxy-prop-1-ylamino)-propionic acid di-ethyl ester [Reference Example 2(d)] to replace 3-(3,4-dimethoxy-benzylamino)-propionic acid ethyl ester, there was prepared 3-{[({[3-methoxy-4-(3-o-tolylureido)phenyl]-acetyl}-N-methylamino)-acetyl]-(3-carboxy-prop-1-yl)-amino}-propionic acid ethyl ester.

(c) By proceeding in a manner similar to Reference Example 4(a) but using 3-[2-(2-oxo-pyrrolidin-1-yl)-ethylamino]-propionic acid ethyl ester [Reference Example 2(e)] to replace 3-(3,4-dimethoxy-benzylamino)-propionic acid ethyl ester, there was prepared 3-{[({[3-methoxy-4-(3-o-tolylureido)phenyl]-acetyl}-N-methylamino)-acetyl]-[2-(2-oxo-pyrrolidin-1-yl)-ethyl]-amino}-propionic acid ethyl ester.

REFERENCE EXAMPLE 5

[3-Methoxy-4-(3-o-tolylureido)phenyl]acetic acid

A suspension of [3-methoxy-4-(3-o-tolylureido)phenyl]-acetic acid methyl ester (19.43 g, Reference Example 6) in methanol (195 ml) was treated with sodium hydroxide solution (65 ml, 1N) and the mixture was heated at reflux for 1 hour giving a clear solution. The reaction mixture was cooled to room temperature and then filtered. The filtrate was diluted to 390 ml with water, then heated to 50° C. and then acidified to pH 1 by the addition of hydrochloric acid (80 ml, 1N) over 1 hour. The resulting suspension was stirred for a further 30 minutes at 50° C., then allowed to cool to room temperature and then filtered. The solid was washed with twice with water (200 ml) then dried to give the title compound (15.72 g) as a white solid, m. p. 179–181° C. (with decomposition).

REFERENCE EXAMPLE 6

[3-methoxy-4-(3-o-tolylureido)phenyl]-acetic acid methyl ester

A suspension of potassium t-butoxide (1.44 kg) in dimethylformamide(6.61), cooled to −5° C. to −10° C., was treated with a mixture of 2-nitroanisole (690 g) and methyl dichloroacetate (915 g) over 4 hours, whilst maintaining the temperature below −5° C. The reaction mixture was then treated with acetic acid (770 ml), then with water (6.6 l) and then extracted three times with tert-butyl methyl ether (5.5 l). The combined extracts were washed with water (5.5 l), then with saturated sodium bicarbonate solution (5.5 l), then with saturated brine (5.5 l) and then dried over magnesium sulphate to give a solution of methyl α-chloro-3-methoxy-4-nitrophenylacetate. This solution was concentrated to half volume under reduced pressure and then treated with tetrahydrofuran (21), followed by triethylamine (751 ml), followed by 10 % palladium on chareoal (58.4 g) and the mixture was hydrogenated under a pressure of 50 psi hydrogen at 50° C. for 8 hours. The mixture was cooled to room temperature and filtered. The filtrate was dried over magnesium sulphate to give a solution of methyl 4-amino-3-methoxyphenylacetate which was heated to reflux and then treated with o-tolyl isocyanate (598.5 g) over 30 minutes. After heating at reflux temperature for a further 3 hours, during which time a solid was deposited, the mixture was cooled to room temperature. The solid was collected, washed twice with tert-butyl methyl ether (4 l), then dried in a vacuum oven at 60° C. to give the title compound (764.8 g) as a white solid, m.p. 167–168° C.

REFERENCE EXAMPLE 7

(a) 3-(3-Ethoxy-4-methoxy-benzylamino)-propionic acid ethyl ester

A mixture of β-alanine ethyl ester hydrochloride (1.6 g), 3-ethoxy-4-methoxybenzaldehyde (1.8 g), sodium cyanoborohydride (0.42 g) and powdered 3Å molecular seives (2.5 g) in ethanol (25 ml) was stirred at ambient temperature for 24 hours. A further aliquot of sodium cyanoborohydride (0.42 g) was added and stirring was continued for a further 24 hours. The reaction mixture was filtered and the filtrate was evaporated. The residue was treated with ethyl acetate (100 ml) and the solution was washed with 10% aqueous potassium carbonate (50 ml), then twice with water (25 ml), then with brine (25 ml), then dried over magnesium sulphate and then evaporated. The residual oil was subjected to flash chromatography on silica eluting with a mixture of dichloromethane and methanol (95:5, v/v) to give the title compound as a colourless oil (1.1 g).

(b) By proceeding in a manner similar to Reference Example 7(a) but using 3,4-diethoxy-benzaldehyde, there was prepared 3-(3.4-diethoxy-benzylamino)-propionic acid ethyl ester.

(c) By proceeding in a manner similar to Reference Example 7(a) but using 4-benzyloxy-3-methoxy-benzaldehyde, there was prepared 3-(4-benzyloxy-3-methoxy-benzylamino)-propionic acid ethyl ester.

(d) By proceeding in a manner similar to Reference Example 7(a) but using 1,4-benzodioxan-6-carboxaldehyde, there was prepared 3-r(1,4-benzodioxan-6-yl)-methylamino-propionic acid ethyl ester.

IN VITRO AND IN VIVO TEST PROCEDURES

1. Inhibitory effects of compounds on VLA4 dependent cell adhesion to Fibronectin and VCAM.

1.1 Metabolic labelling of RAMOS cells.

RAMOS cells (a pre-B cell line from ECACC, Porton Down, UK) are cultured in RPMI culture medium (Gibco, UK) supplemented with 5% foetal calf serum (FCS, Gibco, UK). Prior to assay the cells are suspended at a concentration of $0.5\times10^6$ cells/ml RPMI and labelled with 400 μCi/100 mls of [$^3$H]-methionine (Amersham, UK) for 18 hours at 37° C.

1.2 96 well plate preparation for adhesion assay.

Cytostar plates (Amersham, UK) were coated with 50 μl/well of either 3 μg/ml human soluble VCAM-1 (R&D Systems Ltd, UK) or 28.8 μg/ml human tissue Fibronectin (Sigma, UK). In control non-specific binding wells 50 μl phosphate buffered saline was added. The plates were then left to dry in an incubator at 25° C., overnight. The next day the plates were blocked with 200 μl/well of Pucks buffer (Gibco, UK) supplemented with 1% BSA (Sigma, UK). The plates were left at room temperature in the dark for 2 hours. The blocking buffer was then disposed of and the plates dried by inverting the plate and gently tapping it on a paper tissue. 50 μl/well of 3.6% dimethyl sulphoxide in Pucks buffer supplemented with 5 mM manganese chloride (to activate the integrin receptor Sigma, UK) and 0.2% BSA (Sigma, UK), was added to the appropriate control test binding and non-specific binding assay wells in the plate. 50 μl/well of the test compounds at the appropriate concentrations diluted in 3.6% dimethyl sulphoxide in Pucks buffer supplemented with 5 mM manganese chloride and 0.2% BSA, was added to the test wells.

Metabolically labelled cells were suspended at $4\times10^6$ cells/ml in Pucks buffer that was supplemented with manganese chloride and BSA as above. 50 $\mu$l/well of cells in 1.8% dimethyl sulphoxide in Pucks buffer and supplements was added to all plate wells. The same procedure exists for plates coated with either VCAM-1 or fibronectin and data is determined for compound inhibition of cell binding to both substrates.

1.3 Performance of assay and data analysis.

The plates containing cells in control or compound test wells are incubated in the dark at room temperature for 1 hour.

The plates are then counted on a Wallac Microbeta scintillation counter (Wallac, UK) and the captured data processed in Microsoft Excel (Microsoft, US). The data was expressed as an IC50, namely the concentration of inhibitor at which 50% of control binding occurs. The percentage binding is determined from the equation:

$$\{[(C_{TB}-C_{NS})-(C_I-C_{NS})]/(C_{TB}-C_{NS})\}\times100=\%\ \text{binding}$$

where $C_{TB}$ are the counts bound to fibronectin (or VCAM-1) coated wells without inhibitor present, $C_{NS}$ are the counts present in wells without substrate, and $C_I$ are the counts present in wells containing a cell adhesion inhibitor.

Compound data of this invention is expressed for $IC_{50}$s for inhibition of call adhesion to both fibronectin and VCAM-1.

2.4 Assessment of airway inflammation.

The cell accumulation in the lung is assessed 24 hours after challenge (rats) or 48–72 hours after challenge (mice). The animals are cuthanized with sodium pentobarbitone (200 mg/kg, i.p., Pasteur Merieux, France) and the trachea is immediately cannulated. Cells are recovered from the airway lumen by bronchoalveolar lavage (BAL) and from the lung tissue by enzymatic (collagenase, Sigma, UK) disaggregation as follows.

BAL is performed by flushing the airways with 2 aliquots (each 10 ml/kg) RPMI 1640 medium (Gibco, UK) containing 10% fetal calf serum (FCS, Serotec Ltd., UK). The recovered BAL aliquots are pooled and cell counts made as described below.

Immediately after BAL, the lung vasculature is flushed with RPMI 1640/FCS to remove the blood pool of cells. The lung lobes are removed and cut into 05 mm pieces. Samples (rats: 400 mg; mice: 150 mg) of homogenous lung tissue are incubated in RPMI 1640/FCS with collagenase (20 U/ml for 2 hours, then 60 U/ml for 1 hour, 37° C.) to disaggregate cells from the tissue. Recovered cells are washed in RPMI 1640/FCS.

Counts of total leukocytes recovered from the airway lumen and the lung tissue are made with an automated cell counter (Cobas Argos, US). Differential counts of eosinophils, neutrophils and mononuclear cells are made by light microscopy of cytocentrifuge preparations stained with Wright-Giemza stain (Sigma, UK). T cells are counted by flow cytometry (EPICS XL, Coulter Electronics, US) using fluophore-labelled antibodies against CD2 (a pan-T cell marker used to quantify total T cells), CD4, CD8 and CD25 (a marker of activated T cells). All antibodies were supphed by Serotec Ltd., UK)

2.5 Data analysis.

The cell data was expressed as mean cell numbers in unchallenged, challenged and vehicle treated, and challenged and compound treated groups, including the standard error of the means. Statistical analysis of the difference among treatment groups was evaluated using one-way analysis of variance via the Mann-Whitney test. Where $p<0.05$ no statistical significance existed. The inhibitors of the invention caused a statistically significant reduction in cosinophil and lymphocyte numbers in the BAL and airway tissue. The inhibitors of the invention caused a statistically significant reduction in eosinophil and lymphocyte numbers in the BAL and airway tissue at doses within the range 100 mg/kg to 0.01 mg/kg.

3. Inhibition of Antigen Induced Airway Sensitivity in Allergic Sheep

The experiment was performed essentially as described in W. M. Abraham et al, J. Clin. Invest., (1994) Vol 93, 776–787. The experiment used allergic sheep which had been previously shown to develop early and late phase responses to inhaled challenge with Ascaris sum antigen. The inhibitors of the invention were delivered as an aerosol to the sheep and caused a statistically significant reduction of Ascaris sum induced airway responses when dosed at 1 mg/kg.

What is claimed is:

1. A compound of general formula (I):

(I)

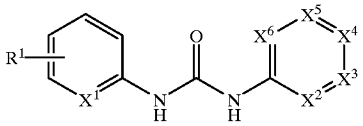

wherein:

$R^1$ is hydrogen, halogen, lower alkyl or lower alkoxy;

$X^1$, $X^2$ and $X^6$ independently represent N or $CR^2$; and one of $X^3$, $X^4$ and $X^5$ represents $CR^3$ and the others independently represent N or $CR^2$ where $R^2$ is hydrogen, halogen, lower alkyl or lower alkoxy; and $R^3$ represents a group $—L^1—(CH_2)_n—C(═O)—N(R^4)—CH_2—CH_2—Y$ in which:

$R^4$ is aryl or heteroaryl, or $R^4$ is alky, alkenyl, or alkynyl each optionally substituted by one or more groups selected from halo, oxo, $R^5$, $—C(═O)—R^7$, $—NH—C(═O)-R^7$ and $—C(═O)NY^1Y^2$, or $R^4$ is cycloalkenyl, cycloalkyl or heterocycloalkyl, each optionally substituted by one or more groups selected from oxo, $R^6$ and $—L^2—R^6$ ; where $R^5$ is an acidic functional group (or corresponding protected derivative), aryl, cycloalkyl, cycloalkenyl, heteroaryl, heterocycloalkyl, $—ZR^7$ or $—NY^1Y^2$; $R^6$ is an acidic functional group (or corresponding protected derivative), aryl, heteroaryl, heterocycloalkyl, —ZH, $—Z^1R^7$ or $—NY^1Y^2$; $R^7$ is alkyl, aryl, arylalkyl, cycloalkyl, cycloalkylalkyl, heteroaryl, heteroarylalkyl, heterocycloalkyl or heterocycloalkylalkyl;

$L^2$ is alkylene; $Y^1$ and $Y^2$ are independently hydrogen, acyl, alkyl [optionally substituted by hydroxy, heterocycloalkyl, or one or more carboxy or $—C(═O)—NHR^8$ groups (where $R^8$ is hydrogen or lower alkyl)], alkylsulphonyl, aryl, arylalkyloxycarbonyl, arylsulphonyl, arylalkyl, heteroaryl, heteroarylalkyl, heterocycloalkyl or heterocycloalkylalkyl; or the group $—NY^1Y^2$ may form a 5–7 membered cyclic amine which (i) may be optionally substituted with one or more substituents selected from carboxamido, carboxy, hydroxy, oxo, hydroxyalkyl, $HOCH_2CH_2—(OCH_2CH_2)_m—$ (where m is zero, or an integer selected from one and two), or alkyl optionally substituted by carboxy or carboxamido (ii) may also contain a further heteroatom selected from O, N, S or $SO_2$ and (iii) may also be fused to additional aromatic, heteroaromatic, heterocycloalkyl or cycloalkyl rings to form a bicyclic or tricyclic ring system; Z is O or S; and $Z^1$ is O or $S(O)_m$;

$L^1$ represents a —$R^9$—$R^{10}$— linkage, in which $R^9$ is a straight or branched $C_{1-6}$alkylene chain, a straight or branched $C_{2-6}$alkenylene chain or a straight or branched $C_{2-6}$alkynylene chain, and $R^{10}$ is a direct bond, cycloalkylene, heterocycloalkylene, arylene, heteroaryldiyl, —C(=Z)—$NR^{11}$—, —$NR^{11}$—C(=Z)—, $Z^1$—,—$NR^{11}$—, —C(=O)—, —C(=$NOR^{11}$)—, —$NR^{11}$—C(=Z)—$NR^{11}$—, —$SO_2$—$NR^{11}$—, —$NR^{11}$—$SO_2$—, —O—C(=O)—, —C(=O)—O—, —$NR^{11}$—C(=O)—O— or —O—C(=O)—$NR^{11}$— (where $R^{11}$ is a hydrogen atom or $R^4$); but excluding compounds where in said $L^1$ substituent an oxygen, nitrogen or sulphur atom is attached directly to a carbon carbon multiple bond;

Y is carboxy (or an acid bioisostere) or —C(=O)—$NY^1Y^2$; and n is an integer from 1 to 6;

and their prodrugs, and pharmaceutically acceptable salts and solvates of such compounds and their prodrugs.

2. A compound according to claim 1 in which $R^1$ represents hydrogen.

3. A compound according to claim 1 in which $X^1$ represents $CR^2$ where $R^2$ is $C_{1-4}$alkyl or $C_{1-4}$alkoxy.

4. A compound according to claim 3 in which $R^2$ is methyl.

5. A compound according to claim 1 in which $X^2$ represents $CR^2$ where $R^2$ is $C_{1-4}$alkyl or $C_{1-4}$alkoxy.

6. A compound according to claim 5 in which $R^2$ is methoxy.

7. A compound according to claim 1 in which $X^3$ represents CH.

8. A compound according to claim 1 in which $X^6$ represents CH.

9. A compound according to claim 1 in which one of $X^4$ and $X^5$ represents $CR^3$ and the other represents CH.

10. A compound according to claim 9 in which within $R^3$ the moiety $L^1$ represents a —$R^9$—$R^{10}$— linkage wherein $R^9$ represents a straight or branched $C_{1-6}$alkylene chain and $R^{10}$ represents —C(=O)—$NR^{11}$ where $R^{11}$ is selected from one of the following groups:

(i) hydrogen;

(ii) $C_{1-6}$alkyl;

(iii) $C_{1-6}$alkyl substituted by $R^5$, where $R^5$ is aryl;

(iv) $C_{1-6}$alkyl substituted by $R^5$, where $R^5$ is heteroaryl;

(v) $C_{1-6}$alkyl substituted by $R^5$, where $R^5$ is cycloalkyl;

(vi) $C_{1-6}$alkyl substituted by $R^5$, where $R^5$ is carboxy (or corresponding protected derivative); and (vii) $C_{1-6}$alkyl substituted by $R^5$, where $R^5$ is —$NY^1Y^2$.

11. A compound according to claim 1 in which within $R^3$ the moiety n is 1.

12. A compound of formula (Ia):

(1a)

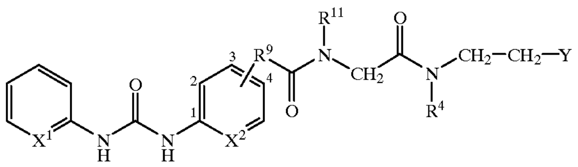

in which $R^4$, $R^9$, $R^{11}$ and Y are as defined in claim 1, $X^1$ and $X^2$ each independently represents $CR^2$, wherein each $R^2$ group is as defined in claim 1, and —$R^9$—CON($R^{11}$)—$CH_2$—CON($R^4$)—$CH_2$—$CH_2$—Y is attached at the ring 3 or 4 position, and their prodrugs and pharmaceutically acceptable salts, and solvates of compounds of formula (Ia) and their prodrugs.

13. A compound according to claim 1 in which $R^9$ represents straight or branched $C_{1-4}$alkylene.

14. A compound according to claim 13 in which $R^9$ represents methylene.

15. A compound according to claim 1 in which $R^{11}$ represents hydrogen, straight or branched $C_{1-4}$alkyl, straight or branched $C_{1-3}$alkyl substituted by aryl, heteroaryl, $C_{3-8}$cycloalky or carboxy, or straight or branched $C_{2-3}$alkyl substituted by —$NY^1$ $Y^2$.

16. A compound according to claim 1 in which $R^4$ represents straight or branched $C_{1-10}$alkyl.

17. A compound according to claim 1 in which $R^4$ represents straight or branched $C_{1-6}$alkyl substituted by $R^5$, where $R^5$ is aryl.

18. A compound according to claim 17 in which $R^4$ represents 3,4-di$C_{1-3}$alkoxybenzyl.

19. A compound according to claim 1 in which $R^4$ represents straight or branched $C_{1-6}$alkyl substituted by $R^5$, where $R^5$ is heteroaryl.

20. A compound according to claim 19 in which $R^4$ represents 3-(imidazol-1-yl)-$C_{1-3}$alkyl.

21. A compound according to claim 1 in which $R^4$ represents straight or branched $C_{1-6}$alkyl substituted by $R^5$, where $R^5$ is $C_{3-8}$cycloalkyl.

22. A compound according to claim 21 in which $R^4$ represents straight or branched $C_{1-3}$alkyl substituted by $C_{5-6}$cycloalkyl.

23. A compound according to claim 1 in which $R^4$ represents straight or branched $C_{1-6}$alkyl substituted by $R^5$, where $R^5$ is $C_{1-6}$alkoxy.

24. A compound according to claim 1 in which $R^4$ represents straight or branched $C_{1-6}$alkyl substituted by halo.

25. A compound according to claim 1 in which $R^4$ represents straight or branched $C_{1-6}$alkyl substituted by $R^5$, where $R^5$ is an acidic functional group.

26. A compound according to claim 25 in which $R^4$ represents straight or branched $C_{1-3}$alkyl substituted by carboxy.

27. A compound according to claim 1 in which $R^4$ represents straight or branched $C_{1-6}$alkyl substituted by $R^5$, where $R^5$ is heterocycloalkyl.

28. A compound according to claim 27 in which $R^4$ represents straight or branched $C_{1-3}$alkyl substituted by 1,3-benzodioxol-5-yl or 1,4-benzodioxan-6-yl.

29. A compound according to claim 1 in which $R^4$ represents straight or branched $C_{1-6}$alkyl substituted by —$NY^1Y^2$.

30. A compound according to claim 29 in which $R^4$ represents straight or branched $C_{2-3}$alkyl substituted by an N-linked 5–7 membered cyclic amine.

31. A compound according to claim 30 in which $R^4$ represents 3-(2-oxo-pyrrolidin-1-yl)-$C_{2-3}$alkyl.

32. A compound according to claim 1 in which $R^4$ represents $C_{1-4}$alkenyl.

33. A compound according to claim 1 in which Y represents carboxy.

34. A compound according claim 12 in which the group —$R^9$—C(=O)—N($R^{11}$)—$CH_2$—C(=O)—$NR^4$—$CH_2$—$CH_2$—Y is attached at the ring 4 position.

35. A compound according to claim 12 in which $R^4$ represents $C_{1-10}$alkyl, $C_{1-6}$alkyl substituted by aryl, heteroaryl, cycloalkyl, heterocycloalkyl, $C_{1-6}$alkoxy, halo or —$NY^1Y^2$, or $R^4$ represents $C_{1-4}$alkenyl; $R^{11}$ represents hydrogen, $C_{1-4}$alkyl, $C_{1-3}$alkyl substituted by aryl, heteroaryl, $C_{3-8}$cycloalkyl or carboxy, or $R^{11}$ represents $C_{2-3}$alkyl substituted by —$NY^1Y^2$; $R^9$ represents $C_{1-4}$alkylene; $X^1$ represents $CR^2$ where $R^2$ is $C_{1-4}$alkyl; $X^2$ represent $CR^2$ where $R^2$ is $C_{1-4}$alkoxy; Y represents carboxy; and the group —$R^9$—C(=O)—N($R^{11}$)—$CH_2$—C(=O)—$NR^4$—$CH_2$—$CH_2$—Y is attached at the ring 4 position; and their prodrugs and pharmaceutically acceptable salts and solvates of such compounds and their prodrugs.

36. A compound according to claim 1 selected from the group consisting of:

3-{[({[3-methoxy-4-(3-o-tolylureido)phenyl]-acetyl}-N-methylamino)-acetyl]-[3-(2-oxo-pyrrolidin-1-yl)-prop-1-yl]-amino}-propionic acid, Compound A;

3-{(3,4-dimethoxy-benzyl)-[({[3-methoxy-4-(3-o-tolylureido)phenyl]-acetyl}-N-methylamino)-acetyl]-amino}-propionic acid, Compound C;

3-{[({[3-methoxy-4-(3-o-tolylureido)phenyl]-acetyl}-amino)-acetyl]-[3-(2-oxo-pyrrolidin-1-yl)-prop-1yl]-amino}-propionic acid, Compound D;

3-[(2,3-dimethoxy-benzyl)-({2-[3-methoxy-4-(3-o-tolylureido)phenyl]-acetylamino}-acetyl)-amino]-propionic acid, Compound AO;

3-[N-(3,4-dimethoxybenzyl)-2-{2-[3-methoxy-4-(3-o-tolylureido)phenyl]acetylamino}acetamido]-propionic acid, Compound BD;

3-{[({[3-methoxy-4-(3-o-tolylureido)phenyl]-acetyl}-N-methylamino)-acetyl]-(3-carboxy-prop-1-yl)-amino}-propionic acid, Compound KW;

3-{(3-ethoxy-4-methoxy-benzyl)-[({[3-methoxy-4-(3-o-tolylureido)phenyl]-acetyl}-amino)-acetyl]-amino}-propionic acid, Compound LE;

3-{(3,4-diethoxy-benzyl)-[({[3-methoxy-4-(3-o-tolylureido)phenyl]-acetyl}-amino)-acetyl]-amino}-propionic acid, Compound LF;

and their prodrugs, and pharmaceutically acceptable salts and solvates of such compounds and their prodrugs.

37. 3-[N-(3,4-Dimethoxybenzyl)-2-{2-[3-methoxy-4-(3-o-tolylureido)phenyl]acetylamino}-acetamido]propionic acid, Compound BD, and its pharmaceutically acceptable salts and solvates.

38. A compound according to claim 1 in which n is 1, 2 or 3.

39. A pharmaceutical composition comprising an effective amount of a compound according to claim 1 or corresponding prodrug, or a pharmaceutically acceptable salt or solvate of such a compound or a prodrug thereof, in association with a pharmaceutically acceptable carrier or excipient.

40. A method for the treatment of a human or non-human animal patient suffering from, or subject to, conditions which can be ameliorated by the administration of an inhibitor of α4β1 mediated cell adhesion comprising administering to said patient an effective amount of a compound according to claim 1 or a corresponding prodrug, or a pharmaceutically acceptable salt or solvate of such a compound or a prodrug thereof.

41. A method according to claim 40 for the treatment of inflammatory diseases.

42. A method according to claim 40 for the treatment of asthma.

43. A method for the treatment of a human or non-human animal patient suffering from, or subject to, an inflammatory disease comprising administering to said patient an effective amount of a compound according to claim 1 or a corresponding prodrug, or a pharmaceutically acceptable salt or solvate of such a compound or a prodrug thereof.

44. A method for the treatment of a human or non-human animal patient suffering from, or subject to, asthma comprising administering to said patient an effective amount of a compound according to claim 1 or a corresponding prodrug, or a pharmaceutically acceptable salt or solvate of such a compound or a prodrug thereof.

45. A method for the treatment of a human or non-human animal patient suffering from, or subject to, conditions which can be ameliorated by the administration of an inhibitor of α4β1 mediated cell adhesion comprising administering to said patient an effective amount of a composition according to claim 39.

46. A method for the treatment of a human or non-human animal patient suffering from, or subject to, an inflammatory disease comprising administering to said patient an effective amount of a composition according to claim 39.

47. A method for the treatment of a human or non-human animal patient suffering from, or subject to, asthma comprising administering to said patient an effective amount of a composition according to claim 39.

48. A pharmaceutical composition comprising an effective amount of a compound according to claim 37 or a corresponding prodrug, or a pharmaceutically acceptable salt or solvate of such a compound or a prodrug thereof, in association with a pharmaceutically acceptable carrier or excipient.

49. A method for the treatment of a human or non-human animal patient suffering from, or subject to, conditions which can be ameliorated by the administration of an inhibitor of α4β1 mediated cell adhesion comprising administering to said patient an effective amount of a compound according to claim 37 or a corresponding prodrug, or a pharmaceutically acceptable salt or solvate of such a compound or a prodrug thereof.

50. A method for the treatment of a human or non-human animal patient suffering from, or subject to, an inflammatory disease comprising administering to said patient an effective amount of a compound according to claim 37 or a corresponding prodrug, or a pharmaceutically acceptable salt or solvate of such a compound or a prodrug thereof.

51. A method for the treatment of a human or non-human animal patient suffering from, or subject to, asthma comprising administering to said patient an effective amount of a compound according to claim 37 or a corresponding prodrug, or a pharmaceutically acceptable salt or solvate of such a compound or a prodrug thereof.

* * * * *